(12) United States Patent
Schadt et al.

(10) Patent No.: US 7,035,739 B2
(45) Date of Patent: Apr. 25, 2006

(54) COMPUTER SYSTEMS AND METHODS FOR IDENTIFYING GENES AND DETERMINING PATHWAYS ASSOCIATED WITH TRAITS

(75) Inventors: Eric E. Schadt, Kirkland, WA (US); Stephanie A. Monks, Seattle, WA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 556 days.

(21) Appl. No.: 10/356,857

(22) Filed: Feb. 3, 2003

(65) Prior Publication Data

US 2003/0224394 A1 Dec. 4, 2003

Related U.S. Application Data

(60) Provisional application No. 60/381,437, filed on May 16, 2002, provisional application No. 60/353,416, filed on Feb. 1, 2002.

(51) Int. Cl.
*G06F 19/00* (2006.01)
*G11C 17/00* (2006.01)
*G05B 15/00* (2006.01)

(52) U.S. Cl. .............................. 702/19; 365/94; 700/1
(58) Field of Classification Search ...................... None
See application file for complete search history.

(56) References Cited

U.S. PATENT DOCUMENTS

| | | |
|---|---|---|
| 5,075,217 A | 12/1991 | Weber |
| 5,324,631 A | 6/1994 | Helentjaris et al. |
| 5,510,270 A | 4/1996 | Fodor et al. |
| 5,539,083 A | 7/1996 | Cook et al. |
| 5,545,522 A | 8/1996 | Van Gelder et al. |
| 5,556,752 A | 9/1996 | Lockhart et al. |
| 5,569,588 A | 10/1996 | Ashby et al. |
| 5,578,832 A | 11/1996 | Trulson et al. |
| 5,716,785 A | 2/1998 | Van Gelder et al. |
| 5,891,636 A | 4/1999 | Van Gelder et al. |
| 5,965,352 A | 10/1999 | Stoughton et al. |
| 6,028,189 A | 2/2000 | Blanchard |
| 6,132,969 A | 10/2000 | Stoughton et al. |
| 6,132,997 A | 10/2000 | Shannon |
| 6,165,709 A | 12/2000 | Friend et al. |
| 6,218,122 B1 | 4/2001 | Friend et al. |
| 6,271,002 B1 | 8/2001 | Linsley et al. |
| 6,324,479 B1 | 11/2001 | Friend et al. |
| 6,368,806 B1 | 4/2002 | Openshaw et al. |

FOREIGN PATENT DOCUMENTS

| | | |
|---|---|---|
| EP | 0 534 858 | 9/1992 |
| WO | WO 98/41531 | 9/1998 |
| WO | WO 199913107 | 3/1999 |
| WO | WO 02/44399 | 6/2002 |
| WO | WO 2003065282 | 8/2003 |
| WO | WO 2003100557 | 12/2003 |
| WO | WO 2004013727 | 2/2004 |
| WO | WO 2004/061616 | 7/2004 |

OTHER PUBLICATIONS

Monks et al. Genetic Inheritance of Gene Expression in Human Cell Lines. Am J. Hum. Genet. vol. 75, pp. 1094-1105 (2004).*
U.S. Appl. No. 60/575,499, filed May 28, 2004, Schadt et al.
U.S. Appl. No. 60/497,470, filed Aug. 21, 2003, Schadt et al.
U.S. Appl. No. 60/492,682, filed Aug. 5, 2003, Schadt et al.
U.S. Appl. No. 60/474,730, filed Apr. 30, 2003, Schadt et al.
U.S. Appl. No. 60/460,343, filed Apr. 2, 2003, Schadt et al.
U.S. Appl. No. 60/460,303, filed Apr. 2, 2003, Schadt et al.
U.S. Appl. No. 60/460,304, filed Apr. 2, 2003, Schadt et al.
U.S. Appl. No. 60/436,684, filed Dec. 27, 2002, Schadt et al.
U.S. Appl. No. 60/400,522, filed Aug. 2, 2002, Schadt et al.
U.S. Appl. No. 60/382,036, filed May 20, 2002, Schadt et al.
PCT/US2004/016917, filed May 28, 2004, Schadt.
PCT/US2004/017754, filed Jun. 4, 2004, Schadt et al.
Aitman et al., 1999, "Identification of Cd36 (Fat) as an insulin-resistance gene causing defective fatty acid and glucose metabolism in hypertensive rats," Nature Genetics 21: 76-83.
Akagi et al., 1996, "Microsatellite DNA markers for rice chromosomes," Theor. Appl. Genet. 93:1071-1077.
Allison et al., 1998, "Multiple phenotype modeling in gene-mapping studies of quantitative traits: power advantages," Am. J. Hum. Genet. 63:1190-1201.
Amos et al., 1990, "A multivariate method for detecting genetic linkage, with application to a pedigree with an adverse lipoprotein phenotype," Am. J. Hum. Genet. 47: 247-254.

(Continued)

*Primary Examiner*—John S. Brusca
(74) *Attorney, Agent, or Firm*—Jones Day

(57) ABSTRACT

A method for associating a gene with a trait exhibited by one or more organisms in a plurality of organisms from a species. A genetic marker map is constructed from a set of genetic markers associated with the plurality of organisms. For each gene in a plurality of genes, a quantitative trait locus analysis is performed using the genetic marker map and a quantitative trait. The quantitative trait locus analysis produces quantitative trait locus data. A quantitative trait comprises an expression statistic for a gene. The expression statistic for a gene is derived from a cellular constituent level that corresponds to the gene in each organism in the plurality of organisms. The quantitative trait locus data are clustered from each quantitative trait locus analysis to form a quantitative trait locus interaction map. Clusters of genes in the map are identified as a candidate pathway group. An expression cluster map is used to refine the candidate pathway group. Multivariate analysis is used to validate the candidate pathway group as a set of genes that are genetically interacting.

163 Claims, 15 Drawing Sheets

OTHER PUBLICATIONS

Barbosa et al., 1976, "The genetic heterogeneity of diabetes : histocompatibility antigens (HLA) in families with maturity-onset type diabetes of the young (MODY) and juvenile, insulin-dependent diabetes (JID) [proceedings]," Diabete. Metab. 2:160.

Blanchard et al., 1996, "High-density oligonucleotide arrays," Biosensors and Bioelectronics 11:687-690.

Blanchard et al., 1996, "Sequence to array: Probing the genome's secrets," Nature Biotechnology 14:1649.

Bligh et al., 1995, "A microsatellite sequence closely linked to the Waxy gene of *Oryza sativa,*" Euphytica 86:83-85.

Bochner et al., 2001, "Phenotype microarrays for high-throughput phenotypic testing and assay of gene function," Genome Res. 11:1246-1255.

Börjeson, 1976, "The aetiology of obesity in children," Acta. Paediar. Scand. 65:279-287.

Bray, 1989, "1989 McCollum Award Lecture. Genetic and hypothalamic mechanisms for obesity-finding the needle in the haystack," Am. J. Clin. Nutr. 50:891-902.

Bray, 1992, "Genetic, hypothalamic and endocrine features of clinical and experimental obesity," Progress in Brain Research 93:333-341.

Brem et al., 2002, "Genetic Dissection of Transcriptional Regulation in Budding Yeast," Science 296:752-755.

Brown et al., 2000, "Knowledge-based analysis of microarray gene expression data by using support vector machines," Proc. Natl. Acad. Sci. USA 97:262-267.

Chirgwin et al., 1979, "Isolation of biologically active ribonucleic acid from sources enriched in ribonuclease," Biochemistry 18:5294-5299.

Cohen et al., 2000, "A computational analysis of whole-genome expression data reveals chromosomal domains of gene expression," Nature Genetics 26:183-186.

Corder et al., 1993, "Gene dose of apolipoprotein E type 4 allele and the risk of Alzheimer's disease in late onset families," Science 261:921-923.

Cox et al., 1999, "Loci on chromosomes 2 (NIDDM1) and 15 interact to increase susceptibility to diabetes in Mexican Americans," Nature Genetics 21:213-215.

DeRisi et al., 1996, "Use of a cDNA microarray to analyse gene expression patterns in human cancer," Nature Genetics 14:457-460.

Doerge, 2002, "Mapping and analysis of quantitative trait loci in experimental populations," Nature Reviews 3:43-52.

Duda et al., 2001, *Pattern Classification,* John Wiley & Sons, New York, NY, p. 521-530.

Duda et al., 2001, *Pattern Classification*, John Wiley & Sons, New York, NY, p. 550-557.

Easton et al., 1993, "Inherited susceptibility to breast cancer, " Cancer Surv. 18:95-113.

Eaves et al., 2002, "Combining Mouse Congenic Strains and Microarray Gene Expression Analyses to Study a Complex Trait: The NOD Model of Type 1 Diabetes," Genome Research 12:232-243.

Egholm et al., 1993, "PNA Hybridizes to complementary oligonucleotides obeying the Watson-Crick hydrogen-bonding rules," Nature 365:566-568.

Elowitz et al., 2002, "Stochastic Gene Expression in a Single Cell," Science 297:1183-1186.

Falk et al., 1987, "Haplotype relative risks: an easy reliable way to construct a proper control sample for risk calculations," Ann. Hum. Genet. 51 (Pt 3):227-233.

Ferguson et al., 1996, "A fiber-optic DNA biosensor microarray for the analysis of gene expression," Nature Biotechnology 14:1681-1684.

Fiehn et al., 2000, "Metabolite profiling for plant functional genomics," Nature Biotech. 18:1157-1161.

Fishel et al., 1993, "The human mutator gene homolog MSH2 and its association with hereditary nonpolyposis colon cancer," Cell 75:1027-1038.

Fodor et al., 1991, "Light-directed, spatially addressable parallel chemical synthesis," Science 251:767-773.

Ford et al., 1994, "Risks of cancer in BRCA1-mutation carriers. Breast Cancer Linkage Consortium," Lancet 343: 692-695.

Friedman et al., 1991, "Molecular mapping of obesity genes, " Mammalian Genome 1:130-144.

Friedman et al., 1992, "Tackling a weighty problem," Cell 69:217-220.

Froehler et al., 1986, "Synthesis of DNA via deoxynucleoside H-phosphonate intermediates," Nucleic Acids Research 14:5399-5407.

Fulker et al., 1999, "Combined Linkage and Association Sib-Pair Analysis for Quantitative Traits," Am. J. Hum. Genet. 64:259-267.

Fullerton et al., 2000, "Apolipoprotein E variation at the sequence haplotype level: implications for the origin and maintenance of a major human polymorphism," Am. J. Hum. Genet. 67:881-900.

Gaasterland et al., 2000, "Making the most of microarray data," Nature Genetics 24:204-206.

Goffeau et al., 1996, "Life with 6000 genes," Science 274:546-567.

Grunau et al., 2001, "MethDB—a public database for DNA methylation data," Nucleic Acids Research 29:270-274.

Grundy et al., 1990, "Metabolic and health complications of obesity," Dis. Mon. 36:641-731.

Haley et al., 1992, "A simple regression method for mapping quantitative trait loci in line crosses using flanking markers," The Genetical Society of Great Britain 69:315-324.

Hayashi et al., 1994, "Detection of additive and dominance effects of QTLs in interval mapping of F2 RFLP data," Theor. Appl. Genet. 87:1021-1027.

Helentjaris et al., 1985, "Restriction fragment polymorphisms as probes for plant diversity and their development as tools for applied plant breeding," Plant Molecular Biology 5:109-118.

Helm et al., 1991, "Classification and identification of bacteria by Fourier-transform infrared spectroscopy," Journal of General Microbiology 137:69-79.

Hu, et al., 1991, "Identification of broccoli and cauliflower cultivars with RAPD markers," Plant Cell Reports 10:505-511.

Hughes et al., 2000, "Functional Discovery via a Compendium of Expression Profiles," Cell 102:109-126.

International Human Genome Consortium, 2001, "Initial sequencing and analysis of the human genome," Nature 409:860-921.

James et al., 1998, "Non-alcoholic steatohepatitis (NASH): a disease of emerging identity and importance," Journal of Hepatolotgy 29:495-501.

Jansen, 1993, "Interval mapping of multiple quantitative trait loci," Genetics 135:205-211.

Jansen, 1994, "Controlling the type I and type II errors in mapping quantitative trait loci," Genetics 138:871-881.

Jansen et al., 2001, "Genetical genomics: the added value from segregation," TRENDS in Genetics 17:388-391.

Jarvis et al., 1973, "Clustering using a similarity measure based on shared near neighbors," IEEE Transactions on computers C-22:1025-1034.

Jaspers et al., 1982, "Genetic heterogeneity in ataxia-telangiectasia studied by cell fusion," Proc. Natl. Acad. Sci. USA 79:2641-2644.

Jiang et al., 1995, "Multiple trait analysis of genetic mapping for quantitative trait loci," Genetics 140:1111-1127.

Karp et al., 2000, "Identification of complement factor 5 as a susceptibility locus for experimental allergic asthma," Nature Immunology, vol. 1, No. 3: 221-226.

Kazuto et al., 1994, "Digenic retinitis pigmentosa due to mutations at the unlinked peripherin/RDS and ROM1 loci," Science 264:1604-1608.

Kearsey et al., 1994, "QTL analysis: a simple 'marker-regression' approach," Theor. Appl. Genet. 89:698-702.

Knapp et al., 1993, "The haplotype-relative-risk (HRR) method for analysis of association in nuclear families," Am. J. Hum. Genet. 52:1085-1093.

Knoll et al., 1993, "Cytogenic and Molecular Studies in the Prader-Willi and Angelman Syndromes: an Overview," American Journal of Medical Genetics 46:2-6.

Kruglyak et al., 1996, "Parametric and nonparametric linkage analysis: a unified multipoint approach," Am. J. Hum. Genet. 58:1347-1363.

Kruglyak et al., 1998, "Faster multipoint linkage analysis using Fourier transforms," J. Comput. Biol. 5:1-7.

Kruglyak et al., 2001, "Variation is the spice of life," Nature Genetics 27:234-236.

Lance et al., 1967, "A general theory of classificatory sorting strategies," Computer Journal 9:373-380.

Lander et al., 1989, "Mapping Mendelian factors underlying quantitative traits using RFLP linkage maps," Genetics 121:185-199.

Lander et al., 1994, "Genetic dissection of complex traits," Science 265:2037-2048.

Lander, 1996, "The new genomics: Global views of biology," Science 274:536-539.

Levsky et al., 2002, "Single-Cell gene expression profiling," Science 297:836-840.

Lockhart et al., 1996, "Expression monitoring by hybridization to high-density oligonucleotide arrays," Nature Biotechnology 14:1675-1680.

Machleder et al., 1997, "Complex Genetic Control of HDL Levels in Mice in Response to an Atherogenic Diet," J. Clin. Invest. 99:1406-1419.

Manley et al., 1999, "Overview of QTL mapping software and introduction to Map Manager QT," Mammalian Genome 10:327-334.

Martinez et al., 1994, "Missing markers when estimating quantitative trait loci using regression mapping," The Genetical Society of Great Britain 73:198-206.

Maskos et al., 1992, "Oligonucleotide hybridisations on glass supports: a novel linker for oligonucleotide synthesis and hybridisation properties of oligonucleotides synthesized in situ," Nucleic Acids Research 20:1679-1684.

McBride et al., 1983, "An investigation of several deoxynucleoside phosphoramidites useful for synthesizing deoxyoligonucleotides," Tetrahedron Letters 24:245-248.

Moll et al., 1991, "The genetic and environmental sources of body mass index variability: the muscatine ponderosity family study," Am. J. Hum. Genet. 49:1243-1255.

Naumann et al., 1991, "Microbiological characterizations by FT-IR spectroscopy," Nature 351:81-82.

Nguyen et al., 1995, "Differential gene expression in the murine thymus assayed by quantitative hybridization of arrayed cDNA clones," Genomics 29:207-216.

Nishina et al., 1994, "Atherosclerosis in genetically obese mice: the mutants obese, diabetes, fat, tubby, and lethal yellow," Metabolism 43:554-558.

Olson et al., 1999, "Tutorial in biostatistics genetic mapping of complex traits," Statistics in Medicine 18:2961-2981.

Patil et al., 2001, "Blocks of limited haplotype diversity revealed by high-resolution scanning of human chromosome 21," Science 294:1719-1723.

Pease et al., 1994, "Light-generated oligonucleotide arrays for rapid DNA sequence analysis," Proc. Natl. Acad. Sci. USA 91:5022-5026.

Pericak-Vance et al., 1991 "Linkage studies in familial Alzheimer disease: evidence for chromosome 19 linkage," Am. J. Hum. Genet. 48:1034-1050.

Prashar et al., 1996, "Analysis of differential gene expression by display of 3' end restriction fragments of cDNAs," Proc. Natl. Acad. Sci. USA 93:659-663.

Reeders et al., 1987, "A study of genetic linkage heterogeneity in adult polycystic kidney disease," Hum. Genet. 76:348-351.

Roberts et al., 2000, "Signaling and circuitry of multiple MAPK pathways revealed by a matrix of global gene expression profiles," Science 287:873-880.

Sagliocco et al., 1996, "Identification of proteins of the yeast protein map using genetically manipulated strains and peptide-mass fingerprinting," Yeast 12:1519-1533.

Schadt et al., 2003, "Genetics of gene expression surveyed in maize, mouse and man," Nature 422:297-302.

Schadt et al., 2003, "A new paradigm for drug discovery: integrating clinical genetic, genomic and molecular phenotype data to identify drug targets," Biochemical Society 31:437-443.

Schena et al., 1995, "Quantitative monitoring of gene expression patterns with a complementary DNA microarray," Science 270:467-470.

Schena et al., 1996, "Parallel human genome analysis; microarray-based expression of 1000 genes," Proc. Natl. Acad. Sci. USA 93:10614-10619.

Shalon et al., 1996, "A DNA microarray system for analyzing complex DNA samples using two-color fluorescent probe hybridization," Genome Research 6:639-645.

Shevchenko et al., 1996, "Linking genome and proteome by mass spectrometry: large-scale identification of yeast proteins from two dimensional gels," Proc. Natl. Acad. Sci. USA 93:14440-14445.

Spielman et al., 1989, "Genetic analysis of IDDM: summary of GAW5 IDDM results," Alan R. Liss, Inc., pp. 43-58.

St. George-Hyslop et al., 1990, "Genetic linkage studies suggest that Alzheimer's disease is not a single homogeneous disorder. FAD Collaborative Study Group," Nature 347:194-197.

Struss et al., 1998, "The use of microsatellite markers for detection of genetic diversity in barley populations," Theor. Appl. Genet. 97:308-315.

Stunkard et al., 1990, "The body mass index of twins who have been reared apart, " The New England Journal of Medicine 322:1483-1487.

Tamayo et al., 1999, "Interpreting patterns of gene expression with self-organizing maps: Methods and application to hematopoietic differentiation," Proc. Natl. Acad. Sci. USA 96:2907-2912.

Terwilliger et al., 1992, "A haplotype-based 'haplotype relative risk' approach to detecting allelic associations," Hum. Hered. 42:337-346.

Velculescu, et al., 1995, "Serial Analysis of Gene Expression," Science 270:484-487.

Venter, et al., 2001, "The sequence of the human genome," Science 291:1304-1351.

Weerd-Kastelein et al., 1972, "Genetic Heterogeneity of xeroderma pigmentosum demonstrated by somatic cell hybridization," Nature New Biology 238:80-83.

Welsh et al., 1990, "Fingerprinting genomes using PCR with arbitrary primers," Nucleic Acids Research 18:7213-7218.

Williams et al., 1999, "Joint Multipoint linkage analysis of multivariate qualitative and quantitative traits. I. Likelihood formulation and simulation results," Am. J. Hum. Genet. 65:1134-1147.

Wu et al., 1993, "Abundance, polymorphism and genetic mapping of microsatellites in rice," Mol. Gen. Genet. 241:225-235.

Younossi, et al., 2002, "Nonalcoholic fatty liver disease: an agenda for clinical research," Hepatology 35:746-752.

Zeng, 1993, "Theoretical basis for separation of multiple linked gene effects in mapping quantitative trait loci," Proc. Natl. Acad. Sci. USA 90:10972-10976.

Zeng, 1994, "Precision mapping of quantitative trait loci," Genetics 136:1457-1468.

* cited by examiner

COMPUTER SYSTEMS AND METHODS FOR IDENTIFYING GENES AND DETERMINING PATHWAYS ASSOCIATED WITH TRAITS

CROSS-REFERENCE TO RELATED APPLICATIONS

This application claims benefit, under 35 U.S.C. § 119(e), of U.S. Provisional Patent Application No. 60/353,416 filed on Feb. 1, 2002 which is incorporated herein, by reference, in its entirety. This application also claims benefit, under 35 U.S.C. § 119(e), of U.S. Provisional Patent Application No. 60/381,437 filed on May 16, 2002 which is incorporated herein, by reference, in its entirety.

1. FIELD OF THE INVENTION

The field of this invention relates to computer systems and methods for identifying genes and biological pathways associated with complex traits. In particular, this invention relates to computer systems and methods for using both cellular constituent level data and genetic data to identify gene-gene interactions, gene-phenotype interactions, and biological pathways linked to complex traits.

2. BACKGROUND OF THE INVENTION

A variety of approaches have been taken to identify genes and pathways that are associated with complex traits, such as human disease. In one approach, attempts have been made to use gene expression data to identify genes and pathways associated with such traits. In another approach, genetic information has been used to attempt to identify genes and pathways associated with complex traits. For instance, clinical measures of a population may be taken to study a complex trait such as a disease found in the population. Risk factors for the trait can be established from these clinical measures. Demographic and environmental factors are further used to explain variation with respect to the trait. Further, genetic variations associated with traits, such as disease-related traits, as well as the disease itself are used to identify regions in the genome linked to a disease. For example, genetic variations in a population may be used to determine what percentage of the variation of the trait in the population of interest can be explained by genetic variation of a single nucleotide polymorphism (SNP), haplotype, or short tandem repeat (STR) marker. However, as will be described below, the elucidation of genes involved in biological pathways that influence a complex trait, such as a disease, using either gene expression or genetic expression approaches, is problematic and generally not successful in many instances.

2.1. Use of Measured Gene Expression Data to Identify Genes and Pathways Associated with Complex Traits Within the past decade, several technologies have made it possible to monitor the expression level of a large number of transcripts at any one time (see, e.g. Schena et al., 1995, Quantitative monitoring of gene expression patterns with a complementary DNA microarray, *Science* 270:467–470; Lockhart et al., 1996, Expression monitoring by hybridization to high-density oligonucleotide arrays, *Nature Biotechnology* 14:1675–1680; Blanchard et al, 1996, Sequence to array: Probing the genome's secrets, *Nature Biotechnology* 14, 1649; U.S. Pat. No. 5,569,588, issued Oct. 29, 1996 to Ashby et al. entitled "Methods for Drug Screening"). In organisms for which the complete genome is known, it is possible to analyze the transcripts of all genes within the cell. With other organisms for which there is an increasing knowledge of the genome, it is possible to simultaneously monitor large numbers of the genes within the cell.

Such monitoring technologies have been applied to the identification of genes that are up regulated or down regulated in various diseased or physiological states, the analyses of members of signaling cellular states, and the identification of targets for various drugs. See, e.g., Friend and Hartwell, U.S. Pat. No. 6,165,709; Stoughton, U.S. Pat. No. 6,132,969; Stoughton and Friend, U.S. Pat. No. 5,965,352; Friend and Stoughton, U.S. Pat. No. 6,324,479; and Friend and Stoughton, U.S. Pat. No. 6,218,122, all incorporated herein by reference for all purposes.

Levels of various constituents of a cell are known to change in response to drug treatments and other perturbations of the biological state of a cell. Measurements of a plurality of such "cellular constituents" therefore contain a wealth of information about the effect of perturbations and their effect on the biological state of a cell. Such measurements typically comprise measurements of gene expression levels of the type discussed above, but may also include levels of other cellular components such as, but by no means limited to, levels of protein abundances, protein activity levels, or protein interactions. Furthermore, the term "cellular constituents" comprises biological molecules that are secreted by a cell including, but not limited to, hormones, matrix metalloproteinases, and blood serum proteins (e.g., granulocyte colony stimulating factor, human growth hormone, etc.). The collection of such measurements is generally referred to as the "profile" of the cell's biological state. Statistical and bioinformatical analysis of profile data has been used to try to elucidate gene regulation events. Statistical and bioinformatical techniques used in this analysis comprises hierarchical cluster analysis, reference or supervised classification approaches and correlation-based analyses. See, e.g., Tamayo et al., 1999, Interpreting patterns of gene expression with self-organizing maps: methods and application of hematopoietic differentiation, *Proc. Natl. Acad. Sci. U.S.A.* 96:2907–2912; Brown et al., 2000, Knowledge-based analysis of microarray gene expression data by using support vector machines, *Proc. Natl. Acad. Sci. U.S.A.*: 97, 262–267; Gaasterland and Bekinraov, Making the most of microarray data, *Nat. Genet.*: 24, 204–206; Cohen et al., 2000, A computational analysis of whole-genome expression data reveals chromosomal domains of gene expression, *Nat. Genet.* 24: 5–6, 2000.

The use of gene expression data to identify genes and elucidate pathways associated with complex traits has typically relied on the clustering of gene expression data over a variety of conditions. See, e.g., Roberts et al., 2000, Signaling and circuitry of multiple MAPK pathways revealed by a matrix of global gene expression profiles; *Science* 287:873; Hughes et al., 2000, Functional Discovery via a Compendium of Expression Profiles, *Cell* 102:109. However, gene expression clustering has a number of drawbacks. First, gene expression clustering has a tendency to produce false positives. Such false positives arise, for example, when two genes coincidentally have correlated expression profiles over a variety of conditions. Second, although gene expression clustering provides information on the interaction between genes, it does not provide information on the topology of biological pathways. For example, clustering of gene expression data over a variety of conditions may be used to determine that genes A and B interact. However, gene expression clustering typically does not provide sufficient information to determine whether gene A is downstream or upstream from gene B in a biological pathway. Third, direct biological experiments are often required to validate the involvement of any gene identified from the clustering of gene expression data in order to increase the confidence that the target is actually valid. For these reasons, the use of gene expression data alone to identify genes involved in complex traits, such as various complex human diseases, has often proven to be unsatisfactory.

2.2. Use of Genetics Data to Identify Genes and Pathways Associated with Complex Traits Genetics data have been used in the field of complex trait analysis in order to attempt to identify the genes that affect such traits. A key development in such pursuits has been the development of large collections of molecular/genetic markers, which can be used to construct detailed genetic maps of species, such as humans. These maps are used in Quantitative Trait Locus (QTL) mapping methodologies such as single-marker mapping, interval mapping, composite interval mapping and multiple trait mapping. For a review, see Doerge, 2002, Mapping and analysis of quantitative trait loci in experimental populations, *Nature Reviews: Genetics* 3:43–62. QTL mapping methodologies provide statistical analysis of the association between phenotypes and genotypes for the purpose of understanding and dissecting the regions of a genome that affect complex traits.

A quantitative trait locus (QTL) is a region of any genome that is responsible for some percentage of the variation in the quantitative trait of interest. The goal of identifying all such regions that are associated with a specific complex phenotype is typically difficult to accomplish because of the sheer number of QTL, the possible epistasis or interactions between QTL, as well as many additional sources of variation that can be difficult to model and detect. To address these problems, QTL experiments can be designed with the aim of containing the sources of variation to a limited number in order to improve the chances of dissecting a complex phenotype. In general, a large sample of individuals has to be collected to represent the total population, to provide an observable number of recombinants and to allow a thorough assessment of the trait under investigation. Using this information, coupled with one of several methodologies to detect or locate QTL, associations between quantitative traits and genetic markers are made as steps toward understanding the genetic basis of complex traits.

A drawback with QTL approaches is that, even when genomic regions that have statistically significant associations with complex traits are identified, such regions are usually so large that subsequent experiments, used to identify specific causative genes in these regions, are time consuming and laborious. High density marker maps of the genomic regions are required. Furthermore, physical resequencing of such regions is often required. In fact, because of the size of the genomic regions identified, there is a danger that causative genes within such regions simply will not be identified. In the event of success, and the genomic region containing genes that are responsible for the complex trait variation are elucidated, the expense and time from the beginning to the end of this process is often too great for identifying genes and pathways associated with complex traits, such as complex human diseases.

In the case of humans, the use of genetics to identify genes and pathways associated with traits follows a very standard paradigm. First, a genome-wide linkage study is performed using hundreds of genetic markers in family-based data to identify broad regions linked to the trait. The result of this standard sort of linkage analysis is the identification of regions controlling for the trait, thereby restricting attention from the 30,000 plus genes to perhaps as few as 500 to 1000 genes in a particular region of the genome that is linked to the trait. However, the regions identified using linkage analysis are still far too broad to identify candidate genes associated with the trait. Therefore, such linkage studies are typically followed up by fine mapping the regions of linkage using higher density markers in the linkage region, increasing the number of families in the analysis, and identifying alternative populations for study. These efforts further restrict attention to narrower regions of the genome, on the order of 100 genes in a particular region linked to the trait. Even with the more narrowly defined linkage region, the number of genes to validate is still unreasonably large. Therefore, research at this stage focuses on identifying candidate genes based on putative function of known or predicted genes in the region and the potential relevance of that function to the trait. This approach is problematic because it is limited to what is currently known about genes. Often, such knowledge is limited and subject to interpretation. As a result, researchers are often led astray and do not identify the genes affecting the trait.

There are many reasons that standard genetic approaches have not proven very successful in the identification of genes associated with complex traits, such as common human diseases, or the biological pathways associated with such complex traits. First, common human diseases such as heart disease, obesity, cancer, osteoporosis, schizophrenia, and many others are complex in that they are polygenic. That is, they potentially involve many genes across several different biological pathways and they involve complex gene-environment interactions that obscure the genetic signature. Second, the complexity of the diseases leads to a heterogeneity in the different biological pathways that can give rise to the disease. Thus, in any given heterogeneous population, there may be defects across several different pathways that can give rise to the disease. This reduces the ability to identify the genetic signal for any given pathway. Because many populations involved in genetic studies are heterogeneous with respect to the disease, multiple defects across multiple pathways are operating within the population to give rise to the disease. Third, as outlined above, the genomic regions associated with a linkage to a complex disease are large and often contain a number of genes and possible variants that are potentially associated with the disease. Fourth, the traits and disease states themselves are often not well defined. Therefore, subphenotypes are often overlooked even though these subphenotypes implicate different sets of biological pathways. This reduces the power of detecting the associations. Fifth, even when gene expression and a trait are highly correlated, the genes may not give the same genetic signature. Sixth, in cases where gene expression and a trait are moderately correlated, or not correlated at all, the genes may give rise to the same genetic signature.

In addition to the heterogeneity problems discussed above, the identification of genes and biological pathways associated with complex traits, such as complex human diseases, using genetics data is confounded, when using human subjects, due to the inability to use common genetic techniques and resources in humans. For example, humans cannot be crossed in controlled experiments. Therefore, there is typically very little pedigree data available for humans. Elucidation of genes associated with complex diseases in humans is also difficult because humans are diploid organisms containing two genomes in each nucleate cell, making it very hard to determine the DNA sequence of the haploid genome. Because of these limitations, genetic approaches to discovering genes and biological pathways associated with complex human diseases is unsatisfactory.

Companies such as deCode Genetics (Reykjavik, Iceland) study populations that are isolated and so are more homogenous with respect to disease, thereby increasing the power to detect association. The disease variations themselves in such populations are greatly reduced as founder effects for many diseases are evident (i.e., specific forms of diseases in such populations most likely arose from a single or small numbers of founders of the population). Other companies, such as Sequenome (San Diego, Calif.), use twin cohorts to study complex diseases. Identical twins are a powerful tool in establishing the genetic component of a trait. The genetic component of a trait is defined as the degree to which a given trait is under genetic control. Dizygotic twins allow for age, gender and environment matching, which helps reduce many of the confounding factors that often reduce the power of genetic studies. In addition, the completion of the human and mouse genomes has made the job of identifying candidate genes in a region of linkage far easier, and it reduces dependency on considering only known genes, since genomic regions can be annotated using ab initio gene prediction software to identify novel candidate genes associated with the disease. Further, the use of demographic, epidemiological and clinical data in more sophisticated models helps explain much of the trait variation in a population. Reducing the overall variation in this way increases the power to detect genetic variation. The identification of millions of SNPs allows finer mapping in any given region of the genome and direct association testing of very large case/control populations, thereby reducing the need to study families and more directly identify the degree to which any genetic variant affects a given population. Finally, our understanding of disease and the need to subphenotype a given disease is now more fully appreciated and aids in reducing the heterogeneity of the disease under study. Technologies such as microarrays have greatly facilitated the ability to subclassify disease subtypes for a given disease. However, all of the methods still fall short when it comes to efficiently identifying genes and pathways associated with complex diseases.

2.3. Obesity

Obesity represents the most prevalent of body weight disorders, and it is the most important nutritional disorder in the western world, with estimates of its prevalence ranging from 30% to 50% within the middle-aged population. Other body weight disorders, such as anorexia nervosa and bulimia nervosa, which together affect approximately 0.2% of the female population of the western world, also pose serious health threats. Further, such disorders as anorexia and cachexia (wasting) are also prominent features of other diseases such as cancer, cystic fibrosis, and AIDS.

It has been estimated that half of all Americans are overweight. Within the United States about 24% of men and 27% of women are defined as mildly to severely obese. Individuals 20% over ideal weight guidelines are considered obese. Obesity is classified as mild (20–40% overweight), moderate (41–100% overweight), and severe (>100%) overweight. Severe obesity is relatively rare, affecting less than 0.5% of all obese individuals and about 0.1% of the total population.

In order to measure obesity, the weight/height ratio may be calculated by obtaining the weight of an individual in kilograms (kg) and dividing this value by the square of the height of the individual in meters. Alternatively, the weight/height ratio of an individual may be obtained by multiplying the weight of the individual in pounds (lbs) by 703 and dividing this value by the square of the height of the individual (in inches (in)). These ratios are typically referred to as BMI. Thus, $BMI=kg/m^2$ or $BMI=(lbs.\times 703)/(in)^2$. Where BMI is utilized as a measure of obesity, an individual is considered overweight when BMI values range between 25.0 and 29.9. Obesity is defined as BMI values greater than or equal to 30.0. The World Health Organization assigns BMI values as follows: 25.0–29.9, Grade I obesity (moderately overweight); 30–39.9, Grade II obesity (severely overweight); and 40.0 or greater, Grade III obesity (massive/morbid obesity). Using weight tables, obesity is classified as mild (20–40% overweight), moderate (41–100% overweight), and severe (>100%) overweight. Individuals 20% over ideal weight guidelines are considered obese. Individuals 1–19.9% over ideal weight are classified as overweight.

Obesity also contributes to other diseases. For example, this disorder is responsible for increased incidence of diseases such as coronary artery disease, hypertension, stroke, diabetes, hyperlipidemia, and some cancers (See, e.g., Nishina, P. M. et al., 1994, Metab. 43: 554–558; Grundy, S. M. & Barnett, J. P., 1990, Dis. Mon. 36: 641–731). Obesity is not merely a behavioral problem, i.e., the result of voluntary hyperphagia. Rather, the differential body composition observed between obese and normal subjects results from differences in both metabolism and neurologic/metabolic interactions. These differences seem to be, to some extent, due to differences in gene expression, and/or level of gene products or activity (Friedman, J. M. et al., 1991, Mammalian Gene 1: 130–144).

The epidemiology of obesity strongly shows that the disorder exhibits inherited characteristics (Stunkard, 1990, N. Eng. J. Med. 322: 1438). Moll et al. have reported that, in many populations, obesity seems to be controlled by a few genetic loci (Moll et al., 1991, Am. J. Hum. Gen. 49: 1243). In addition, human twin studies strongly suggest a substantial genetic basis in the control of body weight, with estimates of heritability of 80–90% (Simopoulos, A. P. & Childs, B., eds., 1989, in "Genetic Variation and Nutrition in Obesity", World Review of Nutrition and Diabetes 63, S. Karger, Basel, Switzerland; Borjeson, M., 1976, Acta. Paediatr. Scand. 65: 279–287).

In other studies, non-obese persons who deliberately attempted to gain weight by systematically over-eating were found to be more resistant to such weight gain and able to maintain an elevated weight only by very high caloric intake. In contrast, spontaneously obese individuals are able to maintain their status with normal or only moderately elevated caloric intake. In addition, it is a commonplace experience in animal husbandry that different strains of swine, cattle, etc., have different predispositions to obesity. Studies of the genetics of human obesity, and of animal models of obesity demonstrate that obesity results from complex defective regulation of both food intake, food induced energy expenditure, and of the balance between lipid and lean body anabolism.

There are a number of genetic diseases in man and other species that feature obesity among their more prominent symptoms, along with, frequently, dysmorphic features and mental retardation. For example, Prader-Willi syndrome (PWS; reviewed in Knoll, J. H. et al., 1993, Am. J. Med. Genet. 46: 2–6) affects approximately 1 in 20,000 live births, and involves poor neonatal muscle tone, facial and genital deformities, and generally obesity.

In addition to PWS, many other pleiotropic syndromes have been characterized that include obesity as a symptom. These syndromes are genetically straightforward, and appear to involve autosomal recessive alleles. Such diseases include, among others, Ahlstroem, Carpenter, Bardet-Biedl, Cohen, and Morgagni-Stewart-Monel Syndromes.

A number of models exists for the study of obesity (see, e.g., Bray, 1992, Prog. Brain Res. 93: 333–341; and Bray, 1989, Amer. J. Clin. Nutr. 5: 891–902). For example, animals having mutations that lead to syndromes that include obesity symptoms have also been identified. Attempts have been made to utilize such animals as models for the study of obesity, and the best studied animal models to date for genetic obesity are mice. For reviews, see, e.g., Friedman et al., 1991, Mamm. Gen. 1: 130–144; Friedman and Liebel, 1992, Cell 69: 217–220.

Studies utilizing mice have confirmed that obesity is a very complex trait with a high degree of heritability. Mutations at a number of loci have been identified that lead to obese phenotypes. These include the autosomal recessive mutations obese (ob), diabetes (db), fat (fat), and tubby (tub). Thus, methods are needed in the art for identifying genes and biological pathways that affect complex traits such as obesity.

Given the above background, what is needed in the art are improved methods for identifying genes and biological pathways that affect complex traits such as diseases.

Discussion or citation of a reference herein will not be construed as an admission that such reference is prior art to the present invention.

3. SUMMARY OF THE INVENTION

The present invention provides an improvement over the art by treating the transcription levels of a plurality of genes in a population of interest as multiple molecular phenotypes and by simultaneously considering each of these phenotypes. The present invention integrates these transcription level phenotypes with more classic phenotypes, such as risk traits for complex diseases and disease states. Underlying most of the traits of interest and many of the factors observed as independent variables for trait variation are changes in transcription levels. Therefore, fully integrating changes in transcription levels across a population of interest provides a direct connection to the genetic variation associated with the trait and helps elucidate the disease processes at the molecular levels by tying the genetics, environment, and transcript abundances together as a single unit to explain trait variation associated with disease. In one embodiment of the present invention, quantitative trait locus (QTL) analysis of each gene in the plurality of genes in the population of interest is performed to produce QTL data. The QTL data is then clustered in order to identify a gene that is associated with a trait under study.

One embodiment of the present invention provides a method for associating a target gene with a trait exhibited by one or more organisms in a plurality of organisms. A genetic marker map is constructed from a set of genetic markers associated with the plurality of organisms. For each gene G in the plurality of genes in the genome of the plurality of organisms, a quantitative trait locus analysis is performed using the genetic marker map and a quantitative trait. The quantitative trait used in each of quantitative trail locus analyses comprises an expression statistic for gene G for each organism in the plurality of organisms. The quantitative trait locus analysis produces quantitative trait locus data. The quantitative trait locus data from each quantitative trait locus analysis is clustered in order to form a quantitative trait locus interaction map. The target gene is then identified in the quantitative trait locus interaction map, thereby associating the target gene with the trait exhibited by one or more organisms in the plurality of organisms.

In some embodiments of the present invention, the expression statistic for each gene G is computed by transforming an expression level measurement of gene G for each organism in the plurality of organisms. In one embodiment, the transforming comprises normalizing the expression level measurement of gene G in order to form the expression statistic. Normalization routines used in accordance with the present invention include, but are not limited to Z-score of intensity, median intensity, log median intensity, Z-score standard deviation log of intensity, Z-score mean absolute deviation of log intensity, calibration DNA gene set, user normalization gene set, ratio median intensity correction, and intensity background correction.

In some embodiments of the present invention, each quantitative trait locus analysis comprises (i) testing for linkage between [a] a position in a chromosome, in the genome of the plurality of organisms, and [b] the quantitative trait used in the quantitative trait locus analysis, (ii) advancing the position in the chromosome by an amount, and (iii) repeating steps (i) and (ii) until the end of the chromosome is reached. In some embodiments, the quantitative trait locus data produced from each respective quantitative trait locus analysis comprises a logarithmic of the odds score computed at each position tested. In some embodiments, a quantitative trait locus vector is created for each quantitative trait tested in the chromosome. In such embodiments, the quantitative trait locus vector comprises the LOD score at each position tested by the quantitative trait locus analysis corresponding to the quantitative trait. In some embodiments, the clustering of the quantitative trait locus data from each quantitative trait locus analysis comprises clustering each quantitative trait locus vector. Several different types of similarity metrics can be used as a basis for such clustering. Representative metrics include, but are not limited to, Euclidean distance, a squared Euclidean distance, a Euclidean sum of squares, a Manhattan metric, a Pearson correlation coefficient, and a squared Pearson correlation coefficient. Such metrics are computed between quantitative trait locus vector pairs.

In some embodiments of the present invention, the clustering of the quantitative trait locus data from each quantitative trait locus analysis comprises application of a hierarchical clustering technique, application of a k-means technique, application of a fuzzy k-means technique, application of Jarvis-Patrick clustering, application of a self-organizing map, or application of a neural network. In some embodiments the hierarchical clustering technique is an agglomerative clustering procedure. In other embodiments, the agglomerative clustering procedure is a nearest-neighbor algorithm, a farthest-neighbor algorithm, an average linkage algorithm, a centroid algorithm, or a sum-of-squares algorithm. In yet other embodiments, the hierarchical clustering technique is a divisive clustering procedure.

Some embodiments of the invention further comprise constructing a gene expression cluster map from each expression statistic created by the transforming step. In one embodiment, the gene expression cluster map is made by (i) creating a plurality of gene expression vectors, each gene expression vector in the plurality of gene expression vectors representing a gene in the plurality of genes; (ii) computing a plurality of correlation coefficients, wherein each correlation coefficient in the plurality of correlation coefficients is computed between a gene expression vector pair in the plurality of gene expression vectors; and (iii) clustering the plurality of gene expression vectors based on the plurality of correlation coefficients to form the gene expression cluster map. In some embodiments of the present invention the target gene is identified in the quantitative trait locus interaction map after filtering the quantitative trait locus interaction map in order to obtain a candidate pathway group. In some embodiments, the clustering of the plurality of gene expression vectors comprises application of a hierarchical clustering technique, application of a k-means technique, application of a fuzzy k-means technique, application of Jarvis-Patrick clustering, application of a self-organizing map, or application of a neural network.

In still other embodiments of the present invention the target gene is identified in the quantitative trait locus interaction map by filtering the quantitative trait locus interaction map in order to obtain a candidate pathway group. In some embodiments, this filtering comprises selecting those quantitative trait locus for the candidate pathway group that interact most strongly with another quantitative trait locus in the quantitative trait locus interaction map. In some embodiments, the quantitative trait locus that interact most strongly with another quantitative trait locus in the quantitative trait locus interaction map are those quantitative trait locus in the quantitative trait locus interaction map that share a correlation coefficient with another quantitative trait locus in the quantitative trait locus interaction map that is higher than 75%, 85%, or 95% of all correlation coefficients computed between quantitative trait locus in the quantitative trait locus interaction map.

In some embodiments of the present invention, the identification of the target gene in the clustered quantitative trait locus data further comprises fitting a multivariate statistical model to the candidate pathway group in order to test the degree to which each quantitative trait locus making up the candidate pathway group belong together. In some embodiments, the multivariate statistical model simultaneously considers multiple quantitative traits. In some embodiments, the multivariate statistical model models epistatic interactions between quantitative trait locus in the candidate pathway group.

In some embodiments of the present invention, each expression level measurement is determined by measuring an amount of a corresponding cellular constituent in one or more cells from each organism in the plurality of organisms. In some embodiments, the amount of the corresponding cellular constituent comprises an abundance of a RNA species present in one or more cells of the organism. In some embodiments, the abundance is measured by a method comprising contacting a gene transcript array with RNA from the one or more cells, or with cDNA derived therefrom. In such embodiments the gene transcript array comprises a surface with attached nucleic acids or nucleic acid mimics and the nucleic acids or nucleic acid mimics are capable of hybridizing with the RNA species, or with cDNA derived therefrom.

In some embodiments of the present invention, the set of genetic markers used to construct the genetic marker map comprise single nucleotide polymorphisms (SNPs), microsatellite markers, restriction fragment length polymorphisms, short tandem repeats, DNA methylation markers, or sequence length polymorphisms. In still other embodiments of the present invention, the association of the target gene with the trait exhibited by one or more organisms in the plurality of organisms results in the placement of the target gene in a pathway group that comprises genes that are part of the same or related biological pathway.

In some embodiments of the present invention, genotype data is used to construct the genetic marker map, in addition to the set of genetic markers associated with the plurality of organisms. This genotype data comprises the alleles, for each marker in the set of genetic markers, in each organism in the plurality of organisms. In other embodiments of the present invention, pedigree data is used to construct the genetic marker map from the set of genetic markers associated with the plurality of organisms. This pedigree data shows one or more relationships between organisms in the plurality of organisms. In some embodiments, the plurality of organisms is human and the one or more relationships between organisms in the plurality of organisms is pedigree data. In still other embodiments the plurality of organisms comprises an $F_2$ population and the one or more relationships between organisms in the plurality of organisms indicates which organisms in the plurality of organisms are members of the $F_2$ population.

Another embodiment of the present invention provides a computer program product for use in conjunction with a computer system. The computer program product comprises a computer readable storage medium and a computer program mechanism embedded therein. The computer program mechanism comprises a marker map construction module, a quantitative trait locus analysis module, and a clustering module. The marker map construction module is for constructing a genetic marker map from a set of genetic markers associated with a plurality of organisms. The quantitative trait locus analysis module is for performing, for each gene G in a plurality of genes in the genome of the plurality of organisms, a quantitative trait locus analysis using the genetic marker map and a quantitative trait, in order to produce quantitative trait locus data. The quantitative trait used in each quantitative trail locus analysis comprises an expression statistic for gene G for each organism in the plurality of organisms. The clustering module is for clustering the quantitative trait locus data from each quantitative trait locus analysis to form a quantitative trait locus interaction map. The target gene is associated with a trait exhibited by one or more organisms in the plurality of organisms when the target gene is identified in the quantitative trait locus interaction map.

Still another embodiment of the present invention provides a computer system for associating a target gene with a trait exhibited by one or more organisms in a plurality of organisms. The computer system comprises a central processing unit and a memory that are coupled to the central processing unit. The memory stores a marker map construction module, a quantitative trait locus analysis module, and a clustering module. The marker map construction module is for constructing a genetic marker map from a set of genetic markers associated with the plurality of organisms. The quantitative trait locus analysis module is for performing, for each gene G in a plurality of genes in the genome of the plurality of organisms, a quantitative trait locus analysis using the genetic marker map and a quantitative trait, in order to produce quantitative trait locus data. The quantitative trait used in each quantitative trail locus analysis comprises an expression statistic for gene G for each organism in the plurality of organisms. The clustering module is for clustering the quantitative trait locus data from each quantitative trait locus analysis to form a quantitative trait locus interaction map. In this embodiment, the target gene is associated with the trait when the target gene is identified in the quantitative trait locus interaction map.

Another embodiment of the present invention provides a computer system for associating a target gene with a trait exhibited by one or more organisms in a plurality of organisms. The computer system comprises a central processing unit and a memory. The memory is coupled to the central processing unit. The memory stores a clustering module and a database. The database stores quantitative trait locus data from a plurality of quantitative trait locus analyses. Each quantitative trait locus analysis in the plurality of quantitative trait locus analyses is performed for a gene G in a plurality of genes in the genome of a plurality of organisms using a genetic marker map and a quantitative trait in order to produce the quantitative trait locus data. For each quantitative trait locus analysis, the quantitative trait comprises an expression statistic for the gene G, for which the quantitative trait locus analysis is performed, from each organism in the plurality of organisms. Furthermore, the genetic marker map is constructed from a set of genetic markers associated with the plurality of organisms. The clustering module clusters the quantitative trait locus data stored in the database to form a quantitative trait locus interaction map. The target gene is associated with the trait exhibited by one or more organisms in the plurality of organisms when the target gene is identified in the quantitative trait locus interaction map.

One embodiment of the invention provides a method for identifying members of a biological pathway in a species. The method comprises (a) clustering quantitative trait locus data from a plurality of quantitative trait locus analyses to form a quantitative trait locus interaction map, wherein each quantitative trait locus analysis in the plurality of quantitative trait locus analyses is performed for a gene in a plurality of genes in the genome of the species using a genetic marker map and a quantitative trait in order to produce the quantitative trait locus data, wherein, for each quantitative trait locus analysis, the quantitative trait comprises an expression statistic for the gene for which the quantitative trait locus analysis has been performed, for each organism in a plurality of organisms that are members of the species; and wherein the genetic marker map is constructed from a set of genetic markers associated with the species; and (b) identifying a cluster of genes in the quantitative trait locus interaction map, thereby identifying members of the biological pathway.

In some embodiments, the method further comprises, prior to the clustering, constructing the genetic marker map from the set of genetic markers associated with the plurality of organisms.

Another embodiment of the present invention provides a computer program product for use in conjunction with a computer system. The computer program product comprises a computer readable storage medium and a computer program mechanism embedded therein. The computer program mechanism comprises an identification module for identifying members of a biological pathway in a species. The identification module comprises (a) instructions for clustering quantitative trait locus data from a plurality of quantitative trait locus analyses to form a quantitative trait locus interaction map, wherein each quantitative trait locus analysis in the plurality of quantitative trait locus analyses is performed for a gene in a plurality of genes in the genome of the species using a genetic marker map and a quantitative trait in order to produce the quantitative trait locus data, wherein, for each quantitative trait locus analysis, the quantitative trait comprises an expression statistic for the gene for which the quantitative trait locus analysis has been performed, for each organism in a plurality of organisms that are members of the species; and wherein the genetic marker map is constructed from a set of genetic markers associated with the species; and (b) instructions for identifying a cluster of genes in the quantitative trait locus interaction map, thereby identifying members of the biological pathway.

4. BRIEF DESCRIPTION OF THE DRAWINGS

Figure 7:
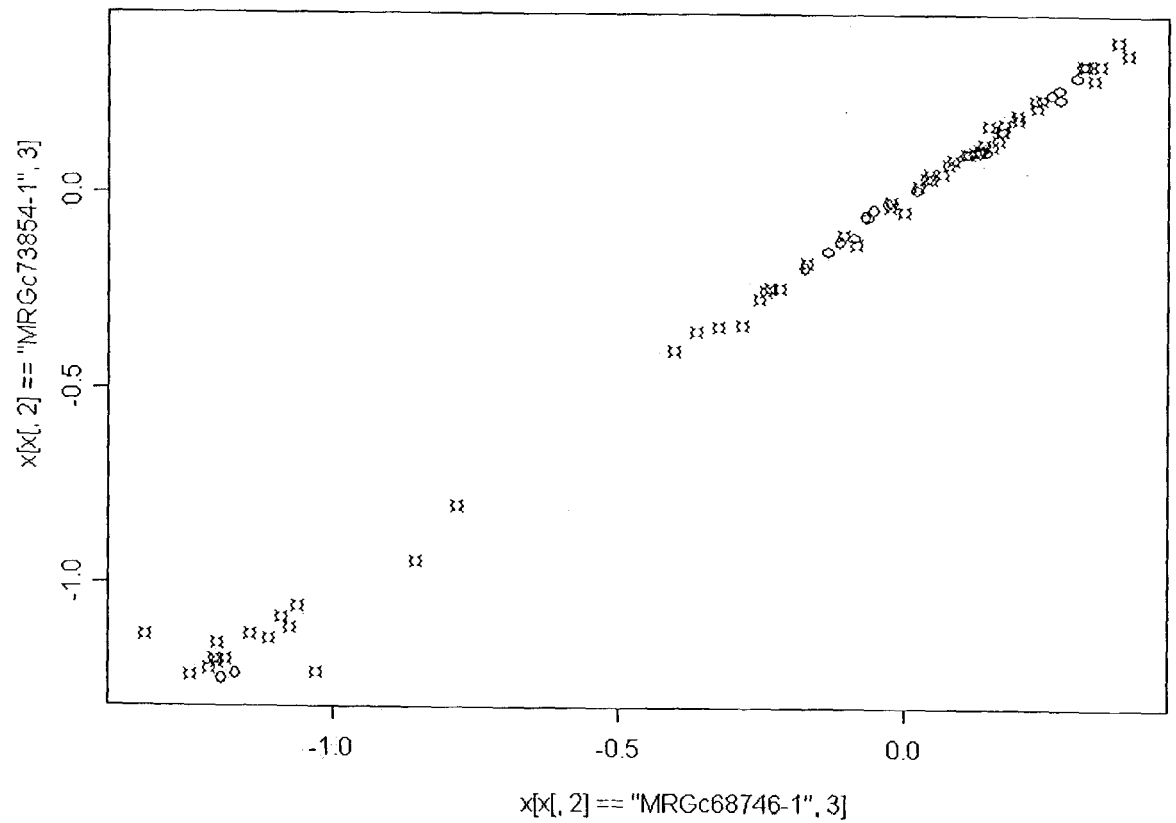

FIG. 7 compares the expression value for one gene to the expression values of another gene across 76 ear-leaf tissues from *Zea mays* in accordance with one embodiment of the present invention.

Figure 8:
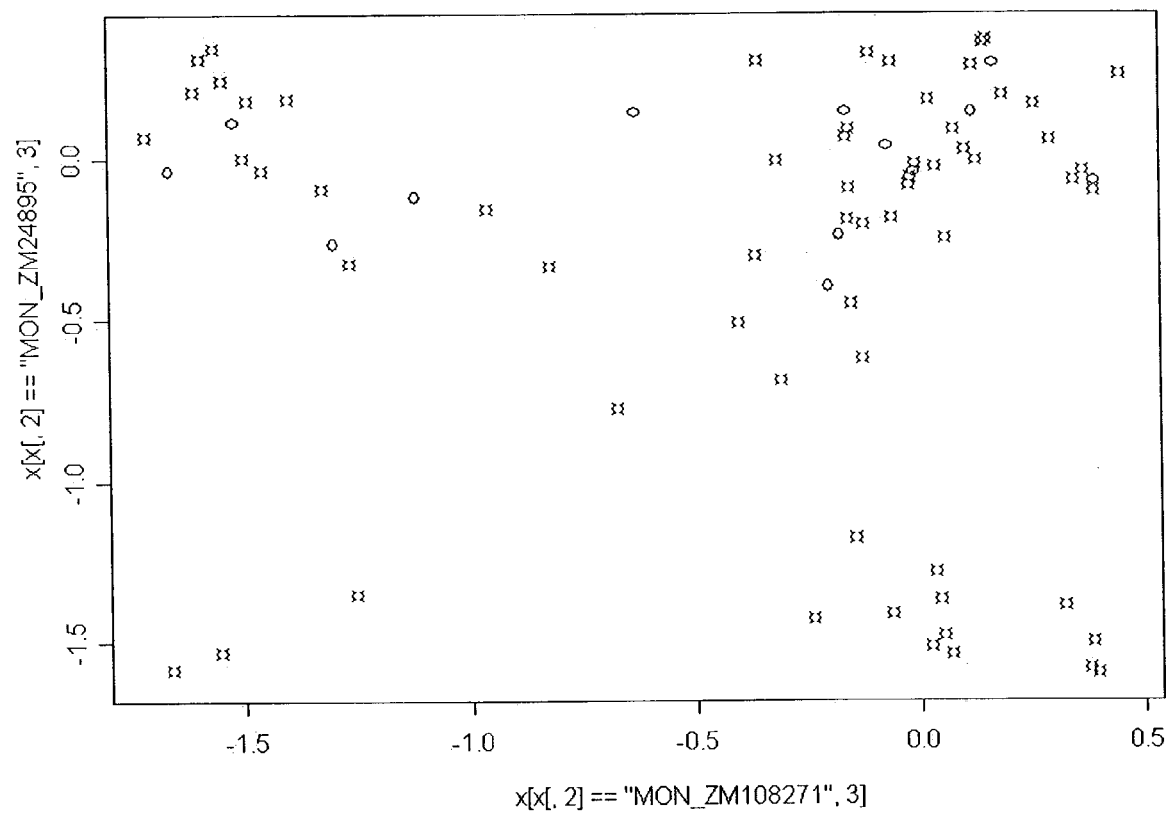

FIG. 8 compares the expression value for one gene to the expression values of another gene across 76 ear-leaf tissues from *Zea mays* in accordance with one embodiment of the present invention.

Figure 9:
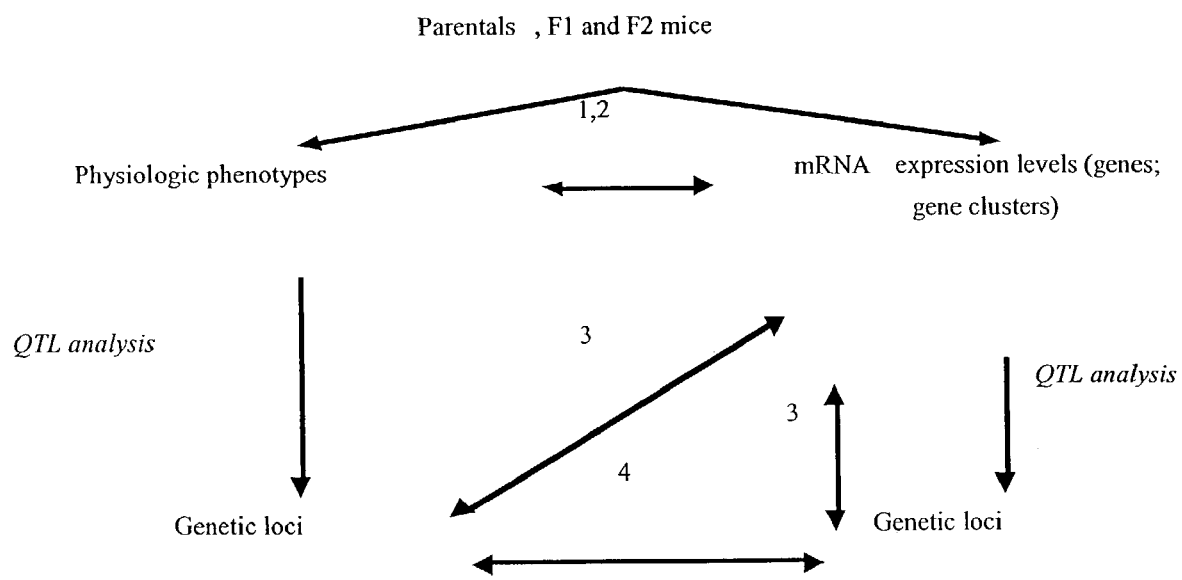

FIG. 9 illustrates genetic crosses used to derive a mouse model for a complex human disease in accordance with one embodiment of the present invention.

Figure 10:
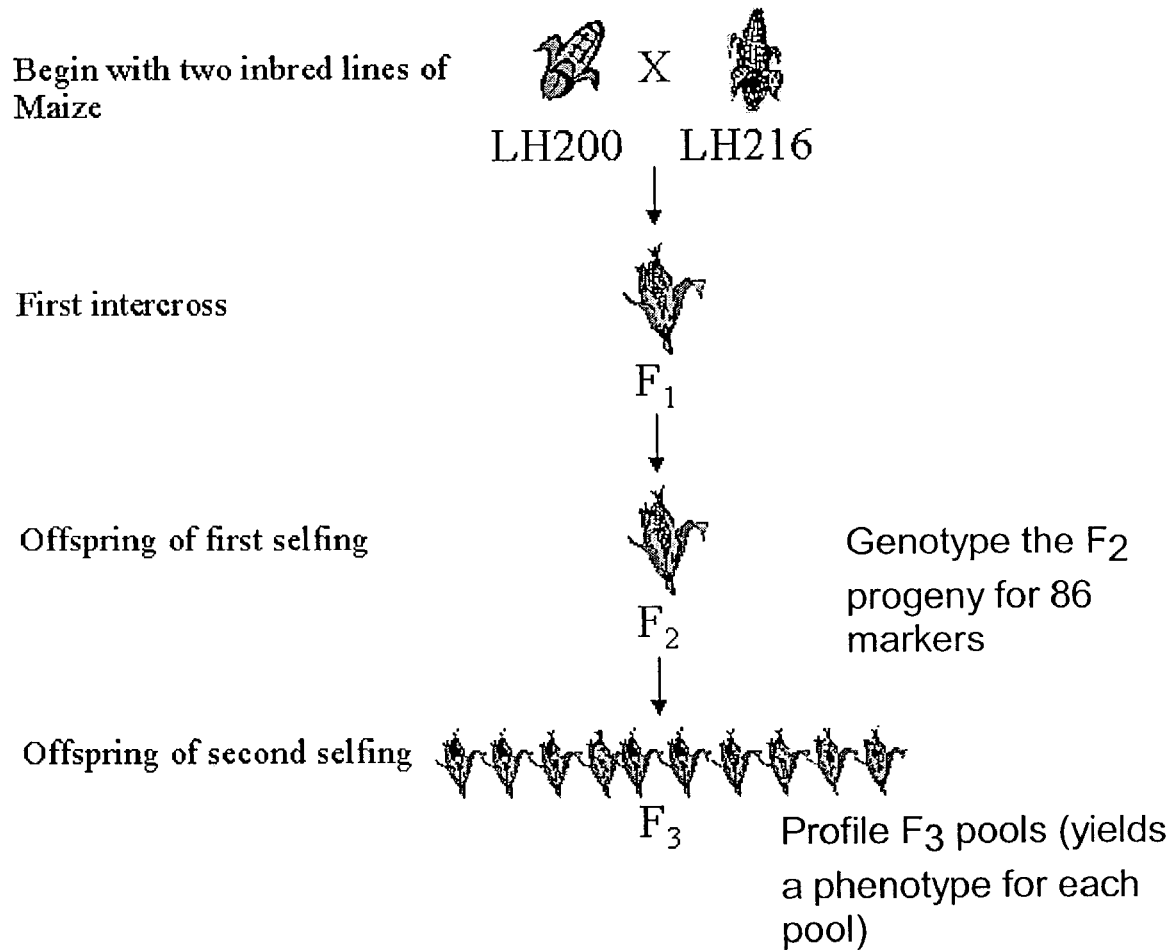

FIG. 10 illustrates data based on an experimental cross done in *Zea mays* in order to yield suitable genotype and pedigree data.

Figure 11:
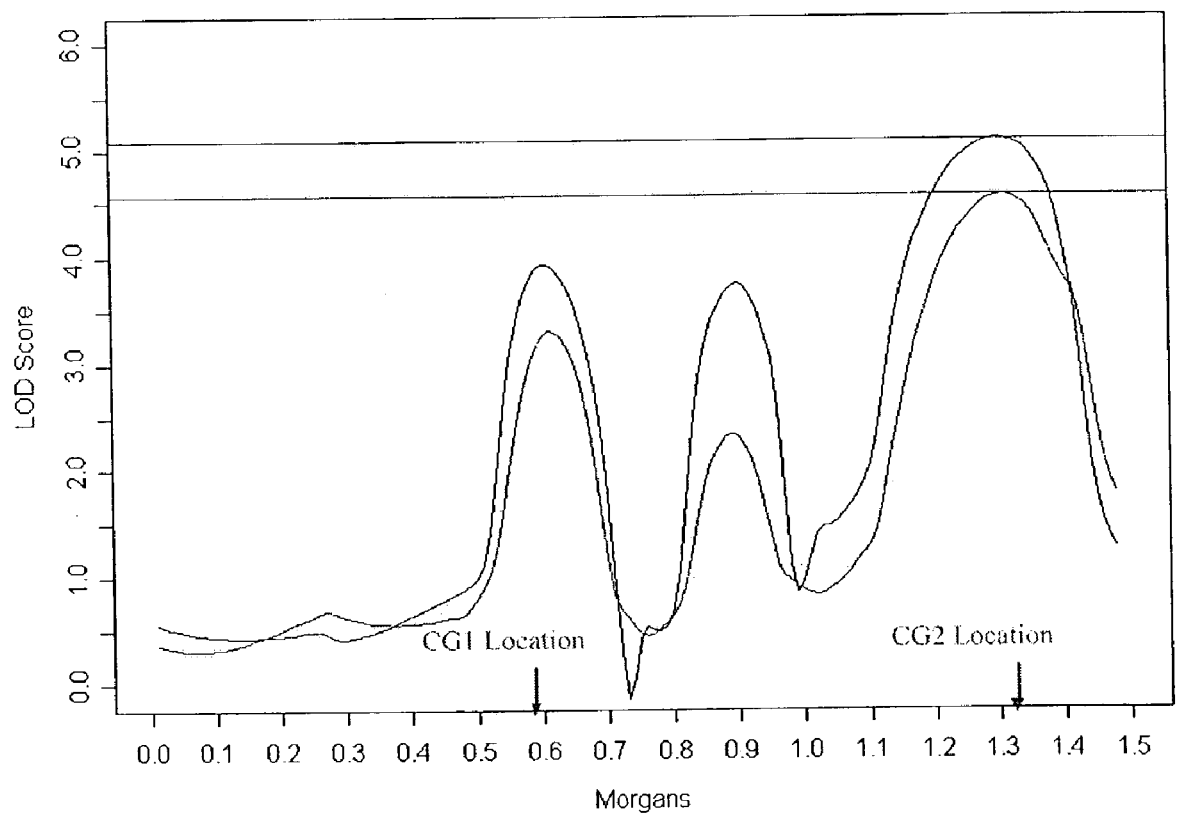

FIG. 11 plots the logarithmic of the odds (LOD) score for two gene expression traits as a function of chromosome position on chromosome 5 of *Zea mays*.

Figure 12:
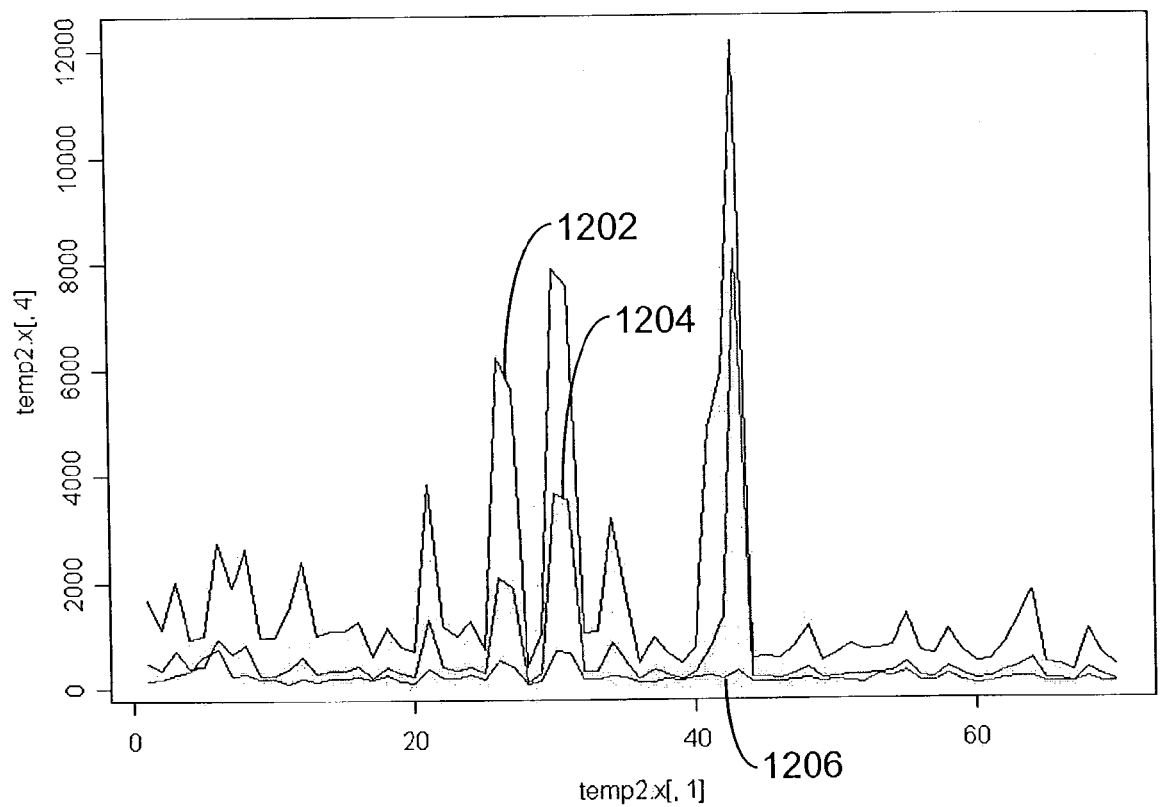

FIG. 12 plots the number of genes having a LOD score that falls into one of three designated ranges (curves 1202, 1204 and 1206) as a function of *Zea mays* chromosome position.

Figure 13:
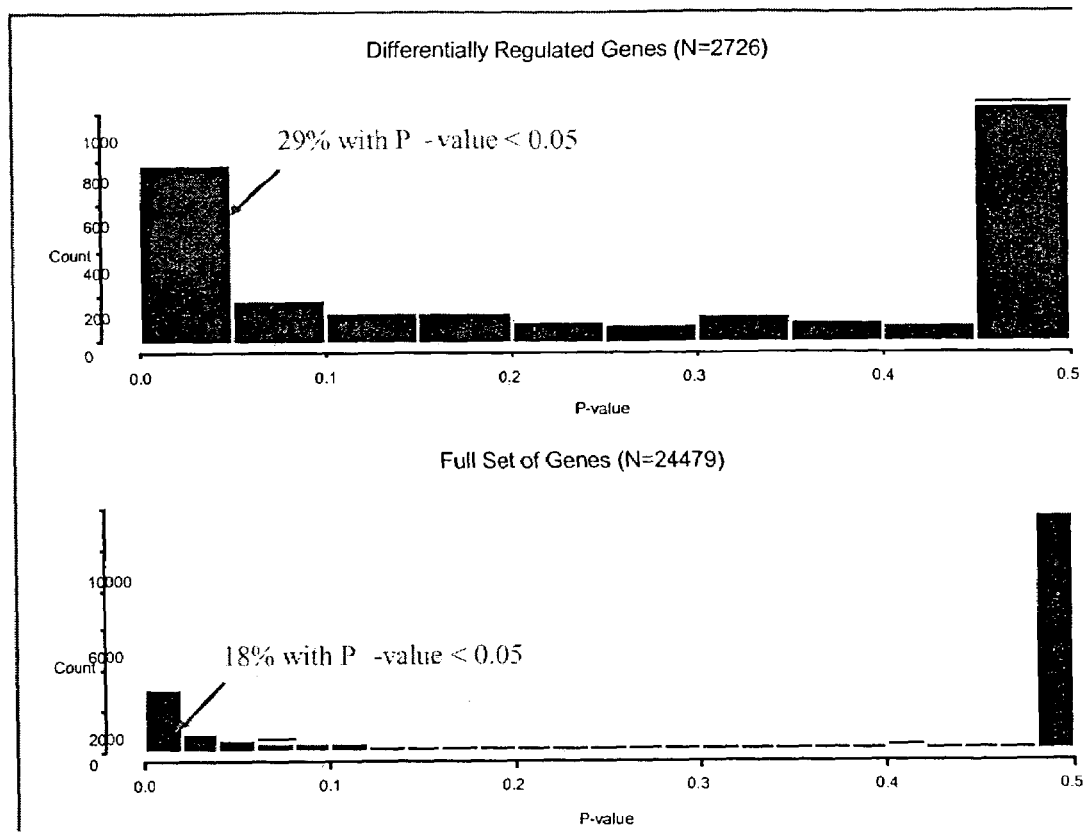

FIG. 13 provides a histogram for p-values of segregation analyses performed on 2,726 genes across 4 Ceph families in accordance with one embodiment of the present invention.

Like reference numerals refer to corresponding parts throughout the several views of the drawings.

5. DETAILED DESCRIPTION

The present invention provides an apparatus and method for associating a gene with a trait exhibited by one or more organisms in a plurality of organisms of a species.

Exemplary organisms include, but are not limited to, plants and animals. In specific embodiments, exemplary organisms include, but are not limited to plants such as corn, beans, rice, tobacco, potatoes, tomatoes, cucumbers, apple trees, orange trees, cabbage, lettuce, and wheat. In specific embodiments, exemplary organisms include, but are not limited to animals such as mammals, primates, humans, mice, rats, dogs, cats, chickens, horses, cows, pigs, and monkeys. In yet other specific embodiments, organisms include, but are not limited to, *Drosophila*, yeast, viruses, and *C. elegans*. In some instances, the gene is associated with the trait by identifying a biological pathway in which the gene product participates. In some embodiments of the present invention, the trait of interest is a complex trait such as a human disease. Exemplary human diseases include, but are not limited to, diabetes, cancer, asthma, schizophrenia, arthritis, multiple sclerosis, and rheumatosis. More information on complex traits is provided in Section 5.15, infra. In some embodiments, the trait of interest is a preclinical indicator of disease, such as, but not limited to, high blood pressure, abnormal triglyceride levels, abnormal cholesterol levels, or abnormal high-density lipoprotein/low-density lipoprotein levels. In a specific embodiment of the present invention, the trait is low resistance to an infection by a particular insect or pathogen. Additional exemplary diseases are found in Section 5.12, infra. In the invention, the levels of each cellular constituent in each of a plurality of organisms is transformed into a corresponding expression statistic. A "level of a cellular constituent" can be an expression level measurement of a gene that is determined by, for example, a level of its encoded RNA (or cDNA) or proteins or activity levels of encoded proteins. In some embodiments, this transformation is a normalization routine in which raw gene expression data is normalized to yield a mean log ratio, a log intensity, and a background-corrected intensity. Further, a genetic marker map 78 (FIG. 1) is constructed from a set of genetic markers associated with the plurality of organisms. Then, for each gene G in a plurality of genes expressed by an organism in the population, a quantitative trait locus (QTL) analysis is performed using the genetic marker map in order to produce QTL data. A set of expression statistics represents the quantitative trait used in each QTL analysis. QTL analyses are explained in greater detail, infra, in conjunction with FIG. 2, element 210. This set of expression statistics, for any given gene G, comprises an expression statistic for gene G, for each organism in the plurality of organisms. Next, the QTL data obtained from each QTL analysis is clustered to form a QTL interaction map. Identification of tightly clustered QTLs in the QTL interaction map helps to identify genes that are genetically interacting. This information, in turn, helps to elucidate biological pathways that are affected by complex traits, such as human disease. In some embodiments of the present invention, tightly clustered QTLs in the QTL interaction map are considered candidate pathway groups. These candidate pathway groups are subjected to multivariate analysis in order to verify whether the genes in the candidate pathway group affect a particular complex trait.

One embodiment of the present invention provides a method for associating a gene with a trait exhibited by one or more organisms in a plurality of organisms of a species. In the method, quantitative trait locus data from a plurality of quantitative trait locus analyses are clustered to form a quantitative trait locus interaction map. Each quantitative trait locus analysis in the plurality of quantitative trait locus analyses are performed for a gene G in a plurality of genes in the genome of the plurality of organisms using a genetic marker map and a quantitative trait in order to produce the quantitative trait locus data. For each quantitative trait locus analysis, the quantitative trait comprises an expression statistic for the gene G for which the quantitative trait locus analysis has been performed, for each organism in the plurality of organisms. The genetic marker map is constructed from a set of genetic markers associated with the plurality of organisms. Further, in the method, the quantitative trait locus interaction map is analyzed to identify a gene associated with a trait, thereby associating the gene with the trait exhibited by one or more organisms in the plurality of organisms.

5.1. Overview of the Invention

Figure 1:
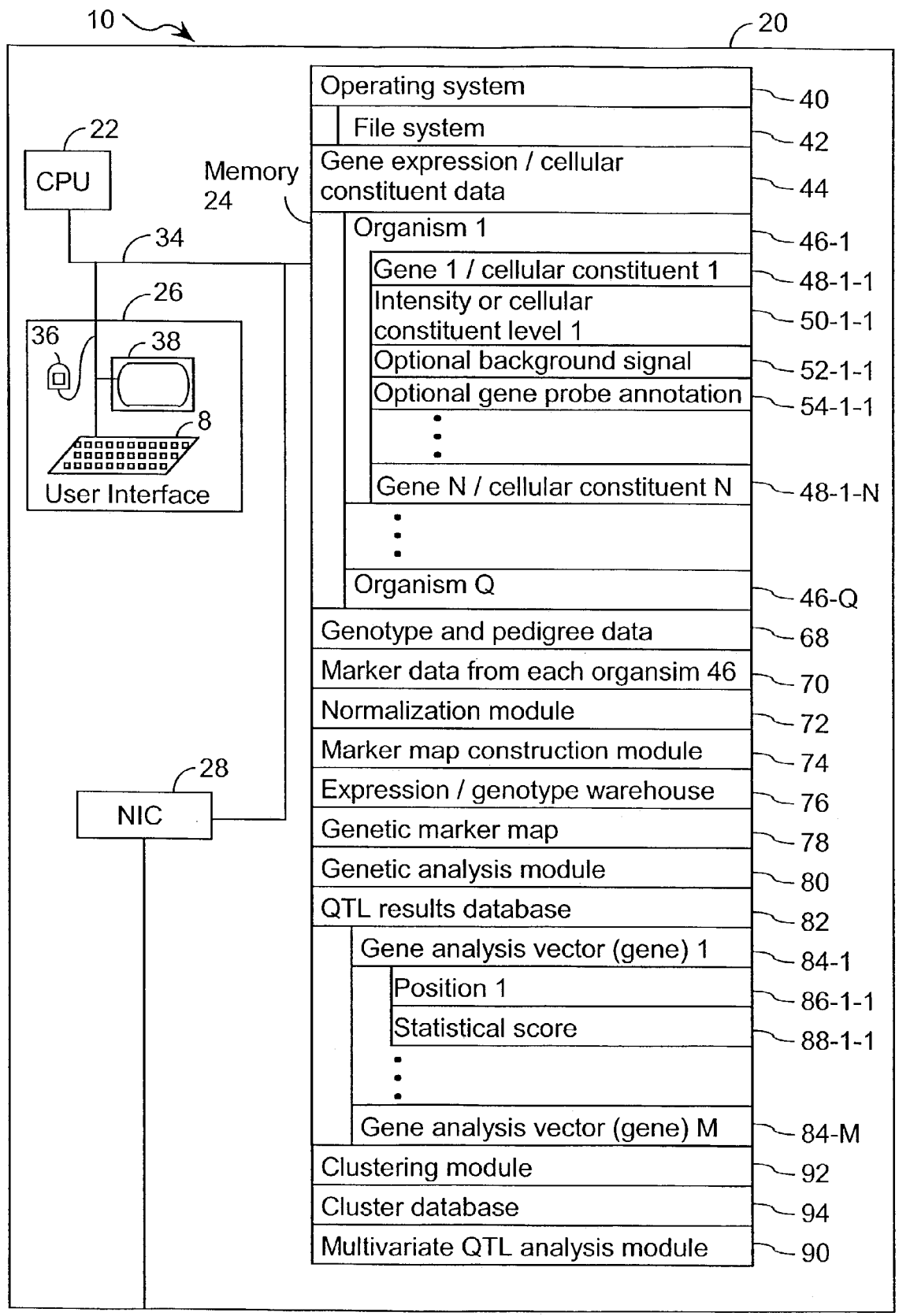
FIG. 1 illustrates a computer system for associating a gene with a trait exhibited by one or more organisms in a plurality of organisms in accordance with one embodiment of the present invention.
Figure 2:
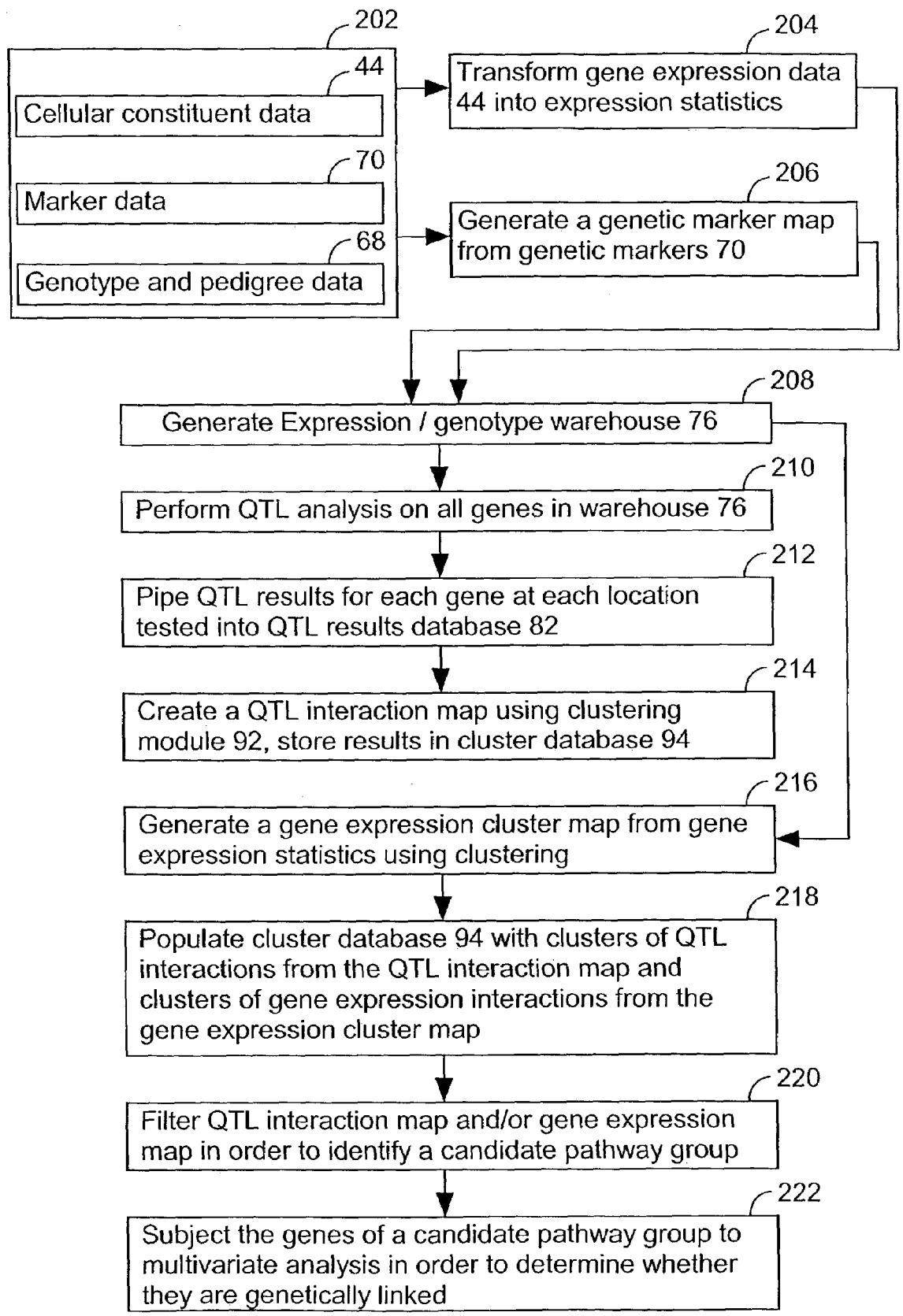
FIG. 2 illustrates processing steps in accordance with a preferred embodiment of the present invention.

FIG. 1 illustrates a system 10 that is operated in accordance with one embodiment of the present invention. In addition, FIG. 2 illustrates the processing steps that are performed in accordance with one embodiment of the present invention. These figures will be referenced in this section in order to disclose the advantages and features of the present invention. System 10 comprises at least one computer 20 (FIG. 1). Computer 20 comprises standard components including a central processing unit 22, memory 24 (including high speed random access memory as well as non-volatile storage, such as disk storage) for storing program modules and data structures, user input/output device 26, a network interface 28 for coupling server 20 to other computers via a communication network (not shown), and one or more busses 34 that interconnect these components. User input/output device 26 comprises one or more user input/output components such as a mouse 36, display 38, and keyboard 8.

Memory 24 comprises a number of modules and data structures that are used in accordance with the present invention. It will be appreciated that, at any one time during operation of the system, a portion of the modules and/or data structures stored in memory 24 is stored in random access memory while another portion of the modules and/or data structures is stored in non-volatile storage. In a typical embodiment, memory 24 comprises an operating system 40. Operating system 40 comprises procedures for handling various basic system services and for performing hardware dependent tasks. Memory 24 further comprises a file system 42 for file management. In some embodiments, file system 42 is a component of operating system 40.

Step 202. The present invention begins with cellular constituent data 44 (e g., from a gene expression study) and a genotype and/or pedigree data 68 from an experimental cross (in the case where humans are not used) or human cohort under study (FIG. 1; FIG. 2, step 202). In one embodiment, cellular constituent data 44 consists of the processed microarray images for each individual (organism) 46 in a population under study. In some embodiments, such data comprises, for each individual 46, intensity information 50 for each gene 48 represented on the microarray, background signal information 52, and associated annotation information 54 describing the gene probe (FIG. 1). In some embodiments, cellular constituent data is, in fact, protein levels for various proteins in the organisms under study. In one aspect of the present invention, the expression level of a gene in an organism in the population of interest is determined by measuring an amount of the corresponding at least one cellular constituent that corresponds to the gene in one or more cells of the organism. As used herein, the term "cellular constituent" comprises individual genes, proteins, mRNA expressing a gene, and/or any other variable cellular component or protein activities, degree of protein modification (e.g., phosphorylation), for example, that is typically measured in a biological experiment by those skilled in the art. Although, for ease of understanding the invention, the disclosure often makes reference to single cells, it will be understood by those of skill in the art that, more often, any particular step of the invention is carried out using a plurality of genetically similar cells, e.g., from a cultured cell line. Such similar cells are referred to herein as a "cell type." In one embodiment, the amount of the at least one cellular constituent that is measured comprises abundances of at least one RNA species present in one or more cells. Such abundances may be measured by a method comprising contacting a gene transcript array with RNA from one or more cells of the organism, or with cDNA derived therefrom. A gene transcript array comprises a surface with attached nucleic acids or nucleic acid mimics. The nucleic acids or nucleic acid mimics are capable of hybridizing with the RNA species or with cDNA derived from the RNA species. In some embodiments, cellular constituent data 44 is taken from tissues that have been associated with the complex trait under study. For example, in one non-limiting embodiment where the complex trait under study is human obesity, gene expression data is taken from liver, brain, or adipose tissues, to name a few.

In some embodiments of the present invention, cellular constituent data 44 is measured from multiple tissues of each organism 46 (FIG. 1) under study. For example, in some embodiments, cellular constituent data 44 is collected from one or more tissues selected from the group of liver, brain, heart, skeletal muscle, white adipose from one or more locations, and blood. In such embodiments, the data is stored in an exemplary data structure such as that disclosed in FIG. 3C. This data structure is described in more detail below.

Genotype and/or pedigree data 68 (FIG. 1) comprise the actual alleles for each genetic marker typed in each individual under study, in addition to the relationships between these individuals. The extent of the relationships between the individuals under study may be as simple as an $F_2$ population or as complicated as extended human family pedigrees. Exemplary sources of genotype and pedigree data are described in Section 6.1, infra. In some embodiments of the present invention, pedigree data is optional.

Marker data 70 at regular intervals across the genome under study or in gene regions of interest is used to monitor segregation or detect associations in a population of interest. Marker data 70 comprise those markers that will be used in the population under study to assess genotypes. In one embodiment, marker data 70 comprise the names of the markers, the type of markers (e.g., SNP, microsatellite, etc.), the physical and genetic location of the markers in the genomic sequence. Exemplary types of markers include, but are not limited to, restriction fragment length polymorphisms "RFLPs", random amplified polymorphic DNA "RAPDs", amplified fragment length polymorphisms "AFLPs", simple sequence repeats "SSRs", single nucleotide polymorphisms "SNPs", and microsatellites, etc. Further, in some embodiments, marker data 70 comprises the different alleles associated with each marker. For example, a particular microsatellite marker consisting of 'CA' repeats may have represented ten different alleles in the population under study, with each of the ten different alleles in turn consisting of some number of repeats. Representative marker data 70 in accordance with one embodiment of the present invention is found in Section 5.2, infra. In one embodiment of the present invention, the genetic markers used comprise single nucleotide polymorphisms (SNPs), microsatellite markers, restriction fragment length polymorphisms, short tandem repeats, DNA methylation markers, and/or sequence length polymorphisms.

Step 204. Once starting data are assembled, cellular constituent data 44 is transformed (FIG. 2, step 204) into expression statistics that are used to treat each gene transcript abundance in cellular constituent data 44 as a quantitative trait. In some embodiments, cellular constituent data 44 (FIG. 1) comprises gene expression data for a plurality of genes. In one embodiment, the plurality of genes comprises at least five genes. In another embodiment, the plurality of genes comprises at least one hundred genes, at least one thousand genes, at least twenty thousand genes, or more than thirty thousand genes. The expression statistics commonly used as quantitative traits in the analyses in one embodiment of the present invention include, but are not limited to, the mean log ratio, log intensity, and background-corrected intensity. In other embodiments, other types of expression statistics are used as quantitative traits. In one embodiment, this transformation (FIG. 2, step 204) is performed using normalization module 72 (FIG. 1). In such embodiments, the expression level of a plurality of genes in each organism under study are normalized. Any normalization routine may be used by normalization module 72. Representative normalization routines include, but are not limited to, Z-score of intensity, median intensity, log median intensity, Z-score standard deviation log of intensity, Z-score mean absolute deviation of log intensity calibration DNA gene set, user normalization gene set, ratio median intensity correction, and intensity background correction. Furthermore, combinations of normalization routines may be run. Exemplary normalization routines in accordance with the present invention are disclosed in more detail in Section 5.3, infra. The expression statistics formed from the transformation are then stored in Expression/genotype warehouse 76, where they are ultimately matched with the corresponding genotype information.

Step 206. In addition to the generation of expression statistics from cellular constituent data 44, a genetic marker map 78 is generated from genetic markers 70 (FIG. 1; FIG. 2, step 206). In one embodiment of the present invention, a genetic marker map is created using marker map construction module 74 (FIG. 1). Further, in one embodiment, genotype probability distributions for the individuals under study are computed. Genotype probability distributions take into account information such as marker information of parents, known genetic distances between markers, and estimated genetic distances between the markers. Computation of genotype probability distributions generally requires pedigree data. In some embodiments of the present invention, pedigree data is not provided and genotype probability distributions are not computed.

Step 208. Once the expression data has been transformed into corresponding expression statistics and genetic marker map 78 has been constructed, the data is transformed into a structure that associates all marker, genotype and expression data for input into QTL analysis software. This structure is stored in expression/genotype warehouse 76 (FIG. 1; FIG. 2, step 208).

Step 210. A quantitative trait locus (QTL) analysis is performed using data corresponding to each gene in a plurality of genes as a quantitative trait (FIG. 2, step 210). For 20,000 genes, this results in 20,000 separate QTL analyses. For embodiments in which multiple tissue samples are collected for each organism, this results in even more separate QTL analyses. For example, in embodiments in which samples are collected from two different tissues, an analysis of 20,000 genes requires 40,000 separate QTL analyses. In one embodiment, each QTL analysis is performed by genetic analysis module 80 (FIG. 1). In one example, each QTL analysis steps through each chromosome in the genome of the organism of interest. Linkages to the gene under consideration are tested at each step or location along the length of the chromosome. In such embodiments, each step or location along the length of the chromosome can be at regularly defined intervals. In some embodiments, these regularly defined intervals are defined in Morgans or, more typically, centiMorgans (cM). A Morgan is a unit that expresses the genetic distance between markers on a chromosome. A Morgan is defined as the distance on a chromosome in which one recombinational event is expected to occur per gamete per generation. In some embodiments, each regularly defined interval is less than 100 cM. In other embodiments, each regularly defined interval is less than 10 cM, less than 5 cM, or less than 2.5 cM.

Figure 3A:
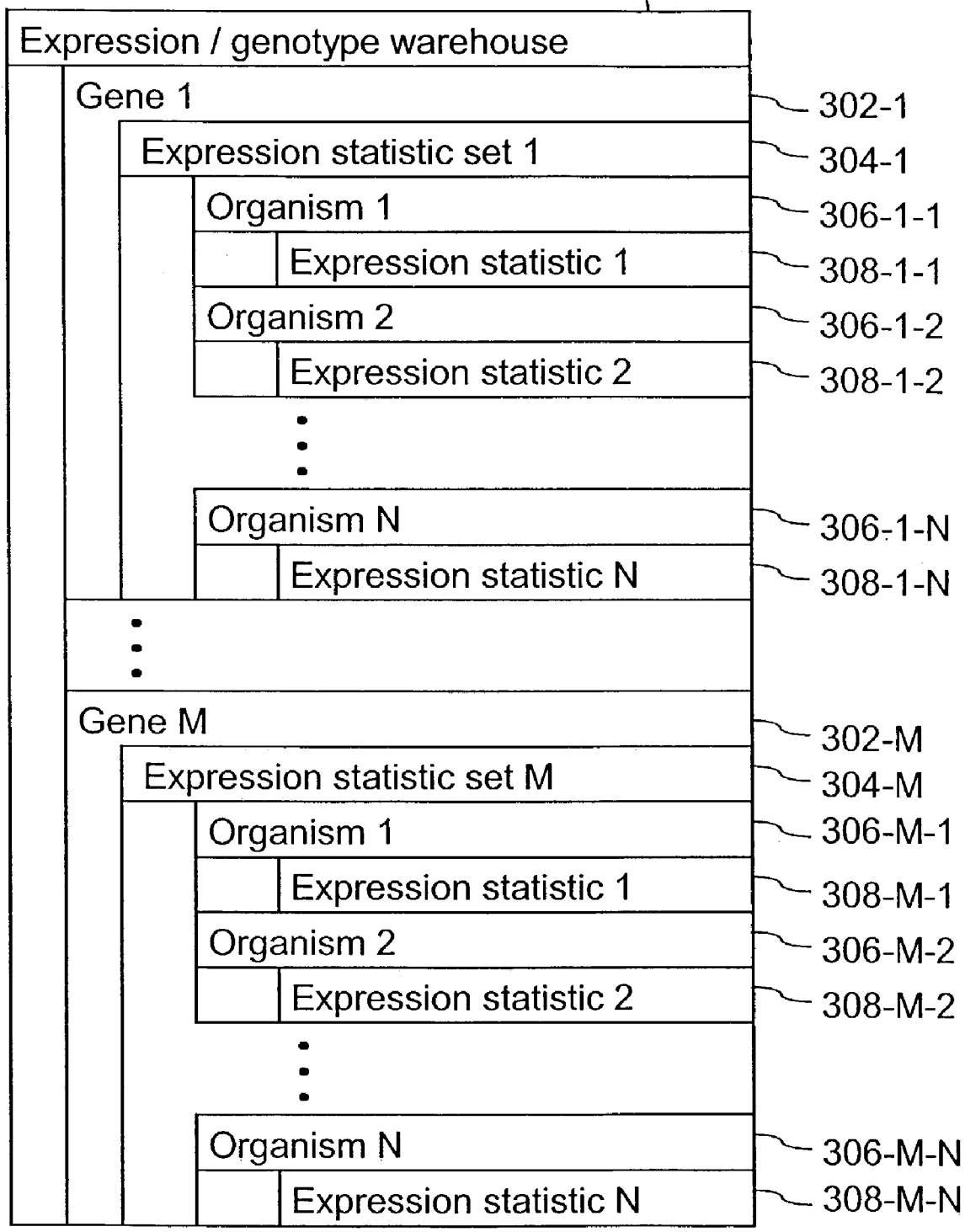
FIG. 3A illustrates an expression/genotype warehouse in accordance with one embodiment of the present invention.
Figure 3B:
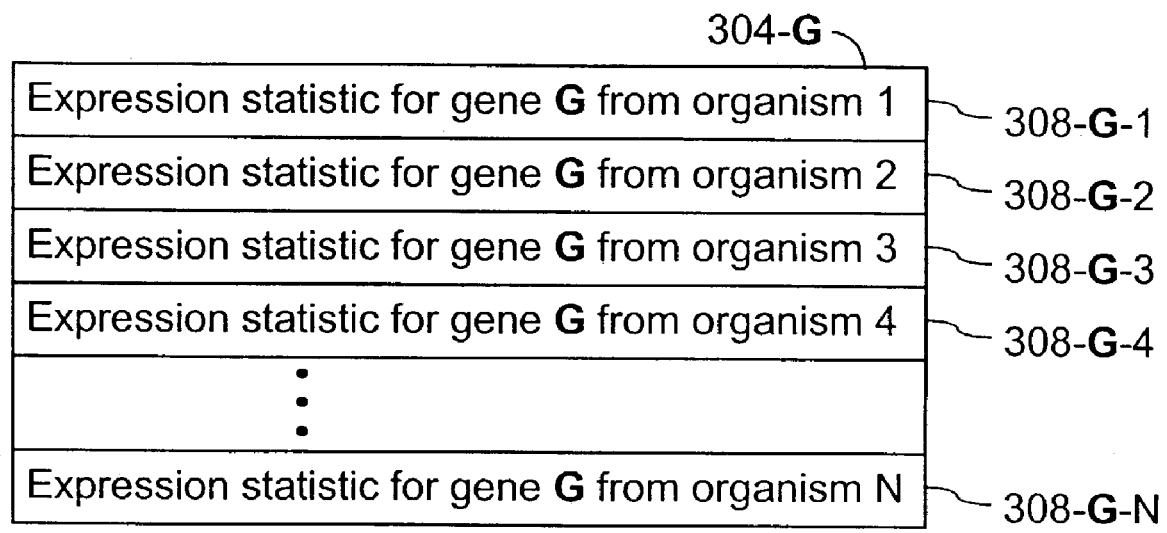
FIG. 3B illustrates a gene expression statistic found in an expression/genotype warehouse in accordance with one embodiment of the present invention.

In each QTL analysis, data corresponding to the expression level of a gene in the plurality of organisms under study is used as a quantitative trait. More specifically, for any given gene, the quantitative trait used in the QTL analysis is an expression statistic set such as set 304 (FIG. 3A). Expression statistic set 304 comprises the corresponding expression statistic 308 for the gene 302 from all or a portion of the organisms 306 in the population under study. FIG. 3B illustrates an exemplary expression statistic set 304 in accordance with one embodiment of the present invention. Exemplary expression statistic set 304 includes the expression level 308 of a gene G (or cellular constituent that corresponds to gene G) from each organism in a plurality of organisms. For example, consider the case where there are ten organisms in the plurality of organisms, and each of the ten organisms expresses gene G. In this case, expression statistic set 304 includes ten entries, each entry corresponding to a different one of the ten organisms in the plurality of organisms. Further, each entry represents the expression level of gene G (or a cellular constituent corresponding to gene G) in the organism represented by the entry. So, entry "1" (308-G-1) corresponds to the expression level of gene G (or a cellular constituent corresponding to gene G) in organism 1, entry "2" (308-G-2) corresponds to the expression level of gene G (or a cellular constituent corresponding to gene G) in organism 2, and so forth.

Figure 3C:
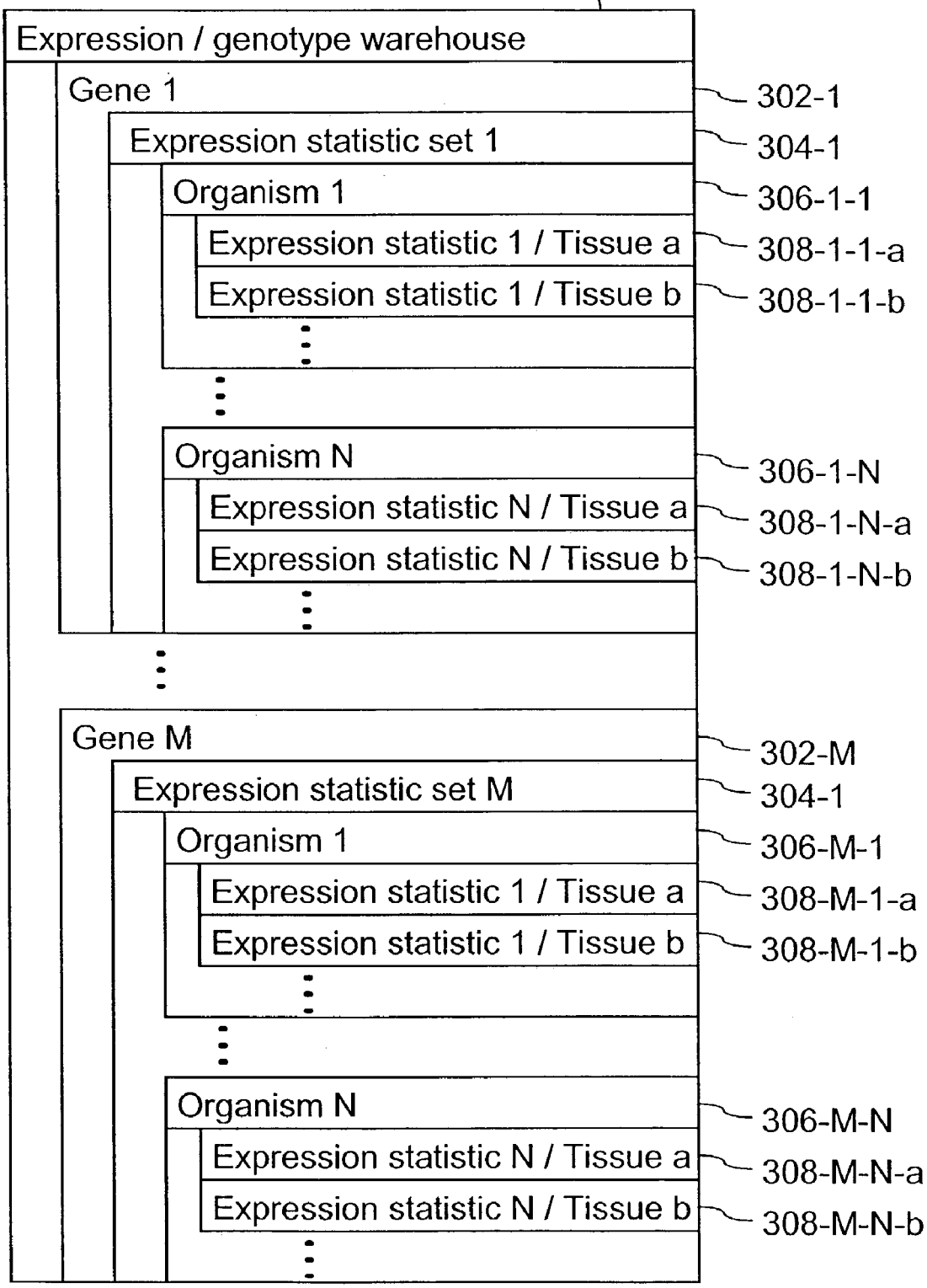
FIG. 3C illustrates an expression/genotype warehouse in accordance with another embodiment of the present invention.

Referring to FIG. 3C, in some embodiments of the present invention, expression data from multiple tissue samples of each organism 306 (FIG. 1, 46) under study are collected. When this is the case, the data can be stored in the exemplary data structure illustrated in FIG. 3C. In FIG. 3C, a plurality of genes 302 are represented. Further, there is an expression statistic set 304 for each gene 302. Each expression statistic set 304 represents the expression level (308) of the gene or an abundance of a cellular constituent (308) that corresponds to the gene in each of a plurality of organisms 306 (FIG. 1, 46). In one example, a cellular constituent is a particular protein and the cellular constituent corresponds to a gene when the gene codes for the cellular constituent.

In one embodiment of the present invention, each QTL analysis (FIG. 2, step 210) comprises: (i) testing for linkage between a position in a chromosome and the quantitative trait (e.g., expression values for a particular gene in each organism in a plurality of organisms) used in the quantitative trait locus (QTL) analysis, (ii) advancing the position in the chromosome by an amount, and (iii) repeating steps (i) and (ii) until the end of the chromosome is reached. In typical embodiments, the quantitative trait is an expression statistic set 304, such as the set illustrated in FIG. 3B. In some embodiments, testing for linkage between a given position in the chromosome and the expression statistic set 304 comprises correlating differences in the expression levels found in the expression level statistic 304 with differences in the genotype at the given position using a single marker test. Examples of single marker tests include, but are not limited to, t-tests, analysis of variance, or simple linear regression statistics. See, e.g., *Statistical Methods*, Snedecor and Cochran, 1985, Iowa State University Press, Ames, Iowa. However, there are many other methods for testing for linkage between expression statistic set 304 and a given position in the chromosome. In particular, if expression statistic set 304 is treated as the phenotype (in this case, a quantitative phenotype), then methods such as those disclosed in Doerge, 2002, Mapping and analysis of quantitative trait loci in experimental populations, *Nature Reviews: Genetics* 3:43–62, may be used. Concerning steps (i) through (iii) above, if the genetic length of a given chromosome is N cM and 1 cM steps are used, then N different tests for linkage are performed on the given chromosome. For organisms having multiple chromosomes, this process is repeated for each chromosome in the genome.

In some embodiments, the QTL data produced from each respective QTL analysis comprises a logarithmic of the odds score (LOD) computed at each position tested in the genome under study. A LOD score is a statistical estimate of whether two loci are likely to lie near each other on a chromosome and are therefore likely to be genetically linked. In the present case, a LOD score is a statistical estimate of whether a given position in the genome under study is linked to the quantitative trait corresponding to a given gene. LOD scores are further defined in Section 5.4, infra. Generally, a LOD score of three or more suggests that two loci are genetically linked, a LOD score of four or more is strong evidence that two loci are genetically linked, and a LOD score of five or more is very strong evidence that two loci are genetically linked. However, the significance of any given LOD score actually varies from species to species depending on the model used. The generation of LOD scores requires pedigree data. Accordingly, in embodiments in which a LOD score is generated, processing step 210 is essentially a linkage analysis, as described in Section 5.13, below.

In situations where pedigree data is not available, genotype data from each of the organisms 46 (FIG. 1) for each marker in genetic marker map 70 can be compared to each quantitative trait (expression statistic set 304) using allelic association analysis, as described in Section 5.14, infra, in order to identify QTL that are linked to each expression statistic 304. In one form of association analysis, an affected population is compared to a control population. In particular, haplotype or allelic frequencies in the affected population are compared to haplotype or allelic frequencies in a control population in order to determine whether particular haplotypes or alleles occur at significantly higher frequency amongst affected samples compared with control samples. Statistical tests such as a chi-square test are used to determine whether there are differences in allele or genotype distributions.

Step 212. Regardless of whether linkage analysis, association analysis, or some combination thereof is used in step 210, the results of each QTL analysis are stored in QTL results database 82 (FIG. 1; FIG. 2, step 212). For each quantitative trait 84 (expression statistic 304), QTL results database 82 comprises all positions 86 in the genome of the organism that were tested for linkage to the quantitative trait 84. Positions 86 are obtained from genetic marker map 70. Further, for each position 86, genotype data 68 provides the genotype at position 86, for each organism in the plurality of organisms under study. For each such position 86 analyzed by QTL analysis, a statistical measures (e.g., statistical score 88), such as the maximum LOD score between the position and the quantitative trait 84, is listed. In the case where LOD scores are used, there is a LOD score for the entire population tested as well as individual LOD scores for each of the individuals under study. Thus, data structure 82 comprises all the positions in the genome of the organism of interest that are genetically linked to each quantitative trait 84 tested.

Figure 4:
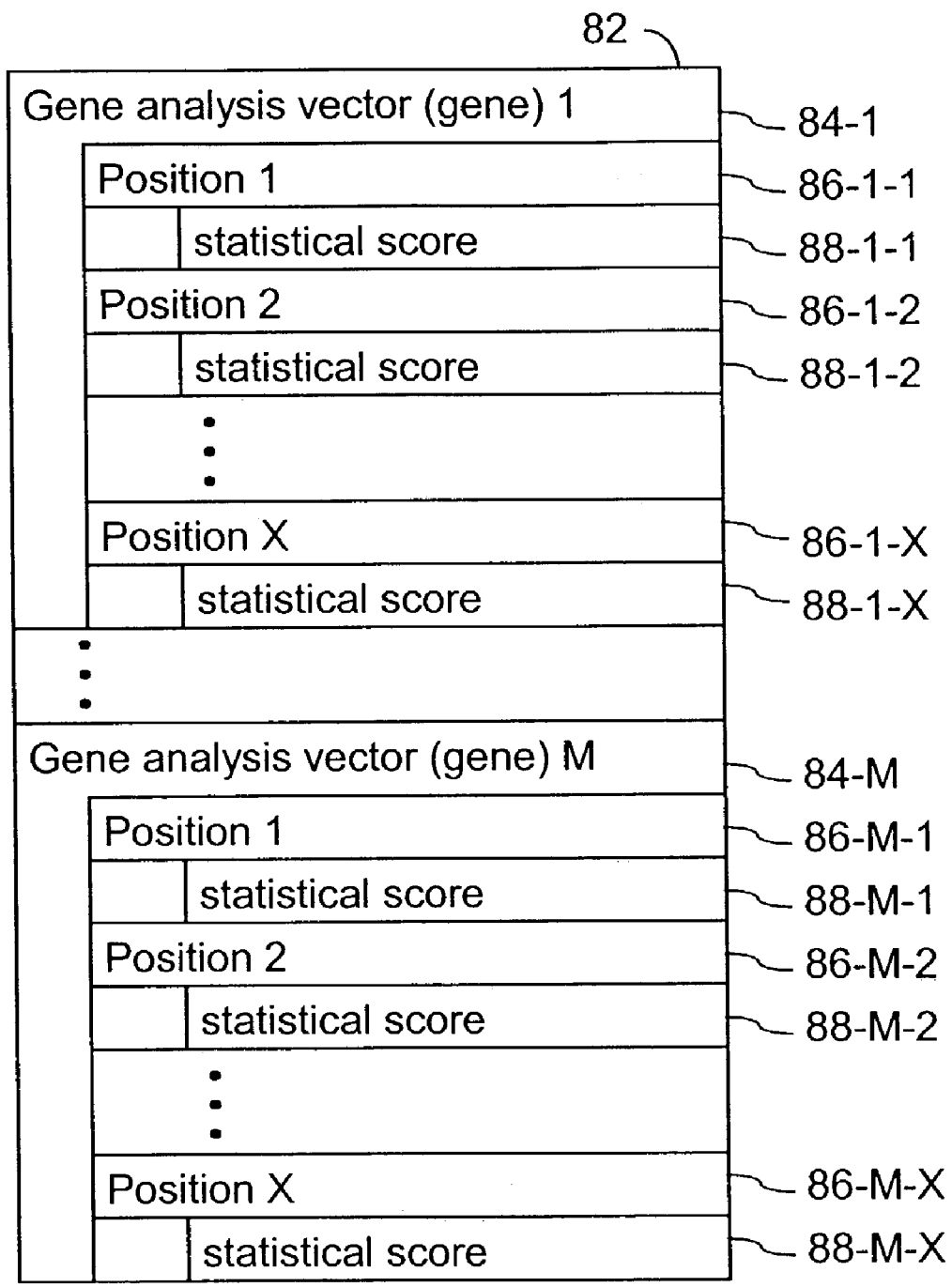
FIG. 4 illustrates quantitative trait locus results database in accordance with one embodiment of the present invention.

FIG. 4 provides a more detailed illustration of QTL results database 82. Each statistical score 88 (e.g., LOD scores) measures the degree to which a given position 86 in the chromosome of the organisms/individuals under study is linked to the corresponding trait 84 (e.g., expression statistic set 304). Additionally, the statistical scores for each individual (i.e., the sum of these statistical scores gives the overall statistical score for a given position) for each cellular constituent is also stored, since these values are used to determine the extent of genetic interaction. FIG. 11 provides a plot that demonstrates the type of information captured. Plotted along the x-axis are centiMorgan positions along chromosome 5 in the *Zea mays* genome. Plotted along the y-axis are the LOD scores for two gene expression traits measured across 76 ear-leaf tissues from *Zea mays*. In this case, the regions of linkage to these traits are perfectly coincident, which is mainly due to the high degree of correlation between these two traits with respect to the expression values measured in 76 ear-leaf tissues from *Zea mays*. In this case, it is noted that the genes themselves fall at locations in the genome that are coincident with the QTL, indicating interaction between the two genes at the genetic level.

The set of statistical scores 88 for any given quantitative trait 84 can be considered (can be viewed as) a gene analysis vector. Thus, in some embodiments of the present invention, a gene analysis vector is created for each gene tested in the chromosome of the organism studied. Each element of the gene analysis vector is a statistical score (e.g., LOD score) at a different position in the genome of the species under study. In some embodiments in which gene expression/cellular constituent data 44 is collected from multiple tissue samples in each organism under study, a separate gene analysis vector is created for each tissue type from which data 44 was collected. For example, consider the case in which data 44 (FIG. 1) is collected from two different tissue type types from each organism 46 under study. In such embodiments, two gene analysis vectors are created for each cellular constituent (e.g., gene, protein) 48 tested. The first gene analysis vector for a given gene/cellular constituent 48 corresponds to one tissue type sample and the second gene analysis vector for the given gene/cellular constituent 48 corresponds to the second tissue type sampled. Thus, in effect, in some embodiments in which data from multiple tissues is collected, the data from each tissue type is treated for purposes of processing steps 202 through 220 as if the data were collected from independent organisms. However, in step 222, the data from multiple tissues types is optionally compared in order to determine the effect that tissue type has on the linkage analysis. Methods that incorporate data from multiple tissue types are described in more detail in conjunction with step 222 below as well as Section 5.6, below.

In some embodiments, a gene analysis vector 84 is created for each gene tested in the entire genome of the organisms studied. Thus, if there are 1000 genes tested, there will be 1000 gene analysis vectors 84. Each gene analysis vector 84 comprises the statistical score 88 at each chromosomal position 86 tested by the quantitative trait locus (QTL) analysis corresponding to the gene.

In addition to gene analysis vectors 84, gene expression vectors may be constructed from transformed gene expression data 44. Each gene expression vector represents the transformed expression level of the gene from each organism in the population of interest. Thus, any given gene expression vector 304 comprises the transformed expression level of the gene from a plurality of different organisms in the population of interest. Thus, a gene expression vector is simply an expression statistic set 304 for a given gene 302 as illustrated, for example, in FIG. 3A.

Step 214. With the gene analysis vectors generated, the next step of the present invention involves the generation of QTL interaction maps from the gene analysis vectors (FIG. 2, step 214). Step 214 is of interest because a goal of the present invention is to see which genes in the organisms under study are being regulated or regulate the same chromosomal regions. A gene analysis vector 84 tracks the QTL for the gene corresponding to the vector 84. As the term is used here, a QTL is a position 86 within a gene analysis vector 84 having a statistical score 88 that is indicative of a correlation between (i) the expression pattern of the gene in the plurality of organisms and (ii) the genotype (variation in the genome across the organisms) at the position 86 in the plurality of organisms. For example, in the case where statistical scores 88 are LOD scores, positions 86 that receive significant LOD scores are QTL. A QTL interaction map clusters those genes that tend to have QTL at the same positions 86.

In some embodiments of the present invention, QTL interaction maps are generated by clustering module 92. In embodiments in which gene analysis vectors 84 are generated from several different tissue types, the gene analysis vectors 84 from the various tissue types are clustered since gene expression in one tissue may drive expression in another tissue. In some embodiments, QTL representing diverse tissue types are clustered. In other words, in the case where there are two or more gene expression vectors 84 for the same gene but from different tissues, each the vectors are treated completely independently of each other as if they were from different organisms.

Gene analysis vectors 84 will cluster into the same group if the statistical scores 88 in such vectors are correlated. To illustrate, consider hypothetical gene analysis vectors 84 that were generated by performing QTL analysis against various QTL (e.g., various expression statistic sets 304) at five different chromosomal positions. Such vectors 84 will have five values. Each of the five values will be a statistical score 88 that represents a QTL analysis at one of the five chromosomal positions:

| | | | | | |
|---|---|---|---|---|---|
| Exemplary gene analysis vector 84-1: | {0, | 5, | 5.5, | 0, | 0} |
| Exemplary gene analysis vector 84-2: | {0, | 4.9, | 5.4, | 0, | 0} |
| Exemplary gene analysis vector 84-3: | {6, | 0, | 3, | 3, | 5} |

Clustering of exemplary gene analysis vectors 84-1, 84-2 and 84-3 will result in two clusters. The first cluster will include vectors 84-1 and 84-2 because there is a correlation in the statistical scores 88 within each vector (0 vs. 0 at chromosomal position 1, 5 vs. 4.9 at chromosomal position 2, 5.5 vs. 5.4 at chromosomal position 3, 0 vs. 0 at chromosomal position 4, and 0 vs. 0 at chromosomal position 5). The second cluster will include exemplary vector 84-3 because the pattern of the scores 88 in vector 84-3 is not similar to the pattern of the scores 88 in vectors 84-1 and 84-2. Now consider the case in which the hypothetical values reported for exemplary gene analysis vectors 84-1, 84-2, and 84-3 are LOD scores. It is evident that there is a significant QTL at positions 2 and 3 in vectors 84-1 and 84-2. However, vector 84-3 does not have a significant QTL at positions 2 and 3. Rather, vector 84-3 has a significant QTL at positions 1 and 5. Accordingly, vector 84-3 should not cocluster with vectors 84-1 and 84-2.

In one embodiment of the present invention, agglomerative hierarchical clustering is applied to gene analysis vectors 84. In this clustering, similarity is determined using Pearson correlation coefficients between the gene analysis vectors pairs. In other embodiments, the clustering of the QTL data from each QTL analysis comprises application of a hierarchical clustering technique, application of a k-means technique, application of a fuzzy k-means technique, application of a Jarvis-Patrick clustering technique, or application of a self-organizing map or application of a neural network. In some embodiments, the hierarchical clustering technique is an agglomerative clustering procedure. In other embodiments, the agglomerative clustering procedure is a nearest-neighbor algorithm, a farthest-neighbor algorithm, an average linkage algorithm, a centroid algorithm, or a sum-of-squares algorithm. In still other embodiments, the hierarchical clustering technique is a divisive clustering procedure. Illustrative clustering techniques that may be used to cluster gene analysis vectors are described in Section 5.5, infra. In preferred embodiments, nonparamatric clustering algorithms are applied to gene analysis vectors 84. In some embodiments, Spearman R, Kendall Tau, or Gamma coefficients are used to cluster gene analysis vectors 84.

Step 216. Advantageously, some aspects of the present invention combine the information derived from QTL interaction maps with gene expression data to help elucidate biological pathways that affect complex traits. In one embodiment of the present invention, a gene expression cluster map is constructed from cellular constituent level statistics (FIG. 2, step 216). A plurality of gene expression vectors are created. Each gene expression vector in the plurality of gene expression vectors represents the expression level, activity, or degree of modification of a particular cellular constituent, such as a gene or gene product, in each organism in the population of interest. In essence, each gene expression vector is a expression statistic set 304 for a given gene 302 as illustrated, for example, in FIG. 3A. A plurality of correlation coefficients are computed. Each correlation coefficient in the plurality of correlation coefficients described a correlation between a gene expression vector pair in the plurality of gene expression vectors. A gene expression vector pair are any two expression statistic sets 304. Then, the plurality of gene expression vectors are clustered based on the plurality of correlation coefficients in order to form the gene expression cluster map.

To illustrate the process of generating a gene expression vector clustering step as performed in step 216 of FIG. 2, consider the values of the three hypothetical gene expression vectors (expression statistic sets 304):

| | |
|---|---|
| Exemplary expression vector 304-1: | {1000, 100, 1000, 100, 1000} |
| Exemplary expression vector 304-2: | {1100, 120, 1100, 120, 1100} |
| Exemplary expression vector 304-3: | {100, 1200, 10100, 1020, 0} |

In this instance, expression vectors 304-1 and 304-2 will cocluster while expression vector 304-3 will form a separate cluster. Expression vectors 304-1 and 304-2 will cocluster because there is a correlation between the expression statistics 308 in the two vectors (1000 vs. 1100, 100 vs 120, 1000 vs 1100, 100 vs. 120, 1000 vs. 1100). Expression vectors 304-1 and 304-3 will not cocluster (will have a low correlation coefficient) because there is little if any correlation between the expression statistics 308 in the two vectors (1000 vs. 100, 100 vs. 1200, 1000 vs 10100, 100 vs. 1020, and 1000 vs. 0).

In one embodiment of the present invention, each correlation coefficient in the plurality of correlation coefficients computed in step 216 is a Pearson correlation coefficient. In another embodiment of the present invention, clustering of the plurality of gene expression vectors comprises application of a hierarchical clustering technique, application of a k-means technique, application of a fuzzy k-means technique, application of a self-organizing map or application of a neural network. In one embodiment of the present invention, the hierarchical clustering technique is an agglomerative clustering procedure such as a nearest-neighbor algorithm, a farthest-neighbor algorithm, an average linkage algorithm, a centroid algorithm, or a sum of squares algorithm. In another embodiment of the invention, the hierarchical clustering technique is a divisive clustering procedure. Illustrative clustering techniques that may be used to cluster the gene expression vectors are described in Section 5.5, infra. In some embodiments, nonparametric methods are used to cluster expression vector 304.

Step 218. In one embodiment of the present invention, clusters of QTL interactions from the QTL interaction maps (step 214) and clusters of gene expression interactions from the gene expression cluster maps (step 216) are represented in cluster database 94 (FIG. 1; FIG. 2, step 218). In some embodiments, cluster database 94 is used to identify the patterns that feed a multivariate QTL analyses. In addition to the gene analysis vector and gene expression vector cluster information, the physical locations of the QTLs and genes are represented in cluster database 94. Cluster database 94 is used as a basis for comparing QTL interaction maps to gene expression cluster maps.

Figure 5:
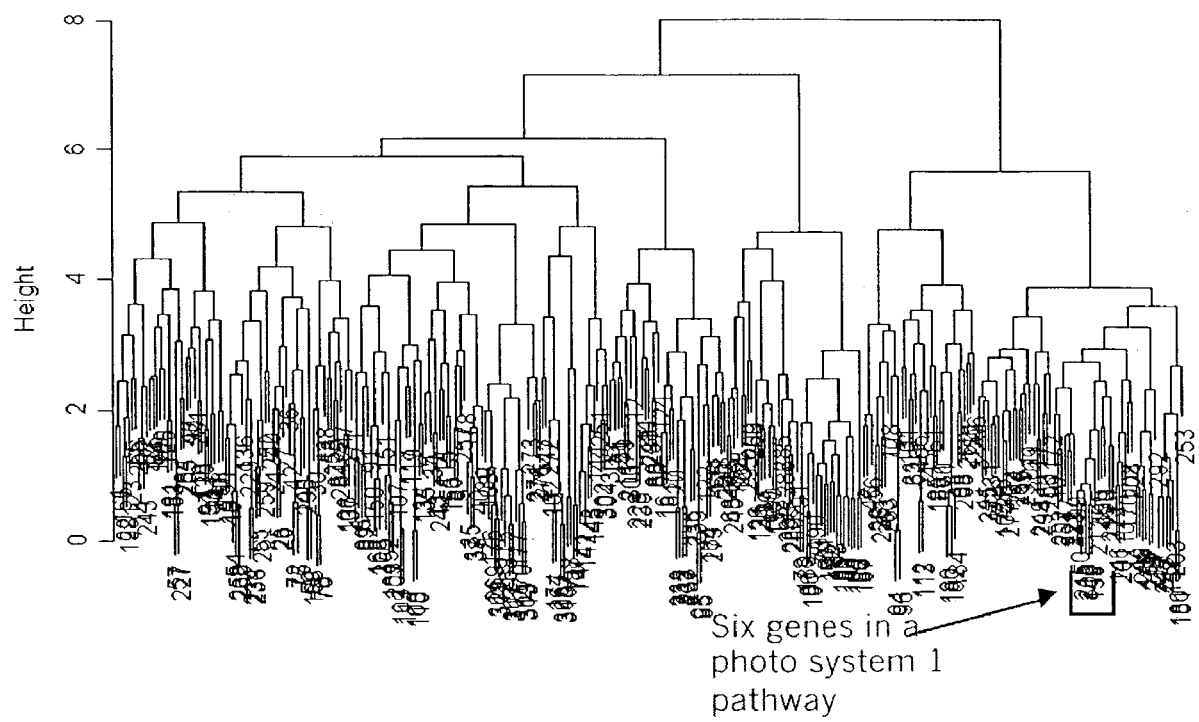
FIG. 5 illustrates an exemplary quantitative trait locus interaction map.
Figure 6:
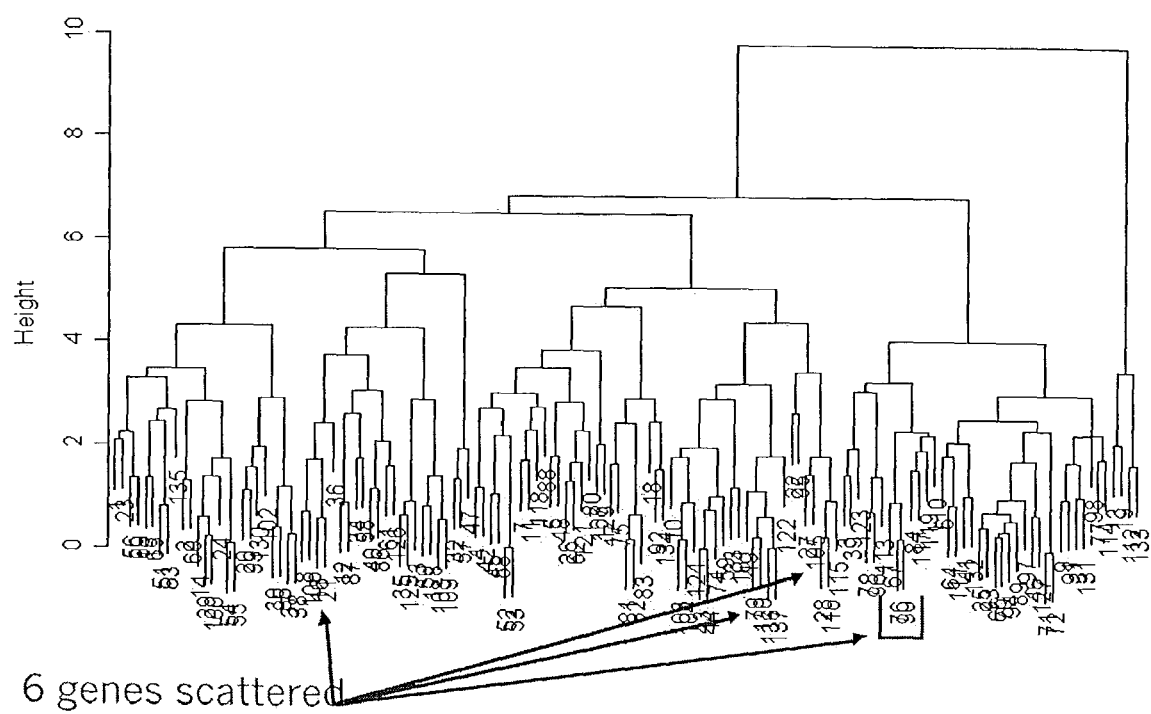
FIG. 6 illustrates an exemplary gene expression cluster map.

FIGS. 5 and 6 show the utility of comparing a QTL interaction map (FIG. 5) to a gene expression cluster map (FIG. 6). FIG. 5 illustrates a QTL interaction map for *Zea mays* gene analysis vectors in which a group of six genes known to be involved in the photo system one pathway are clustered closely together. FIG. 6 illustrates a gene expression cluster map for the same organism. The genes labeled in FIG. 6 are the same as the genes labeled in FIG. 5. As can be seen by comparison of FIG. 5 to FIG. 6, the genes of the photo system 1 pathway do not group together based on expression, even though they are grouped together genetically.

Construction of hierarchical clusters that integrate QTL interaction and gene expression interaction data helps to identify genes that are under common genetic control, but do not have correlated expression values. This point is illustrated with FIGS. 7 and 8. FIG. 7 plots the expression values for one gene along the x-axis and the expression values for another gene along the y-axis, over 76 ear-leaf tissues from *Zea mays*. These two genes have coincident QTL, and the very strong linear correlation between the expression values for these two genes explains the coincident QTL, given the gene expression values for each gene provide the same information. FIG. 8 also plots the expression values for one gene along the x-axis and the expression values for another gene along the y-axis, over 76 ear-leaf tissues from *Zea mays*. However, unlike FIG. 7, the expression values between the two genes are not correlated in FIG. 8. While the two genes plotted in FIG. 8 have coincident QTL, the two major QTL for each gene are strongly interacting, suggesting these genes are under similar genetic control. This information could not be discerned by looking at the expression patterns alone or by looking at the genotypes or more classic information alone. However, when such information is considered together, the information provides a powerful mechanism for elucidating biological pathways.

Step 220. The QTL interaction map produced in step 214 provides information on the genetic linkage between individual genes in the organisms under study. Genes represented by gene analysis vectors 84 that cluster together in the QTL interaction map are potentially regulated by the same chromosomal positions and/or affect genes in the same chromosomal positions. Thus, the QTL interaction map produced in step 214 can be used to define the identity or refine the identity of a candidate pathway group. In one embodiment, a candidate pathway group is a set of genes that are members of a biological pathway that affect a complex trait. In another embodiment, a candidate pathway group is simply a set of genes that affect a complex trait. Such genes may be genetically linked to each other.

In step 220, the QTL interaction map and/or the gene expression cluster map is filtered in order to identify one or more candidate pathway groups. In some embodiments, the step of filtering the QTL interaction map in order to identify a candidate pathway group comprises designating the genes corresponding to the gene analysis vectors 84 that form a cluster in the QTL interaction map as a candidate pathway group.

In some embodiments of the present invention, the candidate pathway group that is defined as the genes corresponding to the gene analysis vectors 84 that form a cluster in the QTL interaction map is further refined using the gene expression cluster map. In this further refinement, those genes in the candidate pathway group that also cluster in the gene expression cluster map are removed from the candidate cluster group. While not intending to be limited to any particular theory, a rational for this refinement is that the genes that cocluster in the gene expression cluster map tend to represent downstream participants in a biological pathway rather than potentially more interesting upstream participants.

To illustrate step 220, in one embodiment, gene analysis vectors 84-1, 84-5, 84-10, 84-12, and 84-20 through 84-100 cocluster together in the QTL interaction map. Thus, the gene (cellular constituent 48, FIG. 1; gene 302, FIG. 3C) represented by vector 84-1, the gene (cellular constituent 48, FIG. 1; gene 302, FIG. 3C) represented by vector 84-5, the gene (cellular constituent 48, FIG. 1; gene 302, FIG. 3C) represented by vector 84-10 and so forth define a candidate pathway group. This, in itself, is a significant result. The result indicates that this set of genes could be a biological pathway that affects a complex trait. However, the group as it stands includes 85 genes. A multivariate analysis of the expression pattern of eighty five genes is undesirably complex. Therefore, in order to reduce the number of genes in the candidate pathway group, the gene expression cluster map from step 216 can be used to reduce the number of genes in the candidate pathway group. For the sake of example, consider the case in which the genes represented by gene analysis vectors 84-21 through 84-100 cocluster together in the gene expression cluster map. In one embodiment, therefore, the genes represented by gene analysis vectors 84-21 through 84-100 are removed from the candidate pathway group. Thus, after refinement, the candidate pathway group leaves the gene represented by vector 84-1, 84-5, 84-10, 84-12, and 84-20 in the candidate pathway group. Thus, the candidate pathway group is reduced from 85 genes to a set of five genes. Advantageously, this set of five genes can be subjected to multivariate analysis in order to determine whether the variance in expression patterns in the set of genes, considered collectively, yield QTL within the genome of the species under study that have statistically significantly higher LOD scores than when the set of genes are considered independently. If such higher LOD scores are found when the set of genes is considered collectively, this indicates that the set of genes are genetically interacting in some form of genetic pathway.

In alternative embodiments, gene expression clusters found in gene expression cluster maps (step 216) (rather than QTL interaction maps) can each be considered to be in the same candidate pathway group. In such embodiments, the QTL interaction map (step 214) can be used to identify those genes that are "closer" together in the candidate pathway group than other genes in the candidate pathway group. That is, genes that cocluster in both the gene interaction map (expression data) and the QTL interaction map (QTL linkage data) can be identified as genes that are "closer" together in a candidate pathway group.

In some embodiments, genes in gene expression clusters (step 216) found in a gene expression map that are not at all genetically interacting (as indicated by the QTL interaction map) may be down-weighted with respect to those genes that are genetically interacting. In this way, the QTL interaction map helps to refine candidate pathway groups that are identified in gene expression cluster maps.

In some embodiments of the present invention, the method further comprises determining a clinical trait associated with the biological pathway. This clinical trait represents a phenotype that is measured or is measurable in a plurality of organisms. There are many ways in which such a clinical trait can be associated with a biological pathway. In some embodiments, it is accomplished by treating the clinical trait (e.g., a disease state, eye color, level of a compound in the blood, an clinical obesity measurement) as if it were a gene expression vector 304. The only difference is that, rather than providing an expression statistic 308 from each organism 306 (FIG. 3A) a quantitative value representing a measurement of the clinical trait in each organism 306 is provided. In this way, quantitative trait analysis (e.g., linkage analysis, association analysis, or some combination thereof) can be used to generate a gene analysis vector 84 for the clinical trait. The gene analysis vector 84 for the clinical trait can then be used in a variety of ways to determine whether the candidate pathway group is genetically linked to the clinical trait. In one approach, the gene analysis vector 84 for the clinical trait is coclustered with all the other gene analysis vectors 84. If the QTL pattern within the gene analysis vector 84 for the clinical trait corresponds to the QTL pattern for each of the gene analysis vectors 84 that represent genes in the candidate pathway group, then the gene analysis vector 84 for the clinical trait will cocluster with these vector 84. Such coclustering (colocalization of QTL/coclustering of genes) would indicate that the clinical trait is genetically linked to the genes the comprise the candidate pathway group. In another approach, the genes in a candidate pathway group can be associated with a biological pathway be reviewing annotation information for each of the genes in the candidate pathway group. Such annotation information can be found in publically available gene sequence data database, protein sequence database, as well as journal reports.

Step 222. Despite the many uses of the QTL interaction map that are described above, the QTL interaction map does not provide the actual topology of candidate pathway groups. An illustrative topology of a pathway group (biological pathway) can be, for example, that gene A is upstream of gene B. Another drawback of the QTL interaction map (step 214) that is not interpreted in light of gene expression cluster map (step 216) is that the QTL interaction map may include false positives. For example, a cluster within the QTL interaction map can include genes that do not interact genetically. To shed light on the topology of biological pathways associated with complex diseases, as well as to eliminate false positive genes, processing step 222 is performed.

In one embodiment of step 222, a pathway group is validated by fitting the candidate pathway group to genetic models in order to test whether the genes are actually part of the same pathway. In one embodiment in accordance with the present invention, the degree to which each gene making up a candidate pathway group belongs with other genes within the candidate pathway group is tested by fitting a multivariate statistical model to the candidate pathway group (FIG. 2; step 222). Multivariate statistical models have the capability of simultaneously considering multiple quantitative traits, modeling epistatic interactions between the genes and testing other interesting variations that determine whether genes in a candidate pathway group belong to the same or related biological pathway. Specific tests can be done to determine if the traits under consideration are actually controlled by the same QTL (pleiotropic effects) or if they are independent. Exemplary multivariate statistical models that can be used in accordance with the present invention are found in Section 5.6, infra.

The results of the multivariate analysis are used to "validate" the candidate pathway groups. These validated groups are then represented in a database and made available for the final stage of analysis, which involves reconstructing the pathway. At this stage the database comprises genes that are under some kind of common genetic control, interact to some degree at the expression level, and that have been shown to be strongly enough interacting at these different levels to perhaps belong to the same or related pathways. Thus, in some instances, the association of a gene with a trait exhibited by one or more organisms in a population of interest results in the placement of the gene in a pathway group that comprises genes that are part of the same or related pathway.

In some embodiments, an attempt to partially reconstruct the pathways within a given pathway group is made. For each candidate pathway group, the interactions between the representative gene analysis vectors and gene expression vectors can be examined. Furthermore, QTL and probe location information can be used to begin to piece together causal pathways. In addition, graphical models can be fit to the data using the interaction strengths, QTL overlap and physical location information accumulated from the previous steps to weight and direct the edges that link genes in a candidate pathway group. Application of such graphical models is used to determine which genes are more closely linked in a candidate pathway group and therefore suggests models for constraining the topology of the pathway. Thus, such models test whether it is more likely that the candidate pathway proceeds in a particular direction, given the evidence provided by the interactions, QTL overlaps, and physical QTL/probe location. The end result of this process, after starting with expression data, genotype data, and marker data, is a set of pathway groups consisting of genes that are supported as being part of the same or related pathway, and causal information that indicates the exact relationship of genes in the pathway (or of a partial set of genes in the pathway).

5.2. Sources of Marker Data

Several forms of genetic markers that are used to construct marker map 78 are known in the art. A common genetic marker is single nucleotide polymorphisms (SNPs). SNPs occur approximately once every 600 base pairs in the genome. See, for example, Kruglyak and Nickerson, 2001, Nature Genetics 27, 235. The present invention contemplates the use of genotypic databases such as SNP databases as a source of genetic markers. Alleles making up blocks of such SNPs in close physical proximity are often correlated, resulting in reduced genetic variability and defining a limited number of "SNP haplotypes" each of which reflects descent from a single ancient ancestral chromosome. See Fullerton et al., 2000, Am. J. Hum. Genet. 67, 881. Such haplotype structure is useful in selecting appropriate genetic variants for analysis. Patil et al. found that a very dense set of SNPs is required to capture all the common haplotype information. Once common haplotype information is available, it can be used to identify much smaller subsets of SNPs useful for comprehensive whole-genome studies. See Patil et al., 2001, Science 294, 1719–1723.

Other suitable sources of genetic markers include databases that have various types of gene expression data from platform types such as spotted microarray (microarray), high-density oligonucleotide array (HDA), hybridization filter (filter) and serial analysis of gene expression (SAGE) data. Another example of a genetic database that can be used is a DNA methylation database. For details on a representative DNA methylation database, see Grunau et al., in press, MethDB- a public database for DNA methylation data, *Nucleic Acids Research*; or the URL: http://genome.imb-jena.de/public.html.

In one embodiment of the present invention, a set of genetic markers is derived from any type of genetic database that tracks variations in the genome of an organism of interest. Information that is typically represented in such databases is a collection of loci within the genome of the organism of interest. For each locus, strains for which genetic variation information is available are represented. For each represented strain, variation information is provided. Variation information is any type of genetic variation information. Representative genetic variation information includes, but is not limited to, single nucleotide polymorphisms, restriction fragment length polymorphisms, microsatellite markers, restriction fragment length polymorphisms, and short tandem repeats. Therefore, suitable genotypic databases include, but are not limited to:

| Genetic variation type | Uniform resource location |
| --- | --- |
| SNP | http://bioinfo.pal.roche.com/usuka_bioinformatics/cgi-bin/msnp/msnp.pl |
| SNP | http://snp.cshl.org/ |
| SNP | http://www.ibc.wustl.edu/SNP/ |
| SNP | http://www-genome.wi.mit.edu/SNP/mouse/ |
| SNP | http://www.ncbi.nlm.nih.gov/SNP/ |
| Microsatellite markers | http://www.informatics.jax.org/searches/polymorphism_form.shtml |
| Restriction fragment length polymorphisms | http://www.informatics.jax.org/searches/polymorphism_form.shtml |
| Short tandem repeats | http://www.cidr.jhmi.edu/mouse/mmset.html |
| Sequence length polymorphisms | http://mcbio.med.buffalo.edu/mit.html |
| DNA methylation database | http ://genome.imb-jena.de/public.html |
| Short tandem-repeat polymorphisms | Broman et al., 1998, Comprehensive human genetic maps: Individual and sex-specific variation in recombination, American Journal of Human Genetics 63, 861–869 |
| Microsatellite markers | Kong et al., 2002, A high-resolution recombination map of the human genome, Nat Genet 31, 241–247 |

In addition, the genetic variations used by the methods of the present invention may involve differences in the expression levels of genes rather than actual identified variations in the composition of the genome of the organism of interest. Therefore, genotypic databases within the scope of the present invention include a wide array of expression profile databases such as the one found at the URL: http://www.ncbi.nlm.nih.gov/geo/.

Another form of genetic marker that may be used to construct marker map 78 is restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction endonuclease. Generally, the resulting fragments are separated according to size and hybridized with a probe; single copy probes are preferred. As a result, restriction fragments from homologous chromosomes are revealed. Differences in fragment size among alleles represent an RFLP (see, for example, Helentjaris et al., 1985, Plant Mol. Bio. 5:109–118, and U.S. Pat. No. 5,324,631). Another form of genetic marker that may be used to construct marker map 78 is random amplified polymorphic DNA (RAPD). The phrase "random amplified polymorphic DNA" or "RAPD" refers to the amplification product of the distance between DNA sequences homologous to a single oligonucleotide primer appearing on different sites on opposite strands of DNA. Mutations or rearrangements at or between binding sites will result in polymorphisms as detected by the presence or absence of amplification product (see, for example, Welsh and McClelland, 1990, Nucleic Acids Res. 18:7213–7218; Hu and Quiros, 1991, Plant Cell Rep. 10:505–511). Yet another form of genetic marker map that may be used to construct marker map 78 is amplified fragment length polymorphisms (AFLP). AFLP technology refers to a process that is designed to generate large numbers of randomly distributed molecular markers (see, for example, European Patent Application No. 0534858 A1). Still another form of genetic marker map that may be used to construct marker map 78 is "simple sequence repeats" or "SSRs". SSRs are di-, tri- or tetra-nucleotide tandem repeats within a genome. The repeat region may vary in length between genotypes while the DNA flanking the repeat is conserved such that the same primers will work in a plurality of genotypes. A polymorphism between two genotypes represents repeats of different lengths between the two flanking conserved DNA sequences (see, for example, Akagi et al., 1996, Theor. Appl. Genet. 93, 1071–1077; Bligh et al., 1995, Euphytica 86:83–85; Struss et al., 1998, Theor. Appl. Genet. 97, 308–315; Wu et al., 1993, Mol. Gen. Genet. 241, 225–235; and U.S. Pat. No. 5,075,217). SSR are also known as satellites or microsatellites.

As described above, many genetic markers suitable for use with the present invention are publicly available. Those skilled in the art can also readily prepare suitable markers. For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., 7–21.

5.3. Exemplary Normalization Routines

A number of different normalization protocols may be used by normalization module 72 to normalize gene expression data 44. Some such normalization protocols are described in this section. Typically, the normalization comprises normalizing the expression level measurement of each gene in a plurality of genes that is expressed by an organism in a population of interest. Many of the normalization protocols described in this section are used to normalize microarray data. It will be appreciated that there are many other suitable normalization protocols that may be used in accordance with the present invention. All such protocols are within the scope of the present invention. Many of the normalization protocols found in this section are found in publically available software, such as Microarray Explorer (Image Processing Section, Laboratory of Experimental and Computational Biology, National Cancer Institute, Frederick, Md. 21702, USA).

One normalization protocol is Z-score of intensity. In this protocol, raw expression intensities are normalized by the (mean intensity)/(standard deviation) of raw intensities for all spots in a sample. For microarray data, the Z-score of intensity method normalizes each hybridized sample by the mean and standard deviation of the raw intensities for all of the spots in that sample. The mean intensity $mnI_i$ and the standard deviation $sdI_i$ are computed for the raw intensity of control genes. It is useful for standardizing the mean (to 0.0) and the range of data between hybridized samples to about −3.0 to +3.0. When using the Z-score, the Z differences ($Z_{diff}$) are computed rather than ratios. The Z-score intensity (Z-score$_{ij}$) for intensity $I_{ij}$ for probe i (hybridization probe, protein, or other binding entity) and spot j is computed as:

$$Z\text{-score}_{ij} = (I_{ij} - mnI_i)/sdI_i,$$

and $$Zdiff_j(x,y) = Z\text{-score}_{xj} - Z\text{-score}_{yj}$$

where x represents the x channel and y represents the y channel.

Another normalization protocol is the median intensity normalization protocol in which the raw intensities for all spots in each sample are normalized by the median of the raw intensities. For microarray data, the median intensity normalization method normalizes each hybridized sample by the median of the raw intensities of control genes (median$I_i$) for all of the spots in that sample. Thus, upon normalization by the median intensity normalization method, the raw intensity $I_{ij}$ for probe i and spot j, has the value $Im_{ij}$ where, $$Im_{ij} = (I_{ij}/\text{median}I_i).$$

Another normalization protocol is the log median intensity protocol. In this protocol, raw expression intensities are normalized by the log of the median scaled raw intensities of representative spots for all spots in the sample. For microarray data, the log median intensity method normalizes each hybridized sample by the log of median scaled raw intensities of control genes (median$I_i$) for all of the spots in that sample. As used herein, control genes are a set of genes that have reproducible accurately measured expression values. The value 1.0 is added to the intensity value to avoid taking the log(0.0) when intensity has zero value. Upon normalization by the median intensity normalization method, the raw intensity $I_{ij}$ for probe i and spot j, has the value $Im_{ij}$ where, $$Im_{ij} = \log(1.0 + (I_{ij}/\text{median}I_i)).$$

Yet another normalization protocol is the Z-score standard deviation log of intensity protocol. In this protocol, raw expression intensities are normalized by the mean log intensity ($mnLI_i$) and standard deviation log intensity ($sdLI_i$). For microarray data, the mean log intensity and the standard deviation log intensity is computed for the log of raw intensity of control genes. Then, the Z-score intensity Z log $S_{ij}$ for probe i and spot j is:

$$Z \log S_{ij} = (\log(I_{ij}) - mnLI_i)/sdLI_i.$$

Still another normalization protocol is the Z-score mean absolute deviation of log intensity protocol. In this protocol, raw expression intensities are normalized by the Z-score of the log intensity using the equation (log(intensity)−mean logarithm)/standard deviation logarithm. For microarray data, the Z-score mean absolute deviation of log intensity protocol normalizes each bound sample by the mean and mean absolute deviation of the logs of the raw intensities for all of the spots in the sample. The mean log intensity $mnLI_i$ and the mean absolute deviation log intensity $madLI_i$ are computed for the log of raw intensity of control genes. Then, the Z-score intensity Z log $A_{ij}$ for probe i and spot j is:

$$Z \log A_{ij} = (\log(I_{ij}) - mnLI_i)/madLI_i.$$

Another normalization protocol is the user normalization gene set protocol. In this protocol, raw expression intensities are normalized by the sum of the genes in a user defined gene set in each sample. This method is useful if a subset of genes has been determined to have relatively constant expression across a set of samples. Yet another normalization protocol is the calibration DNA gene set protocol in which each sample is normalized by the sum of calibration DNA genes. As used herein, calibration DNA genes are genes that produce reproducible expression values that are accurately measured. Such genes tend to have the same expression values on each of several different microarrays. The algorithm is the same as user normalization gene set protocol described above, but the set is predefined as the genes flagged as calibration DNA.

Yet another normalization protocol is the ratio median intensity correction protocol. This protocol is useful in embodiments in which a two-color fluorescence labeling and detection scheme is used. (see Section 5.8.1.5.). In the case where the two fluors in a two-color fluorescence labeling and detection scheme are Cy3 and Cy5, measurements are normalized by multiplying the ratio (Cy3/Cy5) by medianCy5/medianCy3 intensities. If background correction is enabled, measurements are normalized by multiplying the ratio (Cy3/Cy5) by (medianCy5−medianBkgdCy5)/(medianCy3−medianBkgdCy3) where medianBkgd means median background levels.

In some embodiments, intensity background correction is used to normalize measurements. The background intensity data from a spot quantification programs may be used to correct spot intensity. Background may be specified as either a global value or on a per-spot basis. If the array images have low background, then intensity background correction may not be necessary.

5.4. Logarithmic of the Odds Scores

Denoting the joint probability of inheriting all genotypes P(g), and the joint probability of all observed data x (trait and marker species) conditional on genotypes P(x|g), the likelihood L for a set of data is $$L = \Sigma P(g)P(x|g)$$

where the summation is over all the possible joint genotypes g (trait and marker) for all pedigree members. What is unknown in this likelihood is the recombination fraction θ, on which P(g) depends.

The recombination fraction θ is the probability that two loci will recombine (segregate independently) during meioses. The recombination fraction θ is correlated with the distance between two loci. By definition, the genetic distance is defined to be infinity between the loci on different chromosomes (nonsyntenic loci), and for such unlinked loci, θ=0.5. For linked loci on the same chromosome (syntenic loci), θ<0.5, and the genetic distance is a monotonic function of θ. See, e.g., Ott, 1985, *Analysis of Human Genetic Linkage*, first edition, Baltimore, Md., John Hopkins University Press. The essence of linkage analysis described in Section 5.13, is to estimate the recombination fraction θ and to test whether θ=0.5. When the position of one locus in the genome is known, genetic linkage can be exploited to obtain an estimate of the chromosomal position of a second locus relative to the first locus. In linkage analysis described in Section 5.13, linkage analysis is used to map the unknown location of genes predisposing to various quantitative phenotypes relative to a large number of marker loci in a genetic map. In the ideal situation, where recombinant and nonrecombinant meioses can be counted unambiguously, θ is estimated by the frequency of recombinant meioses in a large sample of meioses. If two loci are linked, then the number of nonrecombinant meioses N is expected to be larger than the number of recombinant meioses R. The recombination fraction between the new locus and each marker can be estimated as:

$$\hat{\theta} = \frac{R}{N+R}$$

The likelihood of interest is:

$$L = \Sigma P(g|\theta) P(x|g)$$

and inferences are based about a test recombination fraction θ on the likelihood ratio Λ=L(θ)/L(½) or, equivalently, its logarithm.

Thus, in a typical clinical genetics study, the likelihood of the trait and a single marker is computed over one or more relevant pedigrees. This likelihood function L(θ) is a function of the recombination fraction θ between the trait (e.g., classical trait or quantitative trait) and the marker locus. The standardized log likelihood $Z(\theta) = \log_{10}[L(\theta)/L(½)]$ is referred to as a LOD score. Here, "LOD" is an abbreviation for "logarithm of the odds." A LOD score permits visualization of linkage evidence. As a rule of thumb, in human studies, geneticists provisionally accept linkage if $$Z(\hat{\theta}) \geq 3$$

at its maximum θ on the interval [0,½], where $\hat{\theta}$ represents the maximum θ on the interval. Further, linkage is provisionally rejected at a particular θ if $$Z(\theta) \leq -2.$$

Acceptance and rejection are treated asymmetrically because, with 22 pairs of human autosomes, it is unlikely that a random marker even falls on the same chromosome as a trait locus. See Lange, 1997, *Mathematical and Statistical Methods for Genetic Analysis*, Springer-Verlag, New York; Olson, 1999, Tutorial in Biostatistics: Genetic Mapping of Complex Traits, *Statistics in Medicine* 18, 2961–2981.

When the value of L is large, the null hypothesis of no linkage, L(½), to a marker locus of known location can be rejected, and the relative location of the locus corresponding to the quantitative trait can be estimated by $\hat{\theta}$. Therefore, LOD scores provide a method to calculate linkage distances as well as to estimate the probability that two genes (and/or QTLs) are linked.

In some embodiments of the LOD score method, a series of LOD scores are calculated from a number of proposed linkage distances. First, a linkage distance is estimated, and given that estimate, the probability of a given birth sequence is calculated. That value is then divided by the probability of a given birth sequence assuming that the genes (and/or QTLs) are unlinked (L(½)). The log of this value is calculated, and that value is the LOD score for this linkage distance estimate. The same process is repeated with another linkage distance estimate. A series of these LOD scores are obtained using different linkage distances, and the linkage distance giving the highest LOD score is considered the estimate of the linkage distance.

Those of skill in the art will appreciate that LOD score computation is species dependent. For example, methods for computing the LOD score in mouse different from that described in this section. However, methods for computing LOD scores are known in the art and the method described in this section is only by way of illustration and not by limitation.

5.5. Clustering Techniques

The subsections below describe exemplary methods for clustering gene analysis vectors in order to form QTL interaction maps. The same techniques can be applied to gene expression vectors in order to form gene expression cluster maps. In these techniques, gene analysis vectors 84 or gene expression vectors 304 are clustered based on the strength of interaction between the gene analysis 84 vectors or gene expression vectors 304. More information on clustering techniques can be found in Kaufman and Rousseeuw, 1990, *Finding Groups in Data: An Introduction to Cluster Analysis*, Wiley, New York, N.Y.; Everitt, 1993, *Cluster analysis* (3d ed.), Wiley, New York, N.Y.; Backer, 1995, *Computer-Assisted Reasoning in Cluster Analysis*, Prentice Hall, Upper Saddle River, N.J.; and Duda et al., 2001, *Pattern Classification*, John Wiley & Sons, New York, N.Y.

5.5.1. Hierarchical Clustering Techniques

Hierarchical cluster analysis is a statistical method for finding relatively homogenous clusters of elements based on measured characteristics. Consider a sequence of partitions of n samples into c clusters. The first of these is a partition into n clusters, each cluster containing exactly one sample. The next is a partition into n−1 clusters, the next is a partition into n−2, and so on until the $n^{th}$, in which all the samples form one cluster. Level k in the sequence of partitions occurs when c=n−k+1. Thus, level one corresponds to n clusters and level n corresponds to one cluster. Given any two samples x and x*, at some level they will be grouped together in the same cluster. If the sequence has the property that whenever two samples are in the same cluster at level k they remain together at all higher levels, then the sequence is said to be a hierarchical clustering. Duda et al., 2001, *Pattern Classification*, John Wiley & Sons, New York, 2001, p. 551.

5.5.1.1. Agglomerative Clustering

In some embodiments, the hierarchical clustering technique used to cluster gene analysis vectors 84 or gene expression vectors 304 is an agglomerative clustering procedure. Agglomerative (bottom-up clustering) procedures start with n singleton clusters and form a sequence of partitions by successively merging clusters. The major steps in agglomerative clustering are contained in the following procedure, where c is the desired number of final clusters, $D_i$ and $D_j$ are clusters, $x_i$ is a gene analysis vector 84 or gene expression vector 304, and there are n such vectors:

```
1    begin initialize c, ĉ ← n, D_i ← {x_i}, i = 1, . . . , n
2         do ĉ ← ĉ−1
3              find nearest clusters, say, D_i and D_j
4              merge D_i and D_j
5         until c = ĉ
6         return c clusters
7    end
```

In this algorithm, the terminology a←b assigns to variable a the new value b. As described, the procedure terminates when the specified number of clusters has been obtained and returns the clusters as a set of points. A key point in this algorithm is how to measure the distance between two clusters $D_i$ and $D_j$. The method used to define the distance between clusters $D_i$ and $D_j$ defines the type of agglomerative clustering technique used. Representative techniques include the nearest-neighbor algorithm, farthest-neighbor algorithm, the average linkage algorithm, the centroid algorithm, and the sum-of-squares algorithm.

Nearest-neighbor algorithm. The nearest-neighbor algorithm uses the following equation to measure the distances between clusters:

$$d_{min}(D_i, D_j) = \min_{\substack{x \in D_i \\ x' \in D_j}} \|x - x'\|.$$

This algorithm is also known as the minimum algorithm. Furthermore, if the algorithm is terminated when the distance between nearest clusters exceeds an arbitrary threshold, it is called the single-linkage algorithm. Consider the case in which the data points are nodes of a graph, with edges forming a path between the nodes in the same subset $D_i$. When dmin( ) is used to measure the distance between subsets, the nearest neighbor nodes determine the nearest subsets. The merging of $D_i$ and $D_j$ corresponds to adding an edge between the nearest pari of nodes in $D_i$ and $D_j$. Because edges linking clusters always go between distinct clusters, the resulting graph never has any closed loops or circuits; in the terminology of graph theory, this procedure generates a tree. If it is allowed to continue until all of the subsets are linked, the result is a spanning tree. A spanning tree is a tree with a path from any node to any other node. Moreover, it can be shown that the sum of the edge lengths of the resulting tree will not exceed the sum of the edge lengths for any other spanning tree for that set of samples. Thus, with the use of dmin( ) as the distance measure, the agglomerative clustering procedure becomes an algorithm for generating a minimal spanning tree. See Duda et al., id, pp. 553–554.

Farthest-neighbor algorithm. The farthest-neighbor algorithm uses the following equation to measure the distances between clusters:

$$d_{min}(D_i, D_j) = \max_{\substack{x \in D_i \\ x' \in D_j}} \|x - x'\|.$$

This algorithm is also known as the maximum algorithm. If the clustering is terminated when the distance between the nearest clusters exceeds an arbitrary threshold, it is called the complete-linkage algorithm. The farthest-neighbor algorithm discourages the growth of elongated clusters. Application of this procedure can be thought of as producing a graph in which the edges connect all of the nodes in a cluster. In the terminology of graph theory, every cluster contains a complete subgraph. The distance between two clusters is terminated by the most distant nodes in the two clusters. When the nearest clusters are merged, the graph is changed by adding edges between every pair of nodes in the two clusters.

Average linkage algorithm. Another agglomerative clustering technique is the average linkage algorithm. The average linkage algorithm uses the following equation to measure the distances between clusters:

$$d_{avg}(D_i, D_j) = \frac{1}{n_i n_j} \sum_{x \in D_i} \sum_{x' \in D_j} \|x - x'\|.$$

Hierarchical cluster analysis begins by making a pair-wise comparison of all gene analysis vectors 84 or gene expression vectors 304 in a set of quantitative trait locus vectors or gene expression vectors. After evaluating similarities from all pairs of elements in the set, a distance matrix is constructed. In the distance matrix, a pair of vectors with the shortest distance (i.e. most similar values) is selected. Then, when the average linkage algorithm is used, a "node" ("cluster") is constructed by averaging the two vectors. The similarity matrix is updated with the new "node" ("cluster") replacing the two joined elements, and the process is repeated n−1 times until only a single element remains. Consider six elements, A–F having the values:

A{4.9}, B{8.2}, C{3.0}, D{5.2}, E{8.3}, F{2.3}.

In the first partition, using the average linkage algorithm, one matrix (sol. 1) that could be computed is:

(sol. 1) A{4.9}, B–E{8.25}, C{3.0}, D{5.2}, F{2.3}.

Alternatively, the first partition using the average linkage algorithm could yield the matrix:

(sol. 2) A{4.9}, C{3.0}, D{5.2}, E–B{8.25}, F{2.3}.

Assuming that solution 1 was identified in the first partition, the second partition using the average linkage algorithm will yield:

(sol. 1-1) A–D{5.05}, B–E{8.25}, C{3.0}, F{2.3} or (sol. 1-2) B–E{8.25}, C{3.0}, D–A{5.05}, F{2.3}.

Assuming that solution 2 was identified in the first partition, the second partition of the average linkage algorithm will yield:

(sol. 2-1) A–D{5.05}, C{3.0}, E–B{8.25}, F{2.3} or (sol. 2-2) C{3.0}, D–A{5.05}, E–B{8.25}, F{2.3}.

Thus, after just two partitions in the average linkage algorithm, there are already four matrices. See Duda et al., Pattern Classification, John Wiley & Sons, New York, 2001, p. 551.

Centroid algorithm. In the centroid method, the distances or similarities are calculated between the centroids of the clusters D.

Sum-of-squares algorithm. The sum of squares method is also known as the "Wards' method." In the Wards' method, cluster membership is assessed by calculating the total sum of squared deviations from the mean of a cluster. See Lance and Williams, 1967, A general theory of classificatory sorting strategies, *Computer Journal* 9: 373–380.

5.5.1.2. Clustering with Pearson Correlation Coefficients

In one embodiment of the present invention, gene analysis vectors 84 or gene expression vectors 304 are clustered using agglomerative hierarchical clustering with Pearson correlation coefficients. In this form of clustering, similarity is determined using Pearson correlation coefficients between the gene analysis vector pairs or gene expression vector pairs. Other metrics that can be used, in addition to the Pearson correlation coefficient, include but are not limited to, a Euclidean distance, a squared Euclidean distance, a Euclidean sum of squares, a Manhattan metric, and a squared Pearson correlation coefficient. Such metrics may be computed using SAS (Statistics Analysis Systems Institute, Cary, N.C.) or S-Plus (Statistical Sciences, Inc., Seattle, Wash.).

5.5.1.3. Divisive Clustering

In some embodiments, the hierarchical clustering technique used to cluster gene analysis vectors 84 or gene expression vectors 304 is a divisive clustering procedure. Divisive (top-down clustering) procedures start with all of the samples in one cluster and form the sequence by successfully splitting clusters. Divisive clustering techniques are classified as either a polythetic or a monthetic method. A polythetic approach divides clusters into arbitrary subsets.

5.5.2. K-Means Clustering

In k-means clustering, sets of gene analysis vectors 84 or gene expression vectors 304 are randomly assigned to K user specified clusters. The centroid of each cluster is computed by averaging the value of the vectors in each cluster. Then, for each i=1, . . . , N, the distance between vector $x_i$ and each of the cluster centroids is computed. Each vector $x_i$ is then reassigned to the cluster with the closest centroid. Next, the centroid of each affected cluster is recalculated. The process iterates until no more reassignments are made. See Duda et al., id., pp. 526–528. A related approach is the fuzzy k-means clustering algorithm, which is also known as the fuzzy c-means algorithm. In the fuzzy k-means clustering algorithm, the assumption that every gene analysis vector 84 or gene expression vector 304 is in exactly one cluster at any given time is relaxed so that every vector has some graded or "fuzzy" membership in a cluster. See Duda et al., id., pp. 528–530.

5.5.3. Jarvis-Patrick Clustering

Jarvis-Patrick clustering is a nearest-neighbor non-hierarchical clustering method in which a set of objects is partitioned into clusters on the basis of the number of shared nearest-neighbors. In the standard implementation advocated by Jarvis and Patrick, 1973, *IEEE Trans. Comput.*, C-22:1025–1034, a preprocessing stage identifies the K nearest-neighbors of each object in the dataset. In the subsequent clustering stage, two objects i and j join the same cluster if (i) i is one of the K nearest-neighbors of j, (ii) j is one of the K nearest-neighbors of i, and (iii) i and j have at least $k_{min}$ of their K nearest-neighbors in common, where K and $k_{min}$ are user-defined parameters. The method has been widely applied to clustering chemical structures on the basis of fragment descriptors and has the advantage of being much less computationally demanding than hierarchical methods, and thus more suitable for large databases. Jarvis-Patrick clustering may be performed using the Jarvis-Patrick Clustering Package 3.0 (Barnard Chemical Information, Ltd., Sheffield, United Kingdom).

5.5.4. Neural Networks

A neural network has a layered structure that includes a layer of input units (and the bias) connected by a layer of weights to a layer of output units. In multilayer neural networks, there are input units, hidden units, and output units. In fact, any function from input to output can be implemented as a three-layer network. In such networks, the weights are set based on training patterns and the desired output. One method for supervised training of multilayer neural networks is back-propagation. Back-propagation allows for the calculation of an effective error for each hidden unit, and thus derivation of a learning rule for the input-to-hidden weights of the neural network.

The basic approach to the use of neural networks is to start with an untrained network, present a training pattern to the input layer, and pass signals through the net and determine the output at the output layer. These outputs are then compared to the target values; any difference corresponds to an error. This error or criterion function is some scalar function of the weights and is minimized when the network outputs match the desired outputs. Thus, the weights are adjusted to reduce this measure of error. Three commonly used training protocols are stochastic, batch, and on-line. In stochastic training, patterns are chosen randomly from the training set and the network weights are updated for each pattern presentation. Multilayer nonlinear networks trained by gradient descent methods such as stochastic back-propagation perform a maximum-likelihood estimation of the weight values in the model defined by the network topology. In batch training, all patterns are presented to the network before learning takes place. Typically, in batch training, several passes are made through the training data. In online training, each pattern is presented once and only once to the net.

5.5.5. Self-Organizing Maps

A self-organizing map is a neural-network that is based on a divisive clustering approach. The aim is to assign genes to a series of partitions on the basis of the similarity of their expression vectors to reference vectors that are defined for each partition. Consider the case in which there are two microarrays from two different experiments. It is possible to build up a two-dimensional construct where every spot corresponds to the expression levels of any given gene in the two experiments. A two-dimensional grid is built, resulting in several partitions of the two-dimensional construct. Next, a gene is randomly picked and the identify of the reference vector (node) closest to the gene picked is determined based on a distance matrix. The reference vector is then adjusted so that it is more similar to the vector of the assigned gene. That means the reference vector is moved one distance unit on the x axis and y-axis and becomes closer to the assigned gene. The other nodes are all adjusted to the assigned gene, but only are moved one half or one-fourth distance unit. This cycle is repeated hundreds of thousands times to converge the reference vector to fixed value and where the grid is stable. At that time, every reference vector is the center of a group of genes. Finally, the genes are mapped to the relevant partitions depending on the reference vector to which they are most similar.

5.6. Multivariate Statistical Models

Using the methods of the present invention, candidate pathway groups are identified from the analysis of QTL interaction map data and gene expression cluster maps. Each candidate pathway group includes a number of genes. The methods of the present invention are advantageous because they filter the potentially thousands of genes in the genome of the population of interest into a few candidate pathway groups using clustering techniques. In a typical case, a candidate pathway group represents a group of genes that tightly cluster in a gene expression cluster map. In some embodiments, the genes in a candidate pathway group also cluster tightly in a QTL interaction map. The QTL interaction map serves as a complementary approach to defining the genes in a candidate pathway group. For example, consider the case in which genes A, B, and C cluster tightly in a gene expression cluster map. Furthermore, genes A, B, C and D cluster tightly in the corresponding QTL interaction map. In this example, analysis of the gene expression cluster map alone suggest that genes A, B, C form a candidate pathway group. However, analysis of both the QTL interaction map and the gene expression cluster map suggest that the candidate pathway group actually comprises genes A, B, C, and D.

Once candidate pathway groups have been identified, multivariate statistical models can be applied to determine whether each of the genes in the candidate pathway group affect a particular trait, such as a complex disease trait. The form of multivariate statistical analysis used in some embodiments of the present invention is dependent upon on the type of genotype and/or pedigree data 68 (FIG. 1) that is available. Typically, more pedigree data is available in cases where the population to be studied is plants or animals. In such instances, the multivariate statistical models used are in accordance with those of Jiang and Zeng, 1995, Multiple trait analysis of genetic mapping for quantitative trait loci, *Nature Genetics* 140:1111–1127 as well as the techniques implemented in QTL Cartographer (Basten and Zeng, 1994, Zmap-a QTL cartographer, *Proceedings of the 5th World Congress on Genetics Applied to Livestock Production: Computing Strategies and Software*, Smith et al. eds., 22:65–66, The Organizing Committee, 5th World Congress on Genetics Applied to Livestock Production, Guelph, Ontario, Canada; Basten et al., 2001, *QTL Cartographer, Version 1.15*, Department of Statistics, North Carolina State University, Raleigh, N.C. For human genotype and pedigree data 68 (FIG. 1), methods described in Allison, 1998, Multiple Phenotype Modeling in Gene-Mapping Studies of Quantitative Traits: Power Advantages, *Am J. Hum. Genetics* 63:1190–1201 are used, including, but not limited to, those of Amos et al., 1990, A Multivariate Method for Detecting Genetic Linkage, with Application to a Pedigree with an Adverse Lipoprotein Protein, *Am J. Hum. Genetics* 47:247–254.

In some embodiments, gene expression data 44 is collected for multiple tissue types. In such instances, multivariate analysis can be used to determine the true nature of a complex disease. Multivariate techniques used in this embodiment of the invention are described, in part, in Williams et al., 1999, *Am J Hum Genet* 65(4): 1134–47; Amos et al., 1990, *Am J Hum Genet* 47(2): 247–54, and Jiang and Zeng, 1995, *Nature Genetics* 140:1111–1127.

Asthma provides one example of a complex disease that can be studied using expression data from multiple tissue types. Asthma is expected to, in part, be influenced by immune system response not only in lungs but also in blood. By measuring expression of genes in the lung and in blood, the following model could be used to dissect the shared genetic effect in a model system, e.g. an F2 mouse cross:

$$y_{j1} = \alpha_1 + b_1 x_j + d_1 z_j + e_{j1}$$

-continued
$$y_{j2} = \alpha_2 + b_2 x_j + d_2 z_j + e_{j2}$$
$$\vdots$$
$$y_{jm} = \alpha_m + b_m x_j + d_m z_j + e_{jm}$$

where, for individual j and a putative QTL:

$y_{i1}, \ldots, j_{jm}$ consists of asthma relevant phenotypes, expression data for gene expression in the lung and expression data for gene expression in blood;

$x_j$ is the number of QTL alleles from a specific parental line;

$z_j$ is 1 if the individual is heterozygous for the QTL and 0 otherwise;

$\alpha_i$ represents the mean for phenotype i;

$b_i$ and $d_i$ represent the additive and dominance effects of the QTL on phenotype i;

and $e_{ji}$ is the residual error for individual j and phenotype i.

It is typically assumed that the residuals are uncorrelated between individuals, and the correlation between residuals within an individual are modeled as $Cov(e_{jk}, e_{j1}) = \rho_{k1} \sigma_k \sigma_1$. Assuming a multivariate normal distribution for the residuals, likelihood analysis can be used to test for joint linkage of a QTL to the trait vector and to test for pleiotropic effects versus close linkage. With such information, it would be possible to detect a QTL that influences susceptibility to asthma through causing changes in gene expression for a set of genes expressed in blood and for a set of, potentially overlapping, genes expressed in lung. Such multivariate analyses in accordance with the present invention, combined with high quality phenotypic data that includes expression data across multiple tissues, allows for improved detection of those genes truly influencing susceptibility to complex diseases.

5.7. Analytic Kit Implementation

In a preferred embodiment, the methods of this invention can be implemented by use of kits for determining the responses or state of a biological sample. Such kits contain microarrays, such as those described in Subsections below. The microarrays contained in such kits comprise a solid phase, e.g., a surface, to which probes are hybridized or bound at a known location of the solid phase. Preferably, these probes consist of nucleic acids of known, different sequence, with each nucleic acid being capable of hybridizing to an RNA species or to a cDNA species derived therefrom. In a particular embodiment, the probes contained in the kits of this invention are nucleic acids capable of hybridizing specifically to nucleic acid sequences derived from RNA species in cells collected from an organism of interest.

In one embodiment, a kit of the invention also contains one or more databases described above and in FIG. 1, encoded on computer readable medium, and/or an access authorization to use the databases described above from a remote networked computer.

In another embodiment, a kit of the invention further contains software capable of being loaded into the memory of a computer system such as the one described supra, and illustrated in FIG. 1. The software contained in the kit of this invention, is essentially identical to the software described above in conjunction with FIG. 1. Alternative kits for implementing the analytic methods of this invention will be apparent to one of skill in the art and are intended to be comprehended within the accompanying claims.

5.8. Transcriptional State Measurements

The section provides some exemplary methods for measuring the expression level of genes, which are one type of cellular constituent. One of skill in the art will appreciate that this invention is not limited to the following specific methods for measuring the expression level of genes in each organism in a plurality of organisms.

5.8.1. Transcript Assay Using Microarrays

The techniques described in this section are particularly useful for the determination of the expression state or the transcriptional state of a cell or cell type or any other cell sample by monitoring expression profiles. These techniques include the provision of polynucleotide probe arrays for simultaneous determination of the expression levels of a plurality of genes. These techniques further provide methods for designing and making such polynucleotide probe arrays.

The expression level of a nucleotide sequence in a gene can be measured by any high throughput techniques. However measured, the result is either the absolute or relative amounts of transcripts or response data, including but not limited to values representing abundances or abundance rations. Preferably, measurement of the expression profile is made by hybridization to transcript arrays, which are described in this subsection. In one embodiment, the present invention makes use of "transcript arrays" or "profiling arrays". Transcript arrays can be employed for analyzing the expression profile in a cell sample and especially for measuring the expression profile of a cell sample of a particular tissue type or developmental state or exposed to a drug of interest or to perturbations to a biological pathway of interest.

In one embodiment, an expression profile is obtained by hybridizing detectably labeled polynucleotides representing the nucleotide sequences in mRNA transcripts present in a cell (e.g., fluorescently labeled cDNA synthesized from total cell mRNA) to a microarray. A microarray is an array of positionally-addressable binding (e.g., hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways, of which several are described herein below. However produced, microarrays share certain characteristics. The arrays are reproducible, allowing multiple copies of a given array to be produced and easily compared with each other. Preferably, the microarrays are made from materials that are stable under binding (e.g., nucleic acid hybridization) conditions. The microarrays are preferably small, e.g., between about 1 $cm^2$ and 25 $cm^2$, preferably about 1 to 3 $cm^2$. However, both larger and smaller arrays are also contemplated and may be preferable, e.g., for simultaneously evaluating a very large number of different probes.

Preferably, a given binding site or unique set of binding sites in the microarray will specifically bind (e.g., hybridize) to a nucleotide sequence in a single gene from a cell or organism (e.g., to exon of a specific mRNA or a specific cDNA derived therefrom).

The microarrays used in the methods and compositions of the present invention include one or more test probes, each of which has a polynucleotide sequence that is complementary to a subsequence of RNA or DNA to be detected. Each probe preferably has a different nucleic acid sequence, and the position of each probe on the solid surface of the array is preferably known. Indeed, the microarrays are preferably addressable arrays, more preferably positionally addressable arrays. More specifically, each probe of the array is preferably located at a known, predetermined position on the solid support such that the identity (i.e., the sequence) of each probe can be determined from its position on the array (i.e., on the support or surface). In some embodiments of the invention, the arrays are ordered arrays.

Preferably, the density of probes on a microarray or a set of microarrays is about 100 different (i.e., non-identical) probes per 1 $cm^2$ or higher. More preferably, a microarray used in the methods of the invention will have at least 550 probes per 1 $cm^2$, at least 1,000 probes per 1 $cm^2$, at least 1,500 probes per 1 $cm^2$ or at least 2,000 probes per 1 $cm^2$. In a particularly preferred embodiment, the microarray is a high density array, preferably having a density of at least about 2,500 different probes per 1 $cm^2$. The microarrays used in the invention therefore preferably contain at least 2,500, at least 5,000, at least 10,000, at least 15,000, at least 20,000, at least 25,000, at least 50,000 or at least 55,000 different (i.e., non-identical) probes.

In one embodiment, the microarray is an array (i.e., a matrix) in which each position represents a discrete binding site for a nucleotide sequence of a transcript encoded by a gene (e.g., for an exon of an mRNA or a cDNA derived therefrom). The collection of binding sites on a microarray contains sets of binding sites for a plurality of genes. For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments of the present invention, a gene or an exon in a gene is represented in the profiling arrays by a set of binding sites comprising probes with different polynucleotides that are complementary to different sequence segments of the gene or the exon. In some embodiments, such polynucleotides are of the length of 15 to 200 bases. In other embodiments, such polynucleotides are of length 20 to 100 bases. In still other embodiments, such polynucleotides are of length 40 to 60 bases. However, the size of such polynucleotides is highly application dependent. Accordingly, other sizes are possible. It will be understood that each probe sequence may also comprise linker sequences in addition to the sequence that is complementary to its target sequence. As used herein, a linker sequence refers to a sequence between the sequence that is complementary to its target sequence and the surface of support. For example, in preferred embodiments the profiling arrays of the invention comprise one probe specific to each target gene or exon.

However, if desired, the profiling arrays may contain at least 2, 5, 10, 100, 1000, or more probes specific to some target genes or exons. For example, the array may contain probes tiled across the sequence of the longest mRNA isoform of a gene at single base steps.

In specific embodiments of the invention, when an exon has alternative spliced variants, a set of polynucleotide probes of successive overlapping sequences, i.e., tiled sequences, across the genomic region containing the longest variant of an exon can be included in the exon profiling arrays. The set of polynucleotide probes can comprise successive overlapping sequences at steps of a predetermined base intervals, e.g. at steps of 1, 5, or 10 base intervals, span, or are tiled across, the mRNA containing the longest variant. Such set of probes therefore can be used to scan the genomic region containing all variants of an exon to determine the expressed variant or variants of the exon to determine the expressed variant or variants of the exon. Alternatively or additionally, a set of polynucleotide probes comprising exon specific probes and/or variant junction probes can be included in the exon profiling array. As used herein, a variant junction probe refers to a probe specific to the junction region of the particular exon variant and the neighboring exon. In a preferred embodiment, the probe set contains variant junction probes specifically hybridizable to each of all different splice junction sequences of the exon. In another preferred embodiment, the probe set contains exon specific probes specifically hybridizable to the common sequences in all different variants of the exon, and/or variant junction probes specifically hybridizable to the different splice junction sequences of the exon.

In some cases, an exon is represented in the exon profiling arrays by a probe comprising a polynucleotide that is complementary to the full length exon. In such embodiments, an exon is represented by a single binding site on the profiling arrays. In some preferred embodiments of the invention, an exon is represented by one or more binding sites on the profiling arrays, each of the binding sites comprising a probe with a polynucleotide sequence that is complementary to an RNA fragment that is a substantial portion of the target exon. The lengths of such probes are normally between about 15–600 bases, preferably between about 20–200 bases, more preferably between about 30–100 bases, and most preferably between about 40–80 bases. The average length of an exon is about 50 bases (See The Genome Sequencing Consortium, 2001, Initial sequencing and analysis of the human genome, Nature 409, 860–921). A probe of length of about 40–80 allows more specific binding of the exon than a probe of shorter length, thereby increasing the specificity of the probe to the target exon. For certain genes, one or more targeted exons may have sequence lengths less than about 40–80 bases. In such cases, if probes with sequences longer than the target exons are to be used, it may be desirable to design probes comprising sequences that include the entire target exon flanked by sequences from the adjacent constitutively splice exon or exons such that the probe sequences are complementary to the corresponding sequence segments in the mRNAs. Using flanking sequence from adjacent constitutively spliced exon or exons rather than the genomic flanking sequences, i.e., intron sequences, permits comparable hybridization stringency with other probes of the same length. Preferably the flanking sequence used are from the adjacent constitutively spliced exon or exons that are not involved in any alternative pathways. More preferably the flanking sequences used do not comprise a significant portion of the sequence of the adjacent exon or exons so that cross-hybridization can be minimized. In some embodiments, when a target exon that is shorter than the desired probe length is involved in alternative splicing, probes comprising flanking sequences in different alternatively spliced mRNAs are designed so that expression level of the exon expressed in different alternatively spliced mRNAs can be measured.

In some instances, when alternative splicing pathways and/or exon duplication in separate genes are to be distinguished, the DNA array or set of arrays can also comprise probes that are complementary to sequences spanning the junction regions of two adjacent exons. Preferably, such probes comprise sequences from the two exons which are not substantially overlapped with probes for each individual exons so that cross hybridization can be minimized. Probes that comprise sequences from more than one exons are useful in distinguishing alternative splicing pathways and/or expression of duplicated exons in separate genes if the exons occur in one or more alternative spliced mRNAs and/or one or more separated genes that contain the duplicated exons but not in other alternatively spliced mRNAs and/or other genes that contain the duplicated exons. Alternatively, for duplicate exons in separate genes, if the exons from different genes show substantial difference in sequence homology, it is preferable to include probes that are different so that the exons from different genes can be distinguished.

It will be apparent to one skilled in the art that any of the probe schemes, supra, can be combined on the same profiling array and/or on different arrays within the same set of profiling arrays so that a more accurate determination of the expression profile for a plurality of genes can be accomplished. It will also be apparent to one skilled in the art that the different probe schemes can also be used for different levels of accuracies in profiling. For example, a profiling array or array set comprising a small set of probes for each exon may be used to determine the relevant genes and/or RNA splicing pathways under certain specific conditions. An array or array set comprising larger sets of probes for the exons that are of interest is then used to more accurately determine the exon expression profile under such specific conditions. Other DNA array strategies that allow more advantageous use of different probe schemes are also encompassed.

Preferably, the microarrays used in the invention have binding sites (i.e., probes) for sets of exons for one or more genes relevant to the action of a drug of interest or in a biological pathway of interest. As discussed above, a "gene" is identified as a portion of DNA that is transcribed by RNA polymerase, which may include a 5' untranslated region ("UTR"), introns, exons and a 3' UTR. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the genome of *Saccharomyces cerevisiae* has been completely sequenced and is reported to have approximately 6275 ORFs encoding sequences longer the 99 amino acid residues in length. Analysis of these ORFs indicates that there are 5,885 ORFs that are likely to encode protein products (Goffeau et al., 1996, *Science* 274:546–567). In contrast, the human genome is estimated to contain approximately 30,000 to 40,000 genes (see Venter et al., 2001, The Sequence of the Human Genome, *Science* 291:1304–1351). In some embodiments of the invention, an array set comprising in total probes for all known or predicted exons in the genome of an organism is provided. As a non-limiting example, the present invention provides an array set comprising one or two probes for each known or predicted exon in the human genome.

It will be appreciated that when cDNA complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In one embodiment, cDNAs from cell samples from two different conditions are hybridized to the binding sites of the microarray using a two-color protocol. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA derived from each of the two cell types are differently labeled (e.g., with Cy3 and Cy5) so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, change the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exon expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467–470, which is incorporated by reference in its entirety for all purposes. The scheme is equally applicable to labeling and detection of exons. An advantage of using cDNA labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell. Furthermore, labeling with more than two colors is also contemplated in the present invention. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

In some embodiments of the invention, hybridization data are measured at a plurality of different hybridization times so that the evolution of hybridization levels to equilibrium can be determined. In such embodiments, hybridization levels are most preferably measured at hybridization times spanning the range from 0 to in excess of what is required for sampling of the bound polynucleotides (i.e., the probe or probes) by the labeled polynucleotides so that the mixture is close to or substantially reached equilibrium, and duplexes are at concentrations dependent on affinity and abundance rather than diffusion. However, the hybridization times are preferably short enough that irreversible binding interactions between the labeled polynucleotide and the probes and/or the surface do not occur, or are at least limited. For example, in embodiments wherein polynucleotide arrays are used to probe a complex mixture of fragmented polynucleotides, typical hybridization times may be approximately 0–72 hours. Appropriate hybridization times for other embodiments will depend on the particular polynucleotide sequences and probes used, and may be determined by those skilled in the art (see, e.g., Sambrook et al., Eds., 1989, *Molecular Cloning: A Laboratory Manual*, 2nd ed., Vol. 1–3, Cold Spring Harbor Laboratory, Cold Spring Harbor, N.Y.).

In one embodiment, hybridization levels at different hybridization times are measured separately on different, identical microarrays. For each such measurement, at hybridization time when hybridization level is measured, the microarray is washed briefly, preferably in room temperature in an aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used. The resulted hybridization levels are then combined to form a hybridization curve. In another embodiment, hybridization levels are measured in real time using a single microarray. In this embodiment, the microarray is allowed to hybridize to the sample without interruption and the microarray is interrogated at each hybridization time in a non-invasive manner. In still another embodiment, one can use one array, hybridize for a short time, wash and measure the hybridization level, put back to the same sample, hybridize for another period of time, wash and measure again to get the hybridization time curve.

Preferably, at least two hybridization levels at two different hybridization times are measured, a first one at a hybridization time that is close to the time scale of cross-hybridization equilibrium and a second one measured at a hybridization time that is longer than the first one. The time scale of cross-hybridization equilibrium depends, inter alia, on sample composition and probe sequence and may be determined by one skilled in the art. In preferred embodiments, the first hybridization level is measured at between 1 to 10 hours, whereas the second hybridization time is measured at about 2, 4, 6, 10, 12, 16, 18, 48 or 72 times as long as the first hybridization time.

5.8.1.1. Preparing Probes for Microarrays

As noted above, the "probe" to which a particular polynucleotide molecule, such as an exon, specifically hybridizes according to the invention is a complementary polynucleotide sequence. Preferably one or more probes are selected for each target exon. For example, when a minimum number of probes are to be used for the detection of an exon, the probes normally comprise nucleotide sequences greater than about 40 bases in length. Alternatively, when a large set of redundant probes is to be used for an exon, the probes normally comprise nucleotide sequences of about 40–60 bases. The probes can also comprise sequences complementary to full length exons. The lengths of exons can range from less than 50 bases to more than 200 bases. Therefore, when a probe length longer than exon is to be used, it is preferable to augment the exon sequence with adjacent constitutively spliced exon sequences such that the probe sequence is complementary to the continuous mRNA fragment that contains the target exon. This will allow comparable hybridization stringency among the probes of an exon profiling array. It will be understood that each probe sequence may also comprise linker sequences in addition to the sequence that is complementary to its target sequence.

The probes may comprise DNA or DNA "mimics" (e.g., derivatives and analogues) corresponding to a portion of each exon of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of exon segments from genomic DNA, cDNA (e.g., by RT-PCR), or cloned sequences. PCR primers are preferably chosen based on known sequence of the exons or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g. using N-phosphonate or phosphoramidite chemistries (Froehler et al., 1986, *Nucleic Acid Res.* 14:5399–5407; McBride et al., 1983, *Tetrahedron Lett.* 24:246–248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566–568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207–209).

5.8.1.2. Attaching Nucleic Acids to the Solid Surface

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

A preferred method for attaching the nucleic acids to a surface is by printing on glass plates, as is described generally by Schena et al, 1995, *Science* 270:467–470. This method is especially useful for preparing microarrays of cDNA (See also, DeRisi et al, 1996, *Nature Genetics* 14:457–460; Shalon et al., 1996, *Genome Res.* 6:639–645; and Schena et al., 1995, *Proc. Natl. Acad. Sci. U.S.A.* 93:10539–11286).

A second preferred method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251: 767–773; Pease et al., 1994, *Proc. Natl. Acad. Sci. U.S.A.* 91:5022–5026; Lockhart et al., 1996, *Nature Biotechnology* 14:1675; U.S. Pat. Nos. 5,578,832; 5,556,752; and 5,510, 270) or other methods for rapid synthesis and deposition of defined oligonucleotides (Blanchard et al., *Biosensors & Bioelectronics* 11:687–690). When these methods are used, oligonucleotides (e.g., 60-mers) of known sequence are synthesized directly on a surface such as a derivatized glass slide. The array produced can be redundant, with several polynucleotide molecules per exon.

Other methods for making microarrays, e.g., by masking (Maskos and Southern, 1992, *Nucl. Acids. Res.* 20:1679–1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687–690; Blanchard, 1998, in *Synthetic DNA Arrays in Genetic Engineering*, Vol. 20, J. K. Setlow, Ed., Plenum Press, New York at pages 111–123; and U.S. Pat. No. 6,028,189 to Blanchard. Specifically, the polynucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Polynucleotide probes are normally attached to the surface covalently at the 3' end of the polynucleotide. Alternatively, polynucleotide probes can be attached to the surface covalently at the 5' end of the polynucleotide (see for example, Blanchard, 1998, in *Synthetic DNA Arrays in Genetic Engineering*, Vol. 20, J. K. Setlow, Ed., Plenum Press, New York at pages 111–123).

5.8.1.3. Target Polynucleotide Molecules

Target polynucleotides which may be analyzed by the methods and compositions of the invention include RNA molecules such as, but by no means limited to messenger RNA (mRNA) molecules, ribosomal RNA (rRNA) molecules, cRNA molecules (i.e., RNA molecules prepared from cDNA molecules that are transcribed in vivo) and fragments thereof. Target polynucleotides which may also be analyzed by the methods and compositions of the present invention include, but are not limited to DNA molecules such as genomic DNA molecules, cDNA molecules, and fragments thereof including oligonucleotides, ESTs, STSs, etc.

The target polynucleotides may be from any source. For example, the target polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian cells, the target polynucleotides may correspond to particular fragments of a gene transcript. For example, the target polynucleotides may correspond to different exons of the same gene, e.g., so that different splice variants of that gene may be detected and/or analyzed.

In preferred embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation and an oligo dT purification (Chirgwin et al., 1979, *Biochemistry* 18:5294–5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In preferred embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891,636, 5,716, 785; 5,545,522 and 6,132,997; see also, U.S. Pat. No. 6,271,002, and PCT Publication No. WO 02/44399 dated Jun. 6, 2002). Both oligo-dT primers (U.S. Pat. Nos. 5,545, 522 and 6,132,997) or random primers (PCT WO 02/44399 dated Jun. 6, 2002) that contain an RNA polymerase promoter or complement thereof can be used. Preferably, the target polynucleotides are short and/or fragmented polynucleotide molecules which are representative of the original nucleic acid population of the cell.

The target polynucleotides to be analyzed by the methods and compositions of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}$P, $^{35}$S, $^{14}$C, $^{15}$N and $^{125}$I. Fluorescent molecules suitable for the present invention include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41. Fluorescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.8.1.4. Hybridization to Microarrays

As described supra, nucleic acid hybridization and wash conditions are chosen so that the polynucleotide molecules to be analyzed by the invention (referred to herein as the "target polynucleotide molecules) specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B.V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

5.8.1.5. Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In preferred embodiments, target sequences, e.g., cDNAs or cRNAs, from two different cells are hybridized to the binding sites of the microarray. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA or cRNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, changes the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467–470, which is incorporated by reference in its entirety for all purposes. The scheme is equally applicable to labeling and detection of exons. An advantage of using target sequences, e.g., cDNAs or cRNAs, labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639–645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639–645. Alternatively, the fiber-optic bundle described by Ferguson et al., 1996, *Nature Biotech.* 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA and/or an exon expressed in an mRNA in two cells or cell lines is scored as perturbed (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of differences of an order of about 1.5 fold to about 3-fold.

It is, however, also advantageous to determine the magnitude of the relative difference in abundances for an mRNA and/or an exon expressed in an mRNA in two cells or in two cell lines. This can be carried out, as noted above, by calculating the ratio of the emission of the two fluorophores used for differential labeling, or by analogous methods that will be readily apparent to those of skill in the art.

5.8.2. Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, *Proc. Natl. Acad. Sci.* USA 93:659–663). Other methods statistically sample cDNA pools, such as by sequencing sufficient bases (e.g., 20–50 bases) in each of multiple cDNAs to identify each cDNA, or by sequencing short tags (e.g., 9–10 bases) that are generated at known positions relative to a defined mRNA end (see, e.g., Velculescu, 1995, *Science* 270:484–487).

5.9. Measurement of Other Aspects of the Biological State

In various embodiments of the present invention, aspects of the biological state other than the transcriptional state, such as the translational state, the activity state, or mixed aspects can be measured. Thus, in such embodiments, cellular constituent data 44 (FIG. 1) may include translational state measurements or even protein expression measurements. In fact, in some embodiments, rather than using gene expression interaction maps based on gene expression, protein expression interaction maps based on protein expression maps are used. Details of embodiments in which aspects of the biological state other than the transcriptional state are described in the following sections.

5.10. Translational State Measurements

Measurement of the translational state may be performed according to several methods. For example, whole genome monitoring of protein (i.e., the "proteome," Goffeau et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies. A Laboratory Manual*, Cold Spring Harbor, N.Y., which is incorporated in its entirety for all purposes). In a preferred embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Natl. Acad. Sci. USA* 93:1440–1445; Sagliocco et al., 1996, *Yeast* 12:1519–1533; Lander, 1996, *Science* 274:536–539. The resulting electropherograms can be analyzed by numerous techniques, including mass spectrometric techniques, Western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or overexpression of a specific gene.

5.11. Measuring Other Aspects of the Biological State

Even though methods of this invention are illustrated by embodiments involving gene expression or translation, the methods of the invention are applicable to any cellular constituent that can be monitored. For example, where activities of proteins can be measured, embodiments of this invention can use such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In some embodiments of the present invention, cellular constituent measurements are derived from cellular phenotypic techniques. One such cellular phenotypic technique uses cell respiration as a universal reporter. In one embodiment, 96-well microtiter plates, in which each well contains its own unique chemistry is provided. Each unique chemistry is designed to test a particular phenotype. Cells from the organism 46 (FIG. 1) of interest are pipetted into each well. If the cells exhibit the appropriate phenotype, they will respire and actively reduce a tetrazolium dye, forming a strong purple color. A weak phenotype results in a lighter color. No color means that the cells don't have the specific phenotype. Color changes may be recorded as often as several times each hour. During one incubation, more than 5,000 phenotypes can be tested. See, for example, Bochner et al., 2001, Genome Research 11, 1246–55.

In some embodiments of the present invention, the cellular constituents that are measured (gene expression data 44) are metabolites. Metabolites include, but are not limited to, amino acids, metals, soluble sugars, sugar phosphates, and complex carbohydrates. Such metabolites may be measured, for example, at the whole-cell level using methods such as pyrolysis mass spectrometry (Irwin, 1982, *Analytical Pyrolysis: A Comprehensive Guide*, Marcel Dekker, New York; Meuzelaar et al., 1982, *Pyrolysis Mass Spectrometry of Recent and Fossil Biomaterials*, Elsevier, Amsterdam), fourier-transform infrared spectrometry (Griffiths and de Haseth, 1986, *Fourier transform infrared spectrometry*, John Wiley, New York; Helm et al., 1991, J. Gen. Microbiol. 137, 69–79; Naumann et al., 1991, Nature 351, 81–82; Naumann et al., 1991, In: *Modern techniques for rapid microbiological analysis*, 43–96, Nelson, W. H., ed., VCH Publishers, New York), Raman spectrometry, gas chromotagraphy-mass spectroscopy (GC-MS) (Fiehn et al., 2000, Nature Biotechnology 18, 1157–1161, capillary electrophoresis (CE)/MS, high pressure liquid chromatography/ mass spectroscopy (HPLC/MS), as well as liquid chromatography (LC)-Electrospray and cap-LC-tandem-electrospray mass spectrometries. Such methods may be combined with established chemometric methods that make use of artificial neural networks and genetic programming in order to discriminate between closely related samples.

5.12. Exemplary Diseases

As discussed supra, the present invention provides an apparatus and method for associating a gene with a trait exhibited by one or more organisms in a plurality of organisms of a species (e.g., a single species). In some instances, the gene is associated with the trait by identifying a biological pathway in which the gene product participates. In some embodiments of the present invention, the trait of interest is a complex trait, such as a disease, e.g., a human disease. Exemplary diseases include allergies, asthma, and obsessive-compulsive disorder such as panic disorders, phobias, and post-traumatic stress disorders.

Exemplary diseases further include autoimmune disorders such as Addison's disease, alopecia areata, ankylosing spondylitis, antiphospholipid syndrome, Behcet's disease, chronic fatigue syndrome, Crohn's disease and ulcerative colitis, diabetes, fibromyalgia, Goodpasture syndrome, graft versus host disease, lupus, Meniere's disease, multiple sclerosis, myasthenia gravis, myositis, pemphigus vulgaris, primary biliary cirrhosis, psoriasis, rheumatic fever, sarcoidosis, scleroderma, vasculitis, vitiligo, and Wegener's granulomatosis.

Exemplary diseases further include bone diseases such as achondroplasia, bone cancer, fibrodysplasia ossificans progressiva, fibrous dysplasia, legg calve perthes disease, myeloma, osteogenesis imperfecta, osteomyelitis, osteoporosis, paget's disease, and scoliosis. Exemplary diseases include cancers such as bladder cancer, bone cancer, brain tumors, breast cancer, cervical cancer, colon cancer, gynecologic cancers, Hodgkin's disease, kidney cancer, laryngeal cancer, leukemia, liver cancer, lung cancer, lymphoma, oral cancer, ovarian cancer, pancreatic cancer, prostate cancer, skin cancer, and testicular cancer.

Exemplary diseases further include genetic disorders such as achondroplasia, achromatopsia, acid maltase deficiency, adrenoleukodystrophy, Aicardi syndrome, alpha-1 antitrypsin deficiency, androgen insensitivity syndrome, Apert syndrome, dysplasia, ataxia telangiectasia, blue rubber bleb nevus syndrome, canavan disease, Cri du chat syndrome, cystic fibrosis, Dercum's disease, fanconi anemia, fibrodysplasia ossificans progressiva, fragile x syndrome, galactosemia, gaucher disease, hemochromatosis, hemophilia, Huntington's disease, Hurler syndrome, hypophosphatasia, klinefelter syndrome, Krabbes disease, Langer-Giedion syndrome, leukodystrophy, long qt syndrome, Marfan syndrome, Moebius syndrome, mucopolysaccharidosis (mps), nail patella syndrome, nephrogenic, diabetes insipidus, neurofibromatosis, Niemann-Pick disease, osteogenesis imperfecta, porphyria, Prader-Willi syndrome, progeria, proteus syndrome, retinoblastoma, Rett syndrome, rubinstein-taybi syndrome, Sanfilippo syndrome, Shwachman syndrome, sickle cell disease, Smith-Magenis syndrome, Stickler syndrome, Tay-Sachs, thrombocytopenia absent radius (tar) syndrome, Treacher collins syndrome, trisomy, tuberous sclerosis, Turner's syndrome, urea cycle disorder, Von Hippel-Lindau disease, Waardenburg syndrome, Williams syndrome, and Wilson's disease.

Exemplary diseases further include angina pectoris, dysplasia, atherosclerosis/arteriosclerosis, congenital heart disease, endocarditis, high cholesterol, hypertension, long qt syndrome, mitral valve prolapse, postural orthostatic tachycardia syndrome, and thrombosis.

5.13. Linkage Analysis

This section describes a number of standard quantitative trait locus (QTL) linkage analysis algorithms that can be used in various embodiments of processing step 210 (FIG. 2). The purpose of these algorithms is to identify QTL for a phenotypic trait exhibited by one or more organisms 46. A QTL is a region of a genome of a species that is responsible for a percentage of variation in a phenotypic trait in the species under study. A QTL is identified by comparing genotypes of organisms in a group to a phenotype exhibited by the group using pedigree data. The genotype of each organism 46 at each marker in a plurality of markers in a genetic map 78 is compared to a given phenotype of each organism 46. A genetic map is created by placing genetic markers in genetic (linear) map order so that the relationships between markers are understood. The information gained from knowing the relationships between markers that is provided by a marker map provides the setting for addressing the relationship between QTL effect and QTL location. Exemplary markers include single nucleotide polymorphisms that arise in a given species.

It will be appreciated that the present invention provides no limitation on the type of phenotypic data that can be used to perform QTL analysis. The phenotypic data can, for example, represent a series of measurements for a quantifiable phenotypic trait in a collection of organisms. Such quantifiable phenotypic traits may include, for example, tail length, life span, eye color, size and weight. Alternatively, the phenotypic data can be in a binary form that tracks the absence or presence of some phenotypic trait. As an example, a "1" may indicate that a particular species of the organism of interest possesses a given phenotypic trait and a "0" may indicate that a particular species of the organism of interest lacks the phenotypic trait. The phenotypic trait can be any form of biological data that is representative of the phenotype of each organism 46. Because the phenotypic traits are quantified, they are often referred to as quantitative phenotypes.

In order to provide the necessary genotypic data for the QTL analysis, the genotype of each marker in the genetic marker map 78 is determined for each organism 46. Representative forms of genotypes include, but are not limited to, single nucleotide polymorphisms, microsatellite markers, restriction fragment length polymorphisms, short tandem repeats, sequence length polymorphisms, and DNA methylation patterns.

Linkage analysis requires pedigree data for each organism 46 in order to statistically model the segregation of markers. In some embodiments, populations under study are constructed from populations that originate from homozygous, inbred parental lines. The resulting $F_1$ lines will be heterozygous at all loci. From the $F_1$ population, crosses are made. Exemplary crosses include backcrosses and $F_2$ intercrosses. Thus, in some embodiments of the present invention, organisms 46 represent a population, such as an $F_2$ population, and pedigree data for the F2 population is known. This pedigree data is used to compute logarithm of the odds (LOD) scores, as discussed in further detail below.

Linkage analyses, such as interval mapping, use the genetic map as the framework for location of QTL for any given quantitative trait. The intervals that are defined by ordered pairs of markers are searched in increments (for example, 2 cM), and statistical methods are used to test whether a QTL is likely to be present at the location within the interval. In one embodiment, quantitative genetic analysis 210 (FIG. 2) statistically tests for a single QTL at each increment across the ordered markers in the genetic map. The results of the tests are expressed as LOD scores, which compares the evaluation of the likelihood function under a null hypothesis (no QTL) with the alternative hypothesis (QTL at the testing position) for the purpose of locating probable QTL. More detail on LOD scores is found in Section 5.4. Interval mapping searches through the ordered genetic markers in a systematic, linear (one-dimensional) fashion, testing the same null hypothesis and using the same form of likelihood at each increment.

In one embodiment of the present invention, linkage analysis comprises QTL interval mapping in accordance with algorithms derived from those first proposed by Lander and Botstein, 1989, "Mapping mendelian factors underlying quantitative traits using RFLP linkage maps," Genetics 121: 185–199. The principle behind interval mapping is to test a model for the presence of a QTL at many positions between two mapped marker loci. The model is fit, and its goodness is tested using the method of maximum likelihood. The maximum likelihood theory assumes that when a QTL is located between two biallelic markers, the genotypes (i.e. AABB, AAbb, aaBB, aabb for doubled haploid progeny) each contain mixtures of quantitative trait locus (QTL) genotypes. Maximum likelihood involves searching for QTL parameters that give the best approximation for quantitative trait distributions that are observed for each marker class. Models are evaluated by computing the likelihood of the observed distributions with and without fitting a QTL effect.

In some embodiments of the present invention, processing step 210 is performed using the algorithm of Lander, as implemented in programs such as GeneHunter. See, for example, Kruglyak et al., 1996, Parametric and Nonparametric Linkage Analysis: A Unified Multipoint Approach, American Journal of Human Genetics 58:1347–1363, Kruglyak and Lander, 1998, Journal of Computational Biology 5:1–7; Kruglyak, 1996, American Journal of Human Genetics 58, 1347–1363. In such embodiments, unlimited markers may be used by pedigree size is constrained. In other embodiments, the MENDEL is used. (See http://bimas.dcrt-.nih.gov/linkage/ltools.html). In such embodiments, the size of the pedigree can be unlimited but the number of markers that may be used in constrained. Those of skill in the art will appreciate that there are several other programs and algorithms that may be used in processing step 210 and all such programs and algorithms are included within the scope of the present invention.

In some embodiments of the present invention, processing step 210 (FIG. 2) is a regression mapping that gives estimates of QTL position and effect that are similar to those given by the maximum likelihood method. The approximation between regression mapping and maximum likelihood deviates only at places where there are large gaps in the genetic marker map, or many missing genotypes. Regression mapping is essentially the same as the method of basic QTL analysis (regression on coded marker genotypes) except that phenotypes are regressed on QTL genotypes. Since the QTL genotypes are unknown, they are replaced by probabilities estimated from the nearest flanking markers. See, e.g., Haley and Knott, 1992, "A simple regression method for mapping quantitative trait loci in line crosses using flanking markers," Heredity 69, 315–324.

Many known programs can be used to perform processing step 210 (FIG. 2) in accordance with this aspect of the invention. One such program is MapMaker/QTL, which is the companion program to MapMaker and is the original QTL mapping software. MapMaker/QTL analyzes F2 or backcross data using standard interval mapping (Lander and Botstein, Id.). Another such program is QTL Cartographer, which performs single-marker regression, interval mapping (Lander and Botstein, Id.), and composite interval mapping (Zeng, 1993, PNAS 90: 10972–10976; and Zeng, 1994, Genetics 136: 1457–1468). QTL Cartographer permits analysis from F2 or backcross populations. QTL Cartographer is available from http://statgen.ncsu.edu/qtlcart/cartographer.html (North Carolina State University). Another program that can be used by processing step 114 is Qgene, which performs QTL mapping by either single-marker regression or interval regression (Martinez and Curnow 1994 Heredity 73:198–206). Using Qgene, eleven different population types (all derived from inbreeding) can be analyzed. Qgene is available from http://www.qgene.org/. Yet another program is MapQTL, which conducts standard interval mapping (Lander and Botstein, Id.), multiple QTL mapping (MQM) (Jansen, 1993, Genetics 135: 205–211; Jansen, 1994, Genetics 138: 871–881), and nonparametric mapping (Kruskal-Wallis rank sum test). MapQTL can analyze a variety of pedigree types including outbred pedigrees (cross pollinators). MapQTL is available from Plant Research International, Plant Research International, P.O. Box 16, 6700 AA Wageningen, The Netherlands; http://www.plant.wageningen-ur.nl/default.asp?section=products). Yet another program that may be used in some embodiments of processing step 210 is Map Manager QT, which is a QTL mapping program (Manly and Olson, 1999, Mamm Genome 10: 327–334). Map Manager QT conducts single-marker regression analysis, regression-based simple interval mapping (Haley and Knott, 1992, Heredity 69, 315–324), composite interval mapping (Zeng 1993, PNAS 90: 10972–10976), and permutation tests. A description of Map Manager QT is provided by the reference Manly and Olson, 1999, Overview of QTL mapping software and introduction to Map Manager QT, Mammalian Genome 10: 327–334.

Yet another program that may be used in some embodiments of processing step 210 is MultiCross QTL, which maps QTL in plant populations. MultiCross QTL uses a linear regression-model approach and handles different methods such as interval mapping, all-marker mapping, and multiple QTL mapping with cofactors. The program can handle a wide variety of simple mapping populations for inbred and outbred species. MultiCross QTL is available from Unité de Biométrie et Intelligence Artificielle, INRA, 31326 Castanet Tolosan, France.

Still another program that may be used for processing step 210 is the QTL Café, The program can analyze most populations derived from pure line crosses such as F2 crosses, backrosses, recombinant inbred lines, and doubled haploid lines. QTL Café incorporates a Java implementation of Haley & Knotts' flanking marker regression as well as Marker regression, and can handle multiple QTLs. The program allows three types of QTL analysis single marker ANOVA, marker regression (Kearsey and Hyne, 1994, Theor. Appl. Genet., 89: 698–702), and interval mapping by regression, (Haley and Knott, 1992, Heredity 69: 315–324). QTL Cafe is available from http://web.bham.ac.uk/g.g.seaton/.

Yet another program that may be used for processing step 210 is MAPL, which performs QTL analysis by either interval mapping (Hayashi and Ukai, Theor. Appl. Genet. 87:1021–1027) or analysis of variance. Different population types including F2, back-cross, recombinant inbreds derived from F2 or back-cross after a given generations of selfing, and silkworm F2 can be analyzed. Automatic grouping and ordering of numerous markers by metric multidimensional scaling is possible. MAPL is available from the Institute of Statistical Genetics on Internet (ISGI), Yasuo, UKAI, http://peach.ab.a.u-tokyo.ac.jp/~ukai/.

Another program that may be used for processing step 210 is R/qtl. This program provides an interactive environment for mapping QTLs in experimental crosses. R/qtl makes uses of the hidden Markov model (HMM) technology for dealing with missing genotype data. R/qtl has implemented many HMM algorithms, with allowance for the presence of genotyping errors, for backcrosses, intercrosses, and phase-known four-way crosses. R/qtl includes facilities for estimating genetic maps, identifying genotyping errors, and performing single-QTL genome scans and two-QTL, two-dimensional genome scans, by interval mapping with Haley-Knott regression, and multiple imputation. R/qtl is available from Karl W. Broman, Johns Hopkins University, http://biosun01.biostat.jhsph.edu/~kbroman/qtl/.

5.14. Association Analysis

This section describes a number of standard association studies that can be used in various embodiments of processing step 210 (FIG. 2). Association studies test whether a disease and an allele show correlated occurrence in a population, whereas linkage studies (Section 5.13, supra) test whether they show correlated transmission in a pedigree. In some instances, association analyses are case-control studies based on a comparison of unrelated affected and unaffected individuals from a population. An allele A at a gene of interest is said to be associated with a quantitative phenotype if it occurs as significantly higher frequency among affected compared with control individuals. Although association studies can be performed for any random DNA polymorphism, they are most meaningful when applied to functionally significant variations in genes having a clear biological relation to the trait. More information on association analysis is found in Lander and Schork, 1994, Science 265: 2037.

Association studies have been used to implicate the HLA complex in the etiology of autoimmune diseases. The allele HLA-B27, for example, occurs in 90% of patients with ankylosing spondylitis but only 9% of the general population. See Ryder, Anderson, Svejgaard, Eds. *HLA and Disease Registry, Third Report* (Munksgaard, Copenhagen, 1979). Furthermore, there are seveal HLA associations involving such diseases as type I diabetes, rheumatoid arthritis, multiple sclerosis, celiac disease, and systemic lupus erythromatosus. See, e.g., Braun, 1979, *HLA and Disease* (CRC, Boca Raton, Fla.).

In some embodiments of the present invention, processing step 210 (FIG. 2) is an association analysis. In a specific analysis, processing step 210 is an association analysis in which a control group is created using the haplotype relative risk method (also known as the affected family-based control method). In the haplotype relative risk method, an "internal control" is created for allele frequencies. To illustrate the use of an "internal control" consider the case in which the parents have genotypes $A_1/A_2$ and $A_3/A_4$ and the affected individual has genotype $A_1/A_3$, then the genotype $A_2/A_4$ (consisting of the two alleles that the affected individual did not inherit) provides an "artificial control" that is well matched for ethnic ancestry. More details on the use of an "internal control" are found in the following exemplary references, Falk and Rubinstein, 1987, Ann. Hum. Genet. 51: 227; Thompson et al., 1989, Genet. Epidemiol. 6: 43, Ott, *Analysis of Human Genetic Linkage*, first edition, Baltimore, Md., John Hopkins University Press, 127; Terwilliger and Ott, 1992, Hum. Hered. 42: 337; and Knapp et al., 1993, Am. J. Hum. Genet. 52: 1085.

5.15. Complex Traits

In some embodiments of the present invention, the term "complex trait" refers to any clinical trait T that does not exhibit classic Mendelian inheritance. In some embodiments, the term "complex trait" refers to a trait that is affected by two or more gene loci. In some embodiments, the term "complex trait" refers to a trait that is affected by two or more gene loci in addition to one or more factors including, but not limited to, age, sex, habits, and environment. See, for example, Lander and Schork, 1994, *Science* 265: 2037. Such "complex" traits include, but are not limited to, susceptibilities to heart disease, hypertension, diabetes, obesity, cancer, and infection. Complex traits arise when the simple correspondence between genotype and phenotype breaks down, either because the same genotype can result in different phenotypes (due to the effect of chance, environment, or interaction with other genes) or different genotypes can result in the same phenotype.

In some embodiments, a complex trait is one in which there exists no genetic marker that shows perfect cosegregation with the trait due to incomplete penetrance, phenocopy, and/or nongenetic factors (e.g., age, sex, environment, and affect or other genes). Incomplete penetrance means that some individuals who inherit a predisposing allele may not manifest the disease. Phenocopy means that some individuals who inherit no predisposing allele may nonetheless get the disease as a result of environmental or random causes. Thus, the genotype at a given locus may affect the probability of disease, but not fully determine the outcome. The penetrance function f(G), specifying the probability of disease for each genotype G, may also depend on nongenetic factors such as age, sex, environment, and other genes. For example, the risk of breast cancer by ages 40, 55, and 80 is 37%, 66%, and 85% in a woman carrying a mutation at the BCRA1 locus as compared with 0.4%, 3%, and 8% in a noncarrier (Easton et al., 1993, *Cancer Surv.* 18: 1995; Ford et al., 1994, *Lancet* 343: 692). In such cases, genetic mapping is hampered by the fact that a predisposing allele may be present in some unaffected individuals or absent in some affected individuals.

In some embodiments a complex trait arises because any one of several genes may result in identical phenotypes (genetic heterogeneity). In cases where there is genetic heterogeneity, it may be difficult to determine whether two patients suffer from the same disease for different genetic reasons until the genes are mapped. Examples of complex diseases that arise due to genetic heterogeneity in humans include polycystic kidney disease (Reeders et al., 1987, *Human Genetics* 76: 348), early-onset Alzheimer's disease (George-Hyslop et al., 1990, *Nature* 347: 194), maturity-onset diabetes of the young (Barbosa et al., 1976, *Diabete Metab.* 2: 160), hereditary nonpolyposis colon cancer (Fishel et al., 1993, *Cell* 75: 1027) ataxia telangiectasia (Jaspers and Bootsma, 1982, *Proc. Natl. Acad. Sci. U.S.A.* 79: 2641), obesity, nonalcoholic steatohepatitis (NASH) (James & Day, 1998, *J. Hepatol.* 29: 495–501), nonalcoholic fatty liver (NAFL) (Younossi, et al., 2002, Hepatology 35, 746–752), and xeroderma pigmentosum (De Weerd-Kastelein, *Nat. New Biol.* 238: 80). Genetic heterogeneity hampers genetic mapping, because a chromosomal region may cosegregate with a disease in some families but not in others.

In still other embodiments, a complex trait arises due to the phenomenon of polygenic inheritance. Polygenic inheritance arises when a trait requires the simultaneous presence of mutations in multiple genes. An example of polygenic inheritance in humans is one form of retinitis pigmentosa, which requires the presence of heterozygous mutations at the peripherin/RDS and ROM1 genes (Kajiwara et al., 1994, *Science* 264: 1604). It is believed that the proteins coded by RDS and ROM1 are thought to interact in the photoreceptor outer pigment disc membranes. Polygenic inheritance complicates genetic mapping, because no single locus is strictly required to produce a discrete trait or a high value of a quantitative trait.

In yet other embodiments, a complex trait arises due to a high frequency of disease-causing allele "D". A high frequency of disease-causing allele will cause difficulties in mapping even a simple trait if the disease-causing allele occurs at high frequency in the population. That is because the expected Mendelian inheritance pattern of disease will be confounded by the problem that multiple independent copies of D may be segregating in the pedigree and that some individuals may be homozygous for D, in which case one will not observe linkage between D and a specific allele at a nearby genetic marker, because either of the two homologous chromosomes could be passed to an affected offspring. Late-onset Alzheimer's disease provides one example of the problems raised by high frequency disease-causing alleles. Initial linkage studies found weak evidence of linkage to chomosome 19q, but they were dismissed by many observers because the LOD score (logarithm of the likelihood ratio for linkage) remained relatively low, and it was difficult to pinpoint the linkage with any precision (Pericak-Vance et al., 1991, *Am J. Hum. Genet.* 48: 1034). The confusion was finally resolved with the discovery that the apolipoprotein E type 4 allele appears to be the major causative factor on chromosomeb 19. The high frequency of the allele (about 16% in most populations) had interfered with the traditional linkage analysis (Corder et al., 1993, *Science* 261: 921). High frequency of disease-causing alleles becomes an even greater problem if genetic heterogeneity is present.

5.16. EXAMPLES

The following examples are presented by way of illustration of the previously described invention and are not limiting of that description.

5.16.1. Exemplary Sources of Genotype and Pedigree Data

Mice. The methods of the present invention are applicable to any living organism in which genetic variation can be tracked. Therefore, by way of example, genotype and/or pedigree data 68 (FIG. 1) is obtained from experimental crosses or a human population in which genotyping information and relevant clinical trait information is provided. One such experimental design for a mouse model for complex human diseases is given in FIG. 9. In FIG. 9, there are two parental inbred lines that are crossed to obtain an $F_1$ generation. The $F_1$ generation is intercrossed to obtain an $F_2$ generation. At this point, the $F_2$ population is genotyped and physiologic phenotypes for each $F_2$ in the population are determined to yield genotype and pedigree data 68. These same determinations are made for the parents as well as a sampling of the $F_1$ population.

*Zea mays*. Data based on an experimental cross done in *Zea mays* are given in FIG. 10. This particular cross differs from the mouse system discussed in conjunction with FIG. 9 in that the $F_2$ generation was selfed to obtain an $F_3$ generation. Then pools of $F_3$ plants were derived from the same $F_2$ parent to obtain phenotype information (physiologic phenotypes as well as the gene expression phenotypes) while the genotype information came from the $F_2$ generation. While this provided for slightly different statistical methods to analyze the data, the concept is still the same (integrating gene expression, genetics and other phenotype data to identify genes and pathways controlling for the traits of interest).

To perform QTL analysis the following assumptions were made. The trait for an $F_y$ plant was assumed to depend on the QTL genotype of the $F_y$: $y_{QQ} \sim f(\mu_1, \sigma_1^2)$, $y_{Qq} \sim f(\mu_2, \sigma_2^2)$, $y_{qq} \sim f(\mu_3, \sigma_3^2)$. For a putative QTL location, the probability of QQ, Pr(QQ), the probability of Qq, Pr(Qq), and the probability of qq, Pr(qq) were estimated using the genotypes at flanking markers, the marker map and the breeding design.5.

Due to the nature of biological variation, it was expected that genes, underlying genetic control for the abundance of mRNA transcripts, will interact in a synergistic fashion. There are numerous methods for the detection of such gene-gene interaction. One such method utilizes linkage information for each of two genes and assesses how this information correlates among individuals (see Cox et al., 1999, Loci on chromosomes 2 (NIDDM1) and 15 interact to increase susceptibility to diabetes in Mexican Americans, *Nat Genet.* 21(2):213–215). For the $i^{th}$ of N $F_{2:3}$ observations, let $Y_{1i}$ be the likelihood for the presence of a QTL at location 1 given the marker data for the $i^{th}$ $F_2$ individual and the phenotype for their $F_3$ pool. Likewise, let $Y_{2i}$ be the corresponding information for the presence of a QTL at location 2. The correlation between the variables $Y_{1i}$ and $Y_{2i}$ is estimated as:

$$r_{12} = \frac{\sum_{i=1}^{N}(Y_{1i} - \overline{Y}_1)(Y_{2i} - \overline{Y}_2)}{\sqrt{(Y_{1i} - \overline{Y}_1)^2(Y_{2i} - \overline{Y}_2)^2}}$$

where, $$\overline{Y}_1 = \frac{1}{N}\sum_{i=1}^{N} Y_{1i} \text{ and } \overline{Y}_1 = \frac{1}{N}\sum_{i=1}^{N} Y_{1i}.$$

Statistical significance was assessed using the t-distribution with N−2 degrees of freedom. The nominal P-value for the test was determined by the probability that a random variable from this distribution exceeds the absolute value of the following test statistic:

$$t = \frac{r_{12}}{\sqrt{(1 - r_{12}^2)/(N-2)}}$$

Due to the large-scale testing necessary to assess all possible gene-gene interactions, multiple testing corrections are preferably applied. One such multiple testing correction method is the Bonferroni adjustment that adjusts nominal p-values by multiplying by the total number of tests performed.

Significant correlations between linkage information for two unlinked loci provide insight into their mechanism for interaction. In particular, loci with positive correlation indicate two genes are influencing transcript abundance of the specific mRNA in the same biological pathway or in interacting biological pathways. On the other hand, loci with negative correlation provide evidence of disease heterogeneity so that one gene influences variation in mRNA abundance in one set of observations while a separate gene influences variation in mRNA abundance in other observations. The strength of the evidence for gene-gene interaction is further assessed by studying the genotype distribution for the two loci tested. Due to the large number of positions tested, it is possible that the interaction could be due to correlated genotypes between the two loci. This can happen by chance despite the loci being unlinked. The genotype distributions for non-independence were tested using Fisher's exact test. Gene-gene interactions that did not demonstrate non-independence were considered stronger evidence for biological interaction.

Human populations. The present invention is not constrained to model systems, but can be applied directly to human populations. For example, pedigree and other genotype information for the Ceph family is publicly available (Center for Medical Genetics, Marshfield, Wis.), and lymphoblastoid cell lines from individuals in these families can be purchased from the Coriell Institute for Medical Research (Camden, N.J.) and used in the expression profiling experiments of the instant invention. The plant, mouse, and human populations discussed in this Section represent non-limiting examples of genotype and/or pedigree for use in the present invention.

5.16.2. Identification of Regions that Broadly Control Transcription

The genome-wide consideration of all genes as quantitative traits, representation of individual QTL analysis results in a database, and summarizing the degree of overlap among all genes at all positions where a QTL analysis was run enables the identification of regions that very broadly control transcription. For a given organism, this allows for the identification of regions that potentially control for basal-level transcription levels across most genes that are expressed. FIG. 12 highlights this utility in *Zea mays* data measured across 76 ear-leaf tissues. There are three curves represented in this plot. Along the x-axis are all intervals across the corn genome considered in the QTL analyses for each gene represented on the array. Along the y-axis are the counts for the number of genes that had QTL at the designated location that exceeded predefined LOD-score thresholds.

Curve 1202 represents counts of the number of QTL between a LOD score of 3.0 and 6.0 at the designated locations, while curve 1204 gives the counts for QTL between 4.0 and 6.0, and curve 1206 gives the counts for QTL greater than or equal to 6.0. Approximately 25,000 genes were considered in this analysis. Of these 25,000 genes, approximately 15,000 had at least one QTL exceeding a LOD score of 4.0. As indicated in FIG. 12, nearly 9,000 genes (of the 15,000) had QTL with LODs between 4.0 and 6.0 at a single locus on chromosome 5 (the location just right of 40 in FIG. 12). Therefore, nearly 60% of the genes with a significant QTL had transcription levels that are significantly controlled by the chromosome 5 locus. It is further noted that when the threshold for linkage is increased to 6.0, all of the QTL hotspots disappear, indicating that those genes with the most significant genetic signature are not under the control of the QTL hotspots.

In general, the genome-wide QTL analysis allowed for the division of genes into two classes: 1) those that have a moderate genetic signature, with moderate linkages to a small number of loci, and that appear to be significantly correlated with a significant number of other genes also under moderate control of the same QTL and 2) those genes with a strong genetic signature, but are not very highly correlated with many other genes. Those genes that have a moderate genetic signature are the genes that are controlled. Those genes that have a strong genetic signature are the controlling genes that behave more independently with respect to other genes than genes in the controlled class. These classes evidence an important utility that is provided by the methods of the present invention, which is the identification of those genes that control biological pathways and/or interactions between biological pathways, and the separation of these genes from genes that are simply responding to the signals propagated by the potentially small set of genes.

The results provided in this section are counterintuitive to the current state of pattern recognition for microarray data. That is, current thinking is to identify those expression patterns over a number of relevant conditions that are significantly co-regulated (almost all forms of cluster analysis and other pattern detection schemes depend on this). On the other hand, this example demonstrates that the most strongly genetically controlled genes are actually least similar, least co-regulated with other genes, mainly because they are behaving somewhat independently of all other genes. The methods of the present invention allow for the identification of this class of genes, and these genes further elucidate control of pathways and disease etiology since they are ostensibly important to the proper functioning of so many pathways.

5.16.3. Identifying Genes Under Genetic Control in Small Populations

The methods of the present invention may be used to identify targets for any disease in a population by identifying those genes under genetic control in relatively small population sizes. For example, FIG. 13 gives the histogram for p-values of segregation analyses performed on 2,726 genes across 4 Ceph families. A significant p-value indicates that there is evidence that the transcription levels are segregating in the families, indicating a significant heritability component to the trait values. In this case, 29% of the genes tested have significant p-values, far above the number expected by chance, which is 5%. Randomizing expression values across individuals resulted in fewer than 1% of the genes exceeding the 0.05 significance level, again suggesting that the observed 29% number is highly significant. Because significant heritabilities were detected in 29% of these genes with such a small sample size, these genes are presumably more highly controlled at the genetic level, and so they are more natural candidates for complex disease traits since variation in these traits can be expected to cause detectable phenotypes.

6. REFERENCES CITED

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a computer readable storage medium. For instance, the computer program product could contain the program modules shown in FIG. 1. These program modules may be stored on a CD-ROM, magnetic disk storage product, or any other computer readable data or program storage product. The software modules in the computer program product may also be distributed electronically, via the Internet or otherwise, by transmission of a computer data signal (in which the software modules are embedded) on a carrier wave.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for identifying members of a biological pathway in a species, the method comprising:
    (a) clustering quantitative trait locus data from a plurality of quantitative trait locus analyses to form a quantitative trait locus interaction map, wherein
        each quantitative trait locus analysis in said plurality of quantitative trait locus analyses is performed for a gene in a plurality of genes in the genome of said species using a genetic marker map and a quantitative trait in order to produce said quantitative trait locus data, wherein, for each quantitative trait locus analysis, said quantitative trait comprises an expression statistic for the gene for which the quantitative trait locus analysis has been performed, for each organism in a plurality of organisms that are members of said species; and wherein
        said genetic marker map is constructed from a set of genetic markers associated with said species; and
    (b) identifying a cluster of genes in said quantitative trait locus interaction map, thereby identifying members of said biological pathway.

2. The method of claim 1, which further comprises, prior to said clustering, constructing said genetic marker map from said set of genetic markers associated with said plurality of organisms.

3. The method of claim 1, which further comprises, prior to said clustering, performing each said quantitative trait locus analysis in said plurality of quantitative trait locus analyses.

4. The method of claim 3, which further comprises, prior to said performing step, a step of constructing said genetic marker map from said set of genetic markers associated with said plurality of organisms.

5. The method of claim 1 wherein said expression statistic for said gene is computed by transforming an expression level measurement of said gene from each organism in said plurality of organisms.

6. The method of claim 5 wherein said transforming comprises normalizing the expression level measurement of said gene in order to form said expression statistic.

7. The method of claim 6 wherein normalizing the expression level measurement of said gene in order to form said expression statistic is performed by a normalization technique selected from the group consisting of Z-score of intensity, median intensity, log median intensity, Z-score standard deviation log of intensity, Z-score mean absolute deviation of log intensity, calibration DNA gene set, user normalization gene set, ratio median intensity correction, and intensity background correction.

8. The method of claim 1 wherein each said quantitative trait locus analysis comprises:
(i) testing for linkage between a position in a chromosome, in the genome of said plurality of organisms, and the quantitative trait used in the quantitative trait locus analysis;
(ii) advancing the position in said chromosome by an amount;
(iii) repeating steps (i) and (ii) until an end of the chromosome is reached.

9. The method of claim 8 wherein steps (i) through (iii) are repeated for each chromosome in said genome.

10. The method of claim 8 wherein said amount is less than 100 centiMorgans.

11. The method of claim 8 wherein said amount is less than 10 centiMorgans.

12. The method of claim 8 wherein said amount is less than 5 centiMorgans.

13. The method of claim 8 wherein said amount is less than 2.5 centiMorgans.

14. The method of claim 8 wherein said testing comprises performing linkage analysis or association analysis.

15. The method of claim 1 wherein said quantitative trait locus data produced from each respective quantitative trait locus analysis comprises a logarithmic of the odds score computed at each said position.

16. The method of claim 1 wherein
each quantitative trait locus analysis in said plurality of quantitative trait locus analyses generates a quantitative trait locus vector and
said quantitative trait locus vector represents the gene for which said quantitative trait locus analysis has been performed, and
said quantitative trait locus vector comprises a statistical score for each position tested by the quantitative trait locus analysis; and wherein
said statistical score represents a correlation between (i) the expression statistic for the gene and (ii) variation in the genome in said plurality of organisms at said position.

17. The method of claim 16 wherein said statistical score is a logarithmic of the odds score.

18. The method of claim 16 wherein said cluster of genes are those genes that are represented by a gene analysis vector in said quantitative trait locus interaction map that shares a correlation coefficient with another gene analysis vector in said quantitative trait locus interaction map that is higher than 75% of all correlation coefficients computed between gene analysis vectors in said quantitative trait locus interaction map.

19. The method of claim 16 wherein said cluster of genes are those genes that are represented by a gene analysis vector in said quantitative trait locus interaction map that shares a correlation coefficient with another gene analysis vector in said quantitative trait locus interaction map that is higher than 85% of all correlation coefficients computed between gene analysis vectors in said quantitative trait locus interaction map.

20. The method of claim 16 wherein said cluster of genes are those genes that are represented by a gene analysis vector in said quantitative trait locus interaction map that shares a correlation coefficient with another gene analysis vector in said quantitative trait locus interaction map that is higher than 95% of all correlation coefficients computed between gene analysis vectors in said quantitative trait locus interaction map.

21. The method of claim 16 wherein said clustering step (a) comprises clustering each said quantitative trait locus vector.

22. The method of claim 1 wherein a similarity metric is in said clustering step (a) and wherein said similarity metric is a Euclidean distance, a squared Euclidean distance, a Euclidean sum of squares, a Manhattan metric, a Pearson correlation coefficient, or a squared Pearson correlation coefficient, and wherein the similarity metric is computed between quantitative trait locus vector pairs.

23. The method of claim 1 wherein said clustering step (a) is performed using a nonparametric clustering technique.

24. The method of claim 1 wherein said clustering step (a) comprises applying a hierarchical clustering technique, applying a k-means technique, applying a fuzzy k-means technique, applying a Jarvis-Patrick clustering, applying a self-organizing map technique, or applying a neural network technique.

25. The method of claim 1 wherein said clustering step (a) comprises applying an agglomerative clustering procedure.

26. The method of claim 25 wherein said agglomerative clustering procedure is a nearest-neighbor algorithm, a farthest-neighbor algorithm, an average linkage algorithm, a centroid algorithm, or a sum-of-squares algorithm.

27. The method of claim 1 wherein said clustering step (a) comprises applying a divisive clustering procedure.

28. The method of claim 1 which further comprises constructing a gene expression cluster map, wherein said gene expression cluster map comprises a plurality of gene expression vectors and each gene expression vector in said plurality of gene expression vectors comprises an expression statistic for a gene in said plurality of genes.

29. The method of claim 28 wherein said constructing said gene expression cluster map comprises:
computing a plurality of correlation coefficients, wherein each correlation coefficient in said plurality of correlation coefficients is computed between a pair of gene expression vectors in said plurality of gene expression vectors; and
clustering said plurality of gene expression vectors using said plurality of correlation coefficients.

30. The method of claim 29 wherein each correlation coefficient in said plurality of correlation coefficients is a Pearson correlation coefficient.

31. The method of claim 29 wherein said clustering of the plurality of gene expression vectors comprises applying a hierarchical clustering technique, applying a k-means technique, applying a fuzzy k-means technique, applying a Jarvis-Patrick clustering, applying a self-organizing map technique, or applying a neural network technique.

32. The method of claim 29 wherein said clustering of the plurality of gene expression vectors comprises applying an agglomerative clustering procedure.

33. The method of claim 32 wherein said agglomerative clustering procedure is a nearest-neighbor algorithm, a farthest-neighbor algorithm, an average linkage algorithm, a centroid algorithm, or a sum-of-squares algorithm.

34. The method of claim 29 wherein said clustering of the plurality of gene expression vectors comprises applying a divisive clustering procedure.

35. The method of claim 28 wherein said constructing said gene expression cluster map comprises:

computing a plurality of metrics, wherein each metric in said plurality of metrics is computed between a gene expression vector pair in said plurality of gene expression vectors; and clustering said plurality of gene expression vectors based on said plurality of metrics in order to form said gene expression cluster map.

36. The method of claim 35 wherein each metric in said plurality of metrics is selected from the group consisting of a Euclidean distance, a squared Euclidean distance, a Euclidean sum of squares, a Manhattan metric, a Pearson correlation coefficient, and a squared Pearson correlation coefficient.

37. The method of claim 35 wherein said clustering of the plurality of gene expression vectors comprises applying a hierarchical clustering technique, applying a k-means technique, applying a fuzzy k-means technique, applying a Jarvis-Patrick clustering, applying a self-organizing map technique, or applying a neural network technique.

38. The method of claim 35 wherein said clustering of the plurality of gene expression vectors comprises applying an agglomerative clustering procedure.

39. The method of claim 38 wherein said agglomerative clustering procedure is a nearest-neighbor algorithm, a farthest-neighbor algorithm, an average linkage algorithm, a centroid algorithm, or a sum-of-squares algorithm.

40. The method of claim 38 wherein said clustering of the plurality of gene expression vectors comprises applying a divisive clustering procedure.

41. The method of claim 1, the method further comprising
(c) determining a clinical trait associated with said biological pathway.

42. The method of claim 41 wherein said determining step (c) comprises performing quantitative trait locus analysis using said clinical trait and said genetic marker map, wherein, when QTL arising from the quantitative trait locus analysis using said clinical trait colocalize with QTL associated with said cluster of genes, said clinical trait is associated with said biological pathway.

43. The method of claim 41 wherein said determining step (c) comprises correlating gene annotation information for a gene in said cluster of genes with said clinical trait.

44. The method of claim 41 wherein said determining step (c) comprises performing quantitative trait locus analysis using said clinical trait and said genetic marker map, wherein, when the results of the quantitative trait locus analysis using said clinical trait cocluster with said cluster of genes, said clinical trait is associated with said biological pathway.

45. The method of claim 1 wherein said method further comprises using said cluster of genes in a multivariate analysis to determine whether said genes are genetically interacting.

46. The method of claim 1 wherein said plurality of genes comprises at least five genes.

47. The method of claim 1 wherein said plurality of genes comprises at least one hundred genes.

48. The method of claim 1 wherein said plurality of genes comprises at least one thousand genes.

49. The method of claim 1 wherein said plurality of genes comprises at least twenty thousand genes.

50. The method of claim 5 wherein said expression level measurement of said gene is determined by measuring an amount of a cellular constituent encoded by said gene in one or more cells from each organism in said plurality of organisms.

51. The method of claim 50 wherein the amount of the cellular constituent comprises an abundance of an RNA species present in or secreted by said one or more cells of each said organism.

52. The method of claim 51 wherein said abundance is measured by contacting a gene transcript array with RNA species from said one or more cells, or with nucleic acid derived from said RNA species, wherein said gene transcript array comprises a positionally addressable surface with attached nucleic acids or nucleic acid mimics, said nucleic acids or nucleic acid mimics capable of hybridizing with said RNA species, or with nucleic acid derived from said RNA species.

53. The method of claim 1 wherein said set of genetic markers comprise single nucleotide polymorphisms (SNPs), microsatellite markers, restriction fragment length polymorphisms, short tandem repeats, DNA methylation markers, sequence length polymorphisms, random amplified polymorphic DNA, amplified fragment length polymorphisms, or simple sequence repeats for each organism in said plurality of organisms.

54. The method of claim 2 wherein pedigree data is used in said constructing step, and wherein said pedigree data shows one or more relationships between organisms in said plurality of organisms.

55. The method of claim 1 wherein said species is human.

56. The method of claim 1 wherein said plurality of organisms comprises an $F_2$ population and said one or more relationships between organisms in said plurality of organisms indicates which organisms in said plurality of organisms are members of said $F_2$ population.

57. A computer program product for use in conjunction with a computer system, the computer program product comprising a computer readable storage medium and a computer program mechanism embedded therein, the computer program mechanism comprising:
an identification module for identifying members of a biological pathway in a species, comprising:
(a) instructions for clustering quantitative trait locus data from a plurality of quantitative trait locus analyses to form a quantitative trait locus interaction map, wherein each quantitative trait locus analysis in said plurality of quantitative trait locus analyses is performed for a gene in a plurality of genes in the genome of said species using a genetic marker map and a quantitative trait in order to produce said quantitative trait locus data, wherein, for each quantitative trait locus analysis, said quantitative trait comprises an expression statistic for the gene for which the quantitative trait locus analysis has been performed, for each organism in a plurality of organisms that are members of said species; and wherein
said genetic marker map is constructed from a set of genetic markers associated with said species; and
(b) instructions for identifying a cluster of genes in said quantitative trait locus interaction map, thereby identifying members of said biological pathway.

58. The computer program product of claim 57 wherein said identification module further comprises instructions, executed prior to said instructions for clustering, for constructing said genetic marker map from said set of genetic markers associated with said plurality of organisms.

59. The computer program product of claim 57 wherein said identification module further comprises instructions, executed prior to said instructions for clustering, for performing each said quantitative trait locus analysis in said plurality of quantitative trait locus analyses.

60. The computer program product of claim 57 wherein said identification module further comprises instructions, executed prior to said instructions for performing, for constructing said genetic marker map from said set of genetic markers associated with said plurality of organisms.

61. The computer program product of claim 57 wherein said expression statistic for said gene is computed by transforming an expression level measurement of said gene from each organism in said plurality of organisms.

62. The computer program product of claim 61 wherein said transforming comprises normalizing the expression level measurement of said gene in order to form said expression statistic.

63. The computer program product of claim 61 wherein normalizing the expression level measurement of said gene in order to form said expression statistic is performed by a normalization technique selected from the group consisting of Z-score of intensity, median intensity, log median intensity, Z-score standard deviation log of intensity, Z-score mean absolute deviation of log intensity, calibration DNA gene set, user normalization gene set, ratio median intensity correction, and intensity background correction.

64. The computer program product of claim 57 wherein each said quantitative trait locus analysis comprises:
 (i) testing for linkage between a position in a chromosome, in the genome of said plurality of organisms, and the quantitative trait used in the quantitative trait locus analysis;
 (ii) advancing the position in said chromosome by an amount;
 (iii) repeating steps (i) and (ii) until an end of the chromosome is reached.

65. The computer program product of claim 64 wherein steps (i) through (iii) are repeated for each chromosome in said genome.

66. The computer program product of claim 64 wherein said amount is less than 100 centiMorgans.

67. The computer program product of claim 64 wherein said amount is less than 10 centiMorgans.

68. The computer program product of claim 64 wherein said amount is less than 5 centiMorgans.

69. The computer program product of claim 64 wherein said amount is less than 2.5 centiMorgans.

70. The computer program product of claim 64 wherein said testing comprises performing linkage analysis or association analysis.

71. The computer program product of claim 57 wherein said quantitative trait locus data produced from each respective quantitative trait locus analysis comprises a logarithmic of the odds score computed at each said position.

72. The computer program product of claim 57 wherein each quantitative trait locus analysis in said plurality of quantitative trait locus analyses generates a quantitative trait locus vector and
 said quantitative trait locus vector represents the gene for which said quantitative trait locus analysis has been performed, and
 said quantitative trait locus vector comprises a statistical score for each position tested by the quantitative trait locus analysis; and wherein
 said statistical score represents a correlation between (i) the expression statistic for the gene and (ii) variation in the genome in said plurality of organisms at said position.

73. The computer program product of claim 72 wherein said statistical score is a logarithmic of the odds score.

74. The computer program product of claim 72 wherein said cluster of genes are those genes that are represented by a gene analysis vector in said quantitative trait locus interaction map that shares a correlation coefficient with another gene analysis vector in said quantitative trait locus interaction map that is higher than 75% of all correlation coefficients computed between gene analysis vectors in said quantitative trait locus interaction map.

75. The computer program product of claim 72 wherein said cluster of genes are those genes that are represented by a gene analysis vector in said quantitative trait locus interaction map that shares a correlation coefficient with another gene analysis vector in said quantitative trait locus interaction map that is higher than 85% of all correlation coefficients computed between gene analysis vectors in said quantitative trait locus interaction map.

76. The computer program product of claim 72 wherein said cluster of genes are those genes that are represented by a gene analysis vector in said quantitative trait locus interaction map that shares a correlation coefficient with another gene analysis vector in said quantitative trait locus interaction map that is higher than 95% of all correlation coefficients computed between gene analysis vectors in said quantitative trait locus interaction map.

77. The computer program product of claim 72 wherein said clustering step (a) comprises clustering each said quantitative trait locus vector.

78. The computer program product of claim 57 wherein a similarity metric is in said clustering step (a) and wherein said similarity metric is a Euclidean distance, a squared Euclidean distance, a Euclidean sum of squares, a Manhattan metric, a Pearson correlation coefficient, or a squared Pearson correlation coefficient, and wherein the similarity metric is computed between quantitative trait locus vector pairs.

79. The computer program product of claim 57 wherein said instructions for clustering are performed using a nonparametric clustering technique.

80. The computer program product of claim 57 wherein said instructions for clustering comprise instructions for applying a hierarchical clustering technique, applying a k-means technique, applying a fuzzy k-means technique, applying a Jarvis-Patrick clustering, applying a self-organizing map technique, or applying a neural network technique.

81. The computer program product of claim 57 wherein said instructions for clustering comprise instructions for applying an agglomerative clustering procedure.

82. The computer program product of claim 81 wherein said agglomerative clustering procedure is a nearest-neighbor algorithm, a farthest-neighbor algorithm, an average linkage algorithm, a centroid algorithm, or a sum-of-squares algorithm.

83. The computer program product of claim 57 wherein said instructions for clustering comprise instructions for applying a divisive clustering procedure.

84. The computer program product of claim 57 wherein said identification further comprises instructions for constructing a gene expression cluster map, wherein said gene expression cluster map comprises a plurality of gene expression vectors and each gene expression vector in said plurality of gene expression vectors comprises an expression statistic for a gene in said plurality of genes.

85. The computer program product of claim 84 wherein said instructions for constructing said gene expression cluster map comprises:

instructions for computing a plurality of correlation coefficients, wherein each correlation coefficient in said plurality of correlation coefficients is computed between a pair of gene expression vectors in said plurality of gene expression vectors; and instructions for clustering said plurality of gene expression vectors using said plurality of correlation coefficients.

86. The computer program product of claim 85 wherein each correlation coefficient in said plurality of correlation coefficients is a Pearson correlation coefficient.

87. The computer program product of claim 85 wherein said instructions for clustering the plurality of gene expression vectors comprises instructions for applying a hierarchical clustering technique, applying a k-means technique, applying a fuzzy k-means technique, applying a Jarvis-Patrick clustering, applying a self-organizing map technique, or applying a neural network technique.

88. The computer program product of claim 85 wherein said instructions for clustering the plurality of gene expression vectors comprises instructions for applying an agglomerative clustering procedure.

89. The computer program product of claim 88 wherein said agglomerative clustering procedure is a nearest-neighbor algorithm, a farthest-neighbor algorithm, an average linkage algorithm, a centroid algorithm, or a sum-of-squares algorithm.

90. The computer program product of claim 88 wherein said instructions for clustering of the plurality of gene expression vectors comprises instructions for applying a divisive clustering procedure.

91. The computer program product of claim 88 wherein said instructions for constructing said gene expression cluster map comprises:

instructions for computing a plurality of metrics, wherein each metric in said plurality of metrics is computed between a gene expression vector pair in said plurality of gene expression vectors; and instructions for clustering said plurality of gene expression vectors based on said plurality of metrics in order to form said gene expression cluster map.

92. The computer program product of claim 91 wherein each metric in said plurality of metrics is selected from the group consisting of a Euclidean distance, a squared Euclidean distance, a Euclidean sum of squares, a Manhattan metric, a Pearson correlation coefficient, and a squared Pearson correlation coefficient.

93. The computer program product of claim 91 wherein said instructions for clustering of the plurality of gene expression vectors comprises instructions for applying a hierarchical clustering technique, applying a k-means technique, applying a fuzzy k-means technique, applying a Jarvis-Patrick clustering, applying a self-organizing map technique, or applying a neural network technique.

94. The computer program product of claim 91 wherein said instructions for clustering of the plurality of gene expression vectors comprises instructions for applying an agglomerative clustering procedure.

95. The computer program product of claim 94 wherein said agglomerative clustering procedure is a nearest-neighbor algorithm, a farthest-neighbor algorithm, an average linkage algorithm, a centroid algorithm, or a sum-of-squares algorithm.

96. The computer program product of claim 94 wherein said instructions for clustering of the plurality of gene expression vectors comprises instructions for applying a divisive clustering procedure.

97. The computer program product of claim 57, wherein said identification module further comprises:

(c) instructions for determining a clinical trait associated with said biological pathway.

98. The computer program product of claim 97 wherein said instructions for determining (c) comprise instructions for performing quantitative trait locus analysis using said clinical trait and said genetic marker map, wherein, when QTL arising from the quantitative trait locus analysis using said clinical trait colocalize with QTL associated with said cluster of genes, said clinical trait is associated with said biological pathway.

99. The computer program product of claim 98 wherein said instructions for determining (c) comprise instructions for correlating gene annotation information for a gene in said cluster of genes with said clinical trait.

100. The computer program product of claim 97 wherein said instructions for determining (c) comprise instructions for performing quantitative trait locus analysis using said clinical trait and said genetic marker map, wherein, when the results of the quantitative trait locus analysis using said clinical trait cocluster with said cluster of genes, said clinical trait is associated with said biological pathway.

101. The computer program product of claim 57 wherein said identification module further comprises instructions for using said cluster of genes in a multivariate analysis to determine whether said genes are genetically interacting.

102. The computer program product of claim 57 wherein said plurality of genes comprises at least five genes.

103. The computer program product of claim 57 wherein said plurality of genes comprises at least one hundred genes.

104. The computer program product of claim 57 wherein said plurality of genes comprises at least one thousand genes.

105. The computer program product of claim 57 wherein said plurality of genes comprises at least twenty thousand genes.

106. The computer program product of claim 57 wherein said set of genetic markers comprises single nucleotide polymorphisms (SNPs), microsatellite markers, restriction fragment length polymorphisms, short tandem repeats, DNA methylation markers, sequence length polymorphisms, random amplified polymorphic DNA, amplified fragment length polymorphisms, or simple sequence repeats for each organism in said plurality of organisms.

107. The computer program product of claim 58 wherein pedigree data is used by said instructions for constructing, and wherein said pedigree data shows one or more relationships between organisms in said plurality of organisms.

108. The computer program product of claim 57 wherein said species is human.

109. The computer program product of claim 57 wherein said plurality of organisms comprises an $F_2$ population and said one or more relationships between organisms in said plurality of organisms indicates which organisms in said plurality of organisms are members of said $F_2$ population.

110. A computer system for associating a gene with a trait exhibited by one or more organisms in a plurality of organisms, the computer system comprising:

a central processing unit;

a memory, coupled to the central processing unit, the memory storing an identification module, the identification module for identifying members of a biological pathway in a species, the identification module comprising:

the clustering module for clustering quantitative trait locus data from a plurality of quantitative trait locus analyses to form a quantitative trait locus interaction map; wherein (a) instructions for clustering quantitative trait locus data from a plurality of quantitative trait locus analyses to form a quantitative trait locus interaction map, wherein
each quantitative trait locus analysis in said plurality of quantitative trait locus analyses is performed for a gene in a plurality of genes in the genome of said species using a genetic marker map and a quantitative trait in order to produce said quantitative trait locus data, wherein, for each quantitative trait locus analysis, said quantitative trait comprises an expression statistic for the gene for which the quantitative trait locus analysis has been performed, for each organism in a plurality of organisms that are members of said species; and wherein
said genetic marker map is constructed from a set of genetic markers associated with said species; and (b) instructions for identifying a cluster of genes in said quantitative trait locus interaction map, thereby identifying members of said biological pathway.

111. The computer system of claim 110 wherein said identification module further comprises instructions, executed prior to said instructions for clustering, for constructing said genetic marker map from said set of genetic markers associated with said plurality of organisms.

112. The computer system of claim 110 wherein said identification module further comprises instructions, executed prior to said instructions for clustering, for performing each said quantitative trait locus analysis in said plurality of quantitative trait locus analyses.

113. The computer system of claim 110 wherein said identification module further comprises instructions, executed prior to said instructions for performing, for constructing said genetic marker map from said set of genetic markers associated with said plurality of organisms.

114. The computer system of claim 110 wherein said expression statistic for said gene is computed by transforming an expression level measurement of said gene from each organism in said plurality of organisms.

115. The computer system of claim 114 wherein said transforming comprises normalizing the expression level measurement of said gene in order to form said expression statistic.

116. The computer system of claim 114 wherein normalizing the expression level measurement of said gene in order to form said expression statistic is performed by a normalization technique selected from the group consisting of Z-score of intensity, median intensity, log median intensity, Z-score standard deviation log of intensity, Z-score mean absolute deviation of log intensity, calibration DNA gene set, user normalization gene set, ratio median intensity correction, and intensity background correction.

117. The computer system of claim 110 wherein each said quantitative trait locus analysis comprises:

(i) testing for linkage between a position in a chromosome, in the genome of said plurality of organisms, and the quantitative trait used in the quantitative trait locus analysis;

(ii) advancing the position in said chromosome by an amount;

(iii) repeating steps (i) and (ii) until an end of the chromosome is reached.

118. The computer system of claim 117 wherein steps (i) through (iii) are repeated for each chromosome in said genome.

119. The computer system of claim 117 wherein said amount is less than 100 centiMorgans.

120. The computer system of claim 117 wherein said amount is less than 10 centiMorgans.

121. The computer system of claim 117 wherein said amount is less than 5 centiMorgans.

122. The computer system of claim 117 wherein said amount is less than 2.5 centiMorgans.

123. The computer system of claim 117 wherein said testing comprises performing linkage analysis or association analysis.

124. The computer system of claim 110 wherein said quantitative trait locus data produced from each respective quantitative trait locus analysis comprises a logarithmic of the odds score computed at each said position.

125. The computer system of claim 110 wherein
each quantitative trait locus analysis in said plurality of quantitative trait locus analyses generates a quantitative trait locus vector and
said quantitative trait locus vector represents the gene for which said quantitative trait locus analysis has been performed, and
said quantitative trait locus vector comprises a statistical score for each position tested by the quantitative trait locus analysis; and wherein
said statistical score represents a correlation between (i) the expression statistic for the gene and (ii) variation in the genome in said plurality of organisms at said position.

126. The computer system of claim 125 wherein said statistical score is a logarithmic of the odds score.

127. The computer system of claim 125 wherein said cluster of genes are those genes that are represented by a gene analysis vector in said quantitative trait locus interaction map that shares a correlation coefficient with another gene analysis vector in said quantitative trait locus interaction map that is higher than 75% of all correlation coefficients computed between gene analysis vectors in said quantitative trait locus interaction map.

128. The computer system of claim 125 wherein said cluster of genes are those genes that are represented by a gene analysis vector in said quantitative trait locus interaction map that shares a correlation coefficient with another gene analysis vector in said quantitative trait locus interaction map that is higher than 85% of all correlation coefficients computed between gene analysis vectors in said quantitative trait locus interaction map.

129. The computer system of claim 125 wherein said cluster of genes are those genes that are represented by a gene analysis vector in said quantitative trait locus interaction map that shares a correlation coefficient with another gene analysis vector in said quantitative trait locus interaction map that is higher than 95% of all correlation coefficients computed between gene analysis vectors in said quantitative trait locus interaction map.

130. The computer system of claim 125 wherein said clustering step (a) comprises clustering each said quantitative trait locus vector.

131. The computer system of claim 110 wherein a similarity metric is in said clustering step (a) and wherein said similarity metric is a Euclidean distance, a squared Euclidean distance, a Euclidean sum of squares, a Manhattan metric, a Pearson correlation coefficient, or a squared Pearson correlation coefficient, and wherein the similarity metric is computed between quantitative trait locus vector pairs.

132. The computer system of claim 110 wherein said instructions for clustering are performed using a nonparametric clustering technique.

133. The computer system of claim 110 wherein said instructions for clustering comprise instructions for applying a hierarchical clustering technique, applying a k-means technique, applying a fuzzy k-means technique, applying a Jarvis-Patrick clustering, applying a self-organizing map technique, or applying a neural network technique.

134. The computer system of claim 110 wherein said instructions for clustering comprise instructions for applying an agglomerative clustering procedure.

135. The computer system of claim 134 wherein said agglomerative clustering procedure is a nearest-neighbor algorithm, a farthest-neighbor algorithm, an average linkage algorithm, a centroid algorithm, or a sum-of-squares algorithm.

136. The computer system of claim 110 wherein said instructions for clustering comprise instructions for applying a divisive clustering procedure.

137. The computer system of claim 110 wherein said identification further comprises instructions for constructing a gene expression cluster map, wherein said gene expression cluster map comprises a plurality of gene expression vectors and each gene expression vector in said plurality of gene expression vectors comprises an expression statistic for a gene in said plurality of genes.

138. The computer system of claim 137 wherein said instructions for constructing said gene expression cluster map comprises:
instructions for computing a plurality of correlation coefficients, wherein each correlation coefficient in said plurality of correlation coefficients is computed between a pair of gene expression vectors in said plurality of gene expression vectors; and
instructions for clustering said plurality of gene expression vectors using said plurality of correlation coefficients.

139. The computer system of claim 138 wherein each correlation coefficient in said plurality of correlation coefficients is a Pearson correlation coefficient.

140. The computer system of claim 138 wherein said instructions for clustering the plurality of gene expression vectors comprises instructions for applying a hierarchical clustering technique, applying a k-means technique, applying a fuzzy k-means technique, applying a Jarvis-Patrick clustering, applying a self-organizing map technique, or applying a neural network technique.

141. The computer system of claim 138 wherein said instructions for clustering the plurality of gene expression vectors comprises instructions for applying an agglomerative clustering procedure.

142. The computer system of claim 138 wherein said agglomerative clustering procedure is a nearest-neighbor algorithm, a farthest-neighbor algorithm, an average linkage algorithm, a centroid algorithm, or a sum-of-squares algorithm.

143. The computer system of claim 138 wherein said instructions for clustering of the plurality of gene expression vectors comprises instructions for applying a divisive clustering procedure.

144. The computer system of claim 138 wherein said instructions for constructing said gene expression cluster map comprises:

instructions for computing a plurality of metrics, wherein each metric in said plurality of metrics is computed between a gene expression vector pair in said plurality of gene expression vectors; and
instructions for clustering said plurality of gene expression vectors based on said plurality of metrics in order to form said gene expression cluster map.

145. The computer system of claim 144 wherein each metric in said plurality of metrics is selected from the group consisting of a Euclidean distance, a squared Euclidean distance, a Euclidean sum of squares, a Manhattan metric, a Pearson correlation coefficient, and a squared Pearson correlation coefficient.

146. The computer system of claim 144 wherein said instructions for clustering of the plurality of gene expression vectors comprises instructions for applying a hierarchical clustering technique, applying a k-means technique, applying a fuzzy k-means technique, applying a Jarvis-Patrick clustering, applying a self-organizing map technique, or applying a neural network technique.

147. The computer system of claim 144 wherein said instructions for clustering of the plurality of gene expression vectors comprises instructions for applying an agglomerative clustering procedure.

148. The computer system of claim 147 wherein said agglomerative clustering procedure is a nearest-neighbor algorithm, a farthest-neighbor algorithm, an average linkage algorithm, a centroid algorithm, or a sum-of-squares algorithm.

149. The computer system of claim 147 wherein said instructions for clustering of the plurality of gene expression vectors comprises instructions for applying a divisive clustering procedure.

150. The computer system of claim 110 wherein said identification module further comprises:
(c) instructions for determining a clinical trait associated with said biological pathway.

151. The computer system of claim 150 wherein said instructions for determining (c) comprise instructions for performing quantitative trait locus analysis using said clinical trait and said genetic marker map, wherein, when QTL arising from the quantitative trait locus analysis using said clinical trait colocalize with QTL associated with said cluster of genes, said clinical trait is associated with said biological pathway.

152. The computer system of claim 151 wherein said instructions for determining (c) comprise instructions for correlating gene annotation information for a gene in said cluster of genes with said clinical trait.

153. The computer system of claim 150 wherein said instructions for determining (c) comprise instructions for performing quantitative trait locus analysis using said clinical trait and said genetic marker map, wherein, when the results of the quantitative trait locus analysis using said clinical trait cocluster with said cluster of genes, said clinical trait is associated with said biological pathway.

154. The computer system of claim 110 wherein said identification module further comprises instructions for using said cluster of genes in a multivariate analysis to determine whether said genes are genetically interacting.

155. The computer system of claim 110 wherein said plurality of genes comprises at least five genes.

156. The computer system of claim 110 wherein said plurality of genes comprises at least one hundred genes.

157. The computer system of claim 110 wherein said plurality of genes comprises at least one thousand genes.

158. The computer system of claim 110 wherein said plurality of genes comprises at least twenty thousand genes.

159. The computer system of claim 110 wherein said set of genetic markers comprises single nucleotide polymorphisms (SNPs), microsatellite markers, restriction fragment length polymorphisms, short tandem repeats, DNA methylation markers, sequence length polymorphisms, random amplified polymorphic DNA, amplified fragment length polymorphisms, or simple sequence repeats for each organism in said plurality of organisms.

160. The computer system of claim 111 wherein pedigree data is used by said instructions for constructing, and wherein said pedigree data shows one or more relationships between organisms in said plurality of organisms.

161. The computer system of claim 110 wherein said species is human.

162. The computer system of claim 110 wherein said plurality of organisms comprises an $F_2$ population and said one or more relationships between organisms in said plurality of organisms indicates which organisms in said plurality of organisms are members of said $F_2$ population.

163. A computer system for identifying members of a biological pathway in a species, the computer system comprising:

a central processing unit;

a memory, coupled to the central processing unit, the memory storing an identification module and a database;

the database for storing quantitative trait locus data from a plurality of quantitative trait locus analyses; each quantitative trait locus analysis in said plurality of quantitative trait locus analyses is performed for a gene in a plurality of genes in the genome of said species using a genetic marker map and a quantitative trait in order to produce said quantitative trait locus data, wherein, for each quantitative trait locus analysis, said quantitative trait comprises an expression statistic for the gene, for which the quantitative trait locus analysis is performed, from each organism in a plurality of organisms that are members of said speices; and wherein said genetic marker map is constructed from a set of genetic markers associated with said species; and the identification module for clustering said quantitative trait locus data stored in said database to form a quantitative trait locus interaction map; wherein a cluster of genes in said quantitative trait locus interaction map is identified, thereby identifying members of said biological pathway.

\* \* \* \* \*